(12) United States Patent
Boice et al.

(10) Patent No.: US 11,261,232 B2
(45) Date of Patent: Mar. 1, 2022

(54) TNFRSF14 / HVEM PROTEINS AND METHODS OF USE THEREOF

(71) Applicant: MEMORIAL SLOAN KETTERING CANCER CENTER, New York, NY (US)

(72) Inventors: Michael Henry Boice, San Mateo, CA (US); Hans Guido Wendel, New York, NY (US); Darin Salloum, New York, NY (US)

(73) Assignee: MEMORIAL SLOAN KETTERING CANCER CENTER, New York, NY (US)

( * ) Notice: Subject to any disclaimer, the term of this patent is extended or adjusted under 35 U.S.C. 154(b) by 153 days.

(21) Appl. No.: 15/563,666

(22) PCT Filed: Apr. 4, 2016

(86) PCT No.: PCT/US2016/025840
§ 371 (c)(1),
(2) Date: Oct. 2, 2017

(87) PCT Pub. No.: WO2016/161415
PCT Pub. Date: Oct. 6, 2016

(65) Prior Publication Data
US 2019/0071487 A1  Mar. 7, 2019
US 2020/0017571 A9  Jan. 16, 2020

Related U.S. Application Data

(60) Provisional application No. 62/142,450, filed on Apr. 2, 2015, provisional application No. 62/303,980, filed on Mar. 4, 2016.

(51) Int. Cl.
| | | |
|---|---|---|
| *A61K 35/17* | (2015.01) | |
| *C07K 14/705* | (2006.01) | |
| *C12N 5/0783* | (2010.01) | |
| *A61P 35/00* | (2006.01) | |
| *A61K 38/17* | (2006.01) | |
| *C07K 14/725* | (2006.01) | |
| *C07K 16/28* | (2006.01) | |
| *A61K 39/00* | (2006.01) | |

(52) U.S. Cl.
CPC ........ *C07K 14/70578* (2013.01); *A61K 35/17* (2013.01); *A61K 38/1793* (2013.01); *A61P 35/00* (2018.01); *C07K 14/7051* (2013.01); *C07K 14/70521* (2013.01); *C07K 16/2803* (2013.01); *C12N 5/0636* (2013.01); *A61K 2039/505* (2013.01); *C07K 2319/03* (2013.01); *C07K 2319/33* (2013.01); *C12N 2510/00* (2013.01)

(58) Field of Classification Search
CPC .............. C12N 2510/00; C12N 5/0636; C07K 2319/33; C07K 14/70578; A61K 35/17

USPC ........................................................ 424/133.1
See application file for complete search history.

(56) References Cited

U.S. PATENT DOCUMENTS

| | | |
|---|---|---|
| 2005/0013827 A1 | 1/2005 | Busfield |
| 2009/0092608 A1 | 4/2009 | Ni et al. |
| 2011/0236401 A1 | 9/2011 | Murphy et al. |
| 2013/0034571 A1 | 2/2013 | Murphy et al. |

FOREIGN PATENT DOCUMENTS

| | | |
|---|---|---|
| WO | 000056405 A1 | 9/2000 |
| WO | 2011119979 A1 | 9/2011 |
| WO | 2012139002 A1 | 10/2012 |
| WO | 2013074738 A1 | 5/2013 |
| WO | 2014127261 A1 | 8/2014 |
| WO | 2014134165 A1 | 9/2014 |
| WO | 2014183885 A1 | 11/2014 |

OTHER PUBLICATIONS

Salloum (Cancer Immunology Research, (Nov. 2016) vol. 4, No. 11, Supp. Supplement 1. Abstract No. PR03. Meeting Info: 2nd CRI-CIMT-EATI-AACR International Cancer ImmunotherapyConference: Translating Science into Survival. New York, NY, United States. Sep. 25, 2016-Sep. 28, 2016).*
https://www.uspto.gov/patent/initiatives/biotechnologychemicalpharmaceuticalcustomer-partnership-conferences (Dan Kolker, pp. 1-36 (Sep. 17, 2020)).*
Salloum (Cancer Immunology Research, (Nov. 2016) vol. 4, No. 11, Supp. Supplement 1. Abstract No. PR03. Meeting Info: 2nd CRI-CIMT-EATI-AACR International Cancer Immunotherapy Conference: Translating Science into Survival. New York, NY, United; Abstract only).*
Boice et al., "CAR-T Cells Restore Tumor Suppressor Function in Lymphoma", Cancer Discovery, (Oct. 7, 2016), vol. 6, No. 11, pp. 1205-1205.

(Continued)

*Primary Examiner* — Lynn A Bristol
(74) *Attorney, Agent, or Firm* — Grimes & Yvon LLP

(57) ABSTRACT

In some aspects the present invention provides methods for the treatment of B-cell lymphomas. Some such methods involve administration of HVEM ectodomain polypeptides, anti-HVEM antibodies, or anti-BTLA antibodies to subjects in need thereof. Some such methods involve use of CAR T cells, such as CD19-specific CAR T cells. The present invention also provides compositions useful in such methods. These and other embodiments of the present invention and described further herein.

13 Claims, 31 Drawing Sheets

Specification includes a Sequence Listing.

(56) References Cited

OTHER PUBLICATIONS

Cheung et al, "Acquired TNFRSF14 Mutations in Follicular Lymphoma Are Associated with Worse Prognosis", Cancer Research, US, (Nov. 15, 2010), vol. 70, No. 22, pp. 9166-9174.
Cheung et al. "Evolutionarily divergent herpesviruses modulate T cell activation by targeting the herpesvirus entry mediator cosignaling pathway." PNAS, vol. 1-2, No. 37, (Sep. 13, 2005) 13218-13223.
Cheung et al., "T Cell Intrinsic Heterodimeric Complexes between HVEM and BTLA Determine Receptivity to the Surrounding Microenvironment", The Journal of Immunology, US, (2009), vol. 183, No. 11, pp. 7286-7296.
Del Rio et al., HVEM/LIGHT/BTLA/CD160 cosignalingpathways as targets for immune regulation vol. 87, Feb. 2010 Journal of Leukocyte Biology, 223-235.
Guifang Cai et al., "The CD160, BTLA, Light/HVEM pathway: a bidirectional switch regulating T-cell activation", Immunological Reviews, (May 1, 2009), vol. 229, pp. 244-258.
Hidi et al, "High Expression of the Inhibitory Receptor BTLA in T-Follicular Helper Cells and in B-Cell Small Lymphocytic Lymphoma/Chronic Lymphocytic Leukemia", American Journal of Clinical Pathology, American Society for Clinical Pathology, US, (2009), vol. 132, No. 4, pp. 589-596.
Hollyman et al. "Manufacturing validation of biologically functional T cells targeted to CD19 antigen for autologous adoptive cell therapy." J. Immunother. 2009 ; 32(2): 169-180.
Oricchio et al. The Eph-Receptor A7 Is a Soluble Tumor Suppressor for Follicular Lymphoma Cell 147, 554-564, Oct. 28, 2011.
International Search Report for PCT/US16/25840.
Partial European Search Report for EP 16774396.2.
Extended European Search Report for EP 16774396.2.

* cited by examiner

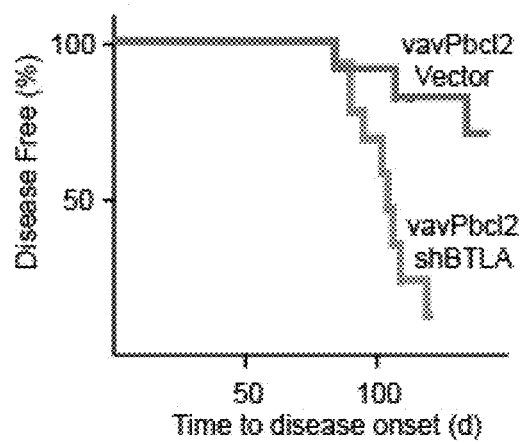
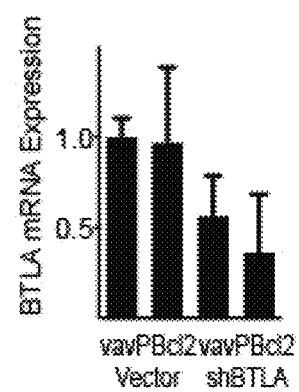
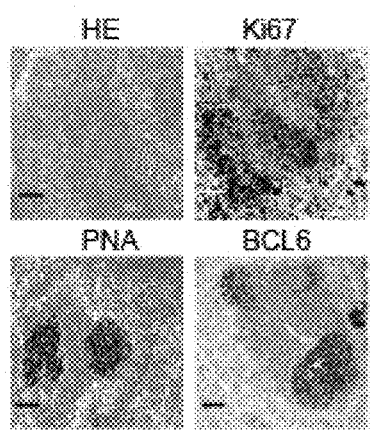
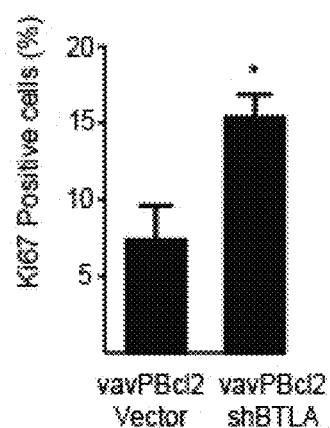
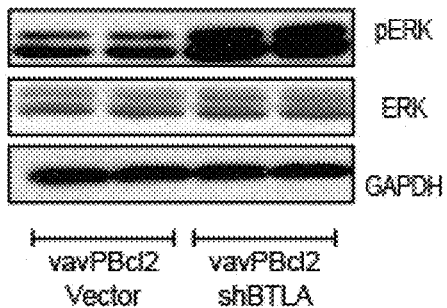
Figs. 3A - 3F

F

G

H

A
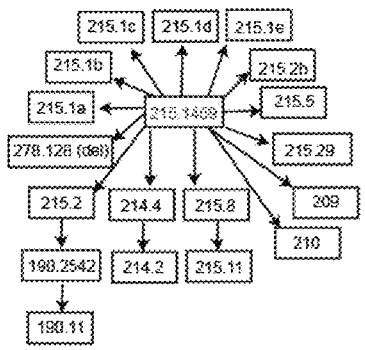
B
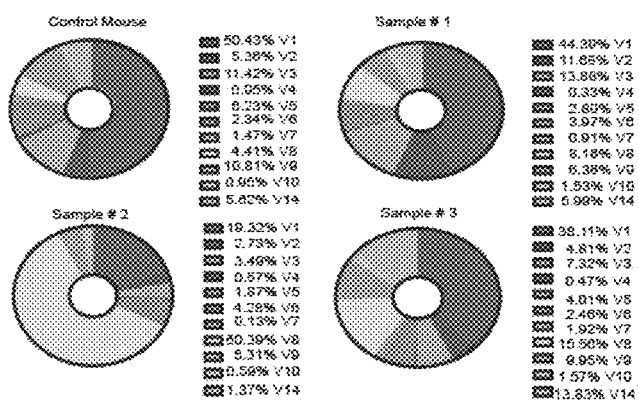
C
Figs. 10A – 10C

A

B

A

B

C

D

SEQUENCE LISTING

<160> NUMBER OF SEQ ID NOS: 13

<210> SEQ ID NO 1
<211> LENGTH: 852
<212> TYPE: DNA
<213> ORGANISM: Homo sapiens

<400> SEQUENCE: 1

```
atggagcctc ctggagactg ggggcctcct ccctggagat ccaccccaa aaccgacgtc      60 ttgaggctgg tgctgtatct caccttcctg ggagcccct gctacgcccc agctctgccg     120
tcctgcaagg aggacgagta cccagtgggc tccgagtgct gccccaagtg cagtccaggt     180
tatcgtgtga aggaggcctg cggggagctg acgggcacag tgtgtgaacc ctgccctcca     240
ggcacctaca ttgcccacct caatggccta agcaagtgtc tgcagtgcca aatgtgtgac     300
ccagccatgg gcctgcgcgc gagccggaac tgctccagga cagagaacgc cgtgtgtggc     360
tgcagcccag gccacttctg catcgtccag gacggggacc actgcgccgc gtgccgcgct     420
tacgccacct ccagcccggg ccagagggtg cagaaggag gcaccgagag tcaggacacc     480
ctgtgtcaga actgccccc ggggaccttc tctcccaatg ggaccctgga ggaatgtcag     540
caccagacca agtgcagctg gctggtgacg aaggccgag ctgggaccag cagctcccac     600
tgggtatggt ggtttctctc agggagcctc gtcatcgtca ttgtttgctc cacagttggc     660
ctaatcatat gtgtgaaaag aagaaagcca aggggtgatg tagtcaaggt gatcgtctcc     720
gtccagcgga aaagacagga ggcagaaggt gaggccacag tcattgaggc cctgcaggcc     780
cctccggacg tcaccacggt ggccgtggag gagacaatac cctcattcac ggggaggagc     840
ccaaaccact ga                                                         852
```

<210> SEQ ID NO 2
<211> LENGTH: 283
<212> TYPE: PRT
<213> ORGANISM: Homo sapiens

<400> SEQUENCE: 2

```
Met Glu Pro Pro Gly Asp Trp Gly Pro Pro Trp Arg Ser Thr Pro
1               5                   10                  15

Lys Thr Asp Val Leu Arg Leu Val Leu Tyr Leu Thr Phe Leu Gly Ala
            20                  25                  30

Pro Cys Tyr Ala Pro Ala Leu Pro Ser Cys Lys Glu Asp Glu Tyr Pro
            35                  40                  45

Val Gly Ser Glu Cys Cys Pro Lys Cys Ser Pro Gly Tyr Arg Val Lys
50                  55                  60

Glu Ala Cys Gly Glu Leu Thr Gly Thr Val Cys Glu Pro Cys Pro Pro
65                  70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
                100                 105                 110

Arg Thr Glu Asn Ala Val Cys Gly Cys Ser Pro Gly His Phe Cys Ile
            115                 120                 125

Val Gln Asp Gly Asp His Cys Ala Ala Cys Arg Ala Tyr Ala Thr Ser
130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
                165                 170                 175

Glu Glu Cys Gln His Gln Thr Lys Cys Ser Trp Leu Val Thr Lys Ala
                180                 185                 190

Gly Ala Gly Thr Ser Ser Ser His Trp Val Trp Trp Phe Leu Ser Gly
            195                 200                 205

Ser Leu Val Ile Val Ile Val Cys Ser Thr Val Gly Leu Ile Ile Cys
210                 215                 220

Val Lys Arg Arg Lys Pro Arg Gly Asp Val Val Lys Val Ile Val Ser
225                 230                 235                 240

Val Gln Arg Lys Arg Gln Glu Ala Glu Gly Glu Ala Thr Val Ile Glu
                245                 250                 255

Ala Leu Gln Ala Pro Pro Asp Val Thr Thr Val Ala Val Glu Glu Thr
            260                 265                 270

Ile Pro Ser Phe Thr Gly Arg Ser Pro Asn His
            275                 280

<210> SEQ ID NO 3
<211> LENGTH: 522
<212> TYPE: DNA
<213> ORGANISM: Homo sapiens

<400> SEQUENCE: 3
ttcctgggag cccctgcta cgccccagct ctgccgtcct gcaaggagga cgagtaccca      60
gtgggctccg agtgctgccc caagtgcagt ccaggttatc gtgtgaagga ggcctgcggg     120
gagctgacgg gcacagtgtg tgaaccctgc cctccaggca cctacattgc ccacctcaat     180
ggcctaagca agtgtctgca gtgccaaatg tgtgacccag ccatgggcct gcgcgcgagc     240
cggaactgct ccaggacaga gaacgccgtg tgtggctgca gcccaggcca cttctgcatc     300
gtccaggacg ggaccactg cgccgcgtgc cgcgcttacg ccacctccag cccgggccag     360
agggtgcaga agggaggcac cgagagtcag gacaccctgt gtcagaactg ccccccgggg     420
accttctctc ccaatgggac cctggaggaa tgtcagcacc agaccaagtg cagctggctg     480
gtgacgaagg ccggagctgg gaccagcagc tcccactggg ta                        522
```

<210> SEQ ID NO 4
<211> LENGTH: 174
<212> TYPE: PRT
<213> ORGANISM: Homo sapiens

<400> SEQUENCE: 4

Phe Leu Gly Ala Pro Cys Tyr Ala Pro Ala Leu Pro Ser Cys Lys Glu
1               5                   10                  15

Asp Glu Tyr Pro Val Gly Ser Glu Cys Cys Pro Lys Cys Ser Pro Gly
            20                  25                  30

Tyr Arg Val Lys Glu Ala Cys Gly Glu Leu Thr Gly Thr Val Cys Glu
        35                  40                  45

Pro Cys Pro Pro Gly Thr Tyr Ile Ala His Leu Asn Gly Leu Ser Lys
    50                  55                  60

Cys Leu Gln Cys Gln Met Cys Asp Pro Ala Met Gly Leu Arg Ala Ser
65                  70                  75                  80

Arg Asn Cys Ser Arg Thr Glu Asn Ala Val Cys Gly Cys Ser Pro Gly
                85                  90                  95

His Phe Cys Ile Val Gln Asp Gly Asp His Cys Ala Ala Cys Arg Ala
            100                 105                 110

Tyr Ala Thr Ser Ser Pro Gly Gln Arg Val Gln Lys Gly Gly Thr Glu
        115                 120                 125

Ser Gln Asp Thr Leu Cys Gln Asn Cys Pro Pro Gly Thr Phe Ser Pro
    130                 135                 140

Asn Gly Thr Leu Glu Glu Cys Gln His Gln Thr Lys Cys Ser Trp Leu
145                 150                 155                 160

Val Thr Lys Ala Gly Ala Gly Thr Ser Ser Ser His Trp Val
                165                 170

<210> SEQ ID NO 5
<211> LENGTH: 498
<212> TYPE: DNA
<213> ORGANISM: Homo sapiens

<400> SEQUENCE: 5
ccagctctgc cgtcctgcaa ggaggacgag tacccagtgg gctccgagtg ctgccccaag    60
tgcagtccag gttatcgtgt gaaggaggcc tgcggggagc tgacgggcac agtgtgtgaa   120
ccctgccctc aggcaccta cattgcccac ctcaatggcc taagcaagtg tctgcagtgc   180
caaatgtgtg acccagccat gggcctgcgc gcgagccgga actgctccag gacagagaac   240
gccgtgtgtg gctgcagccc aggccacttc tgcatcgtcc aggacgggga ccactgcgcc   300
gcgtgccgcg cttacgccac ctccagcccg ggccagaggg tgcagaaggg aggcaccgag   360
agtcaggaca ccctgtgtca gaactgcccc ccggggacct tctctcccaa tgggaccctg   420
gaggaatgtc agcaccagac caagtgcagc tggctggtga cgaaggccgg agctgggacc   480
agcagctccc actgggta                                                 498

<210> SEQ ID NO 6
<211> LENGTH: 166
<212> TYPE: PRT
<213> ORGANISM: Homo sapiens

<400> SEQUENCE: 6

Pro Ala Leu Pro Ser Cys Lys Glu Asp Glu Tyr Pro Val Gly Ser Glu
1               5                   10                  15

Cys Cys Pro Lys Cys Ser Pro Gly Tyr Arg Val Lys Glu Ala Cys Gly
              20                  25                  30

Glu Leu Thr Gly Thr Val Cys Glu Pro Cys Pro Pro Gly Thr Tyr Ile
         35                  40                  45

Ala His Leu Asn Gly Leu Ser Lys Cys Leu Gln Cys Gln Met Cys Asp
     50                  55                  60

Pro Ala Met Gly Leu Arg Ala Ser Arg Asn Cys Ser Arg Thr Glu Asn
65                  70                  75                  80

Ala Val Cys Gly Cys Ser Pro Gly His Phe Cys Ile Val Gln Asp Gly
             85                  90                  95

Asp His Cys Ala Ala Cys Arg Ala Tyr Ala Thr Ser Ser Pro Gly Gln
            100                 105                 110

Arg Val Gln Lys Gly Gly Thr Glu Ser Gln Asp Thr Leu Cys Gln Asn
        115                 120                 125

Cys Pro Pro Gly Thr Phe Ser Pro Asn Gly Thr Leu Glu Glu Cys Gln
    130                 135                 140

His Gln Thr Lys Cys Ser Trp Leu Val Thr Lys Ala Gly Ala Gly Thr
145                 150                 155                 160

Ser Ser Ser His Trp Val
                165

<210> SEQ ID NO 7
<211> LENGTH: 492
<212> TYPE: DNA
<213> ORGANISM: Homo sapiens

<400> SEQUENCE: 7
ctgccgtcct gcaaggagga cgagtaccca gtgggctccg agtgctgccc caagtgcagt      60
ccaggttatc gtgtgaagga ggcctgcggg gagctgacgg gcacagtgtg tgaaccctgc     120
cctccaggca cctacattgc ccacctcaat ggcctaagca agtgtctgca gtgccaaatg     180
tgtgacccag ccatgggcct gcgcgcgagc cggaactgct ccaggacaga gaacgccgtg     240
tgtggctgca gcccaggcca cttctgcatc gtccaggacg ggaccactg cgccgcgtgc     300 cgcgcttacg ccacctccag cccgggccag agggtgcaga agggaggcac cgagagtcag     360
gacaccctgt gtcagaactg ccccccgggg accttctctc ccaatgggac cctggaggaa     420
tgtcagcacc agaccaagtg cagctggctg gtgacgaagg ccggagctgg gaccagcagc     480
tcccactggg ta                                                         492

<210> SEQ ID NO 8
<211> LENGTH: 164
<212> TYPE: PRT
<213> ORGANISM: Homo sapiens

<400> SEQUENCE: 8

Leu Pro Ser Cys Lys Glu Asp Glu Tyr Pro Val Gly Ser Glu Cys Cys
1               5                   10                  15

Pro Lys Cys Ser Pro Gly Tyr Arg Val Lys Glu Ala Cys Gly Glu Leu
            20                  25                  30

Thr Gly Thr Val Cys Glu Pro Cys Pro Pro Gly Thr Tyr Ile Ala His
        35                  40                  45

Leu Asn Gly Leu Ser Lys Cys Leu Gln Cys Gln Met Cys Asp Pro Ala
    50                  55                  60

Met Gly Leu Arg Ala Ser Arg Asn Cys Ser Arg Thr Glu Asn Ala Val
65                  70                  75                  80

```
Cys Gly Cys Ser Pro Gly His Phe Cys Ile Val Gln Asp Gly Asp His
            85                  90                  95

Cys Ala Ala Cys Arg Ala Tyr Ala Thr Ser Ser Pro Gly Gln Arg Val
        100                 105                 110

Gln Lys Gly Gly Thr Glu Ser Gln Asp Thr Leu Cys Gln Asn Cys Pro
    115                 120                 125

Pro Gly Thr Phe Ser Pro Asn Gly Thr Leu Glu Glu Cys Gln His Gln
130                 135                 140

Thr Lys Cys Ser Trp Leu Val Thr Lys Ala Gly Ala Gly Thr Ser Ser
145                 150                 155                 160

Ser His Trp Val

<210> SEQ ID NO 9
<211> LENGTH: 9728
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
ggatccggat tagtccaatt tgttaaagac aggatatcag tggtccaggc tctagttttg      60
actcaacaat atcaccagct gaagcctata gagtacgagc catagataaa ataaaagatt     120
ttatttagtc tccagaaaaa ggggggaatg aaagacccca cctgtaggtt tggcaagcta     180
gcttaagtaa cgccattttg caaggcatgg aaaaatacat aactgagaat agagaagttc     240
agatcaaggt caggaacaga tggaacagct gaatatgggc caaacaggat atctgtggta     300
agcagttcct gccccggctc agggccaaga acagatggaa cagctgaata tgggccaaac     360
aggatatctg tggtaagcag ttcctgcccc ggctcagggc caagaacaga tggtccccag     420
atgcggtcca gccctcagca gtttctagag aaccatcaga tgtttccagg gtgccccaag     480
gacctgaaat gaccctgtgc cttatttgaa ctaaccaatc agttcgcttc tcgcttctgt     540
tcgcgcgctt ctgctccccg agctcaataa aagagcccac aaccctcac tcggggcgcc     600 agtcctccga ttgactgagt cgcccgggta cccgtgtatc caataaaccc tcttgcagtt     660
gcatccgact tgtggtctcg ctgttccttg ggagggtctc ctctgagtga ttgactaccc     720
gtcagcgggg gtcttttcaca catgcagcat gtatcaaaat taatttggtt ttttttctta     780
agtatttaca ttaaatggcc atagtactta agttacatt ggcttccttg aaataaacat     840
ggagtattca gaatgtgtca taaatatttc taattttaag atagtatctc cattggcttt     900 ctacttttc ttttattttt ttttgtcctc tgtcttccat tgttgttgt tgttgtttgt     960 ttgtttgttt gttggttggt tggttaattt tttttaaag atcctacact atagttcaag    1020
ctagactatt agctactctg taacccaggg tgaccttgaa gtcatgggta gcctgctgtt    1080
ttagccttcc cacatctaag attacaggta tgagctatca ttttggtat attgattgat    1140 tgattgattg atgtgtgtgt gtgtgattgt gtttgtgtgt gtgactgtga aaatgtgtgt    1200
atgggtgtgt gtgaatgtgt gtatgtatgt gtgtgtgtga gtgtgtgtgt gtgtgtgtgc    1260
atgtgtgtgt gtgtgactgt gtctatgtgt atgactgtgt gtgtgtgtgt gtgtgtgtgt    1320
gtgtgtgtgt gtgtgtgtgt gttgtgaaaa aatattctat ggtagtgaga gccaacgctc    1380
cggctcaggt gtcaggttgg ttttttgagac agagtctttc acttagcttg gaattcactg    1440
gccgtcgttt tacaacgtcg tgactgggaa accctggcg ttacccaact taatcgcctt    1500
gcagcacatc cccctttcgc cagctggcgt aatagcgaag aggcccgcac cgatcgccct    1560
```

```
tcccaacagt tgcgcagcct gaatggcgaa tggcgcctga tgcggtattt tctccttacg    1620
catctgtgcg gtatttcaca ccgcatatgg tgcactctca gtacaatctg ctctgatgcc    1680
gcatagttaa gccagccccg acacccgcca cacccgctg acgcgccctg acgggcttgt     1740
ctgctcccgg catccgctta cagacaagct gtgaccgtct ccgggagctg catgtgtcag    1800
aggttttcac cgtcatcacc gaaacgcgcg atgacgaaag gcctcgtga tacgcctatt     1860 tttataggtt aatgtcatga taataatggt ttcttagacg tcaggtggca cttttcgggg    1920
aaatgtgcgc ggaaccccta tttgtttatt tttctaaata cattcaaata tgtatccgct    1980
catgagacaa taaccctgat aaatgcttca ataatattga aaaaggaaga gtatgagtat    2040
tcaacatttc cgtgtcgccc ttattccctt ttttgcggca ttttgccttc ctgttttttgc   2100 tcacccagaa acgctggtga agtaaaaga tgctgaagat cagttgggtg cacgagtggg     2160
ttacatcgaa ctggatctca acagcggtaa gatccttgag agttttcgcc ccgaagaacg    2220
ttttccaatg atgagcactt ttaaagttct gctatgtggc gcggtattat cccgtattga    2280
cgccgggcaa gagcaactcg gtcgccgcat acactattct cagaatgact tggttgagta    2340
ctcaccagtc acagaaaagc atcttacgga tggcatgaca gtaagagaat tatgcagtgc    2400
tgccataacc atgagtgata acactgcggc caacttactt ctgacaacga tcggaggacc    2460
gaaggagcta accgcttttt tgcacaacat gggggatcat gtaactcgcc ttgatcgttg    2520
ggaaccggag ctgaatgaag ccataccaaa cgacgagcgt gacaccacga tgcctgtagc    2580
aatggcaaca acgttgcgca aactattaac tggcgaacta cttactctag cttcccggca    2640
acaattaata gactggatgg aggcggataa agttgcagga ccacttctgc gctcggccct    2700
tccggctggc tggtttattg ctgataaatc tggagccggt gagcgtgggt ctcgcggtat    2760
cattgcagca ctggggccag atggtaagcc ctcccgtatc gtagttatct acacgacggg    2820
gagtcaggca actatggatg aacgaaatag acagatcgct gagataggtg cctcactgat    2880
taagcattgg taactgtcag accaagttta ctcatatata ctttagattg atttaaaact    2940
tcatttttaa tttaaaagga tctaggtgaa gatcctttt gataatctca tgaccaaaat    3000
cccttaacgt gagttttcgt tccactgagc gtcagacccc gtagaaaaga tcaaaggatc    3060
ttcttgagat cctttttttc tgcgcgtaat ctgctgcttg caaacaaaaa aaccaccgct    3120
accagcggtg gtttgtttgc cggatcaaga gctaccaact cttttccga aggtaactgg     3180 cttcagcaga gcgcagatac caaatactgt ccttctagtg tagccgtagt taggccacca    3240
cttcaagaac tctgtagcac cgcctacata cctcgctctg ctaatcctgt taccagtggc    3300
tgctgccagt ggcgataagt cgtgtcttac cgggttggac tcaagacgat agttaccgga    3360
taaggcgcag cggtcgggct gaacggggggt tcgtgcaca cagcccagct tggagcgaac    3420
gacctacacc gaactgagat acctacagcg tgagcattga gaaagcgcca cgcttcccga    3480
agggagaaag gcggacaggt atccggtaag cggcagggtc ggaacaggag agcgcacgag    3540
ggagcttcca gggggaaacg cctggtatct ttatagtcct gtcgggtttc gccacctctg    3600
acttgagcgt cgatttttgt gatgctcgtc agggggggcgg agcctatgga aaaacgccag    3660
caacgcggcc ttttttacggt tcctggcctt ttgctggcct tttgctcaca tgttctttcc    3720
tgcgttatcc cctgattctg tggataaccg tattaccgcc tttgagtgag ctgataccgc    3780
tcgccgcagc cgaacgaccg agcgcagcga gtcagtgagc gaggaagcgg aagagcgccc    3840
aatacgcaaa ccgcctctcc ccgcgcgttg gccgattcat taatgcagct ggcacgacag    3900
```

```
gtttcccgac tggaaagcgg gcagtgagcg caacgcaatt aatgtgagtt agctcactca    3960
ttaggcaccc caggctttac actttatgct tccggctcgt atgttgtgtg gaattgtgag    4020
cggataacaa tttcacacag gaaacagcta tgaccatgat tacgccaagc tttgctctta    4080
ggagtttcct aatacatccc aaactcaaat atataaagca tttgacttgt tctatgccct    4140
aggggggcggg gggaagctaa gccagctttt tttaacattt aaaatgttaa ttccatttta    4200
aatgcacaga tgtttttatt tcataagggt ttcaatgtgc atgaatgctg caatattcct    4260
gttaccaaag ctagtataaa taaaaataga taaacgtgga aattacttag agtttctgtc    4320
attaacgttt ccttcctcag ttgacaacat aaatgcgctg ctgagcaagc cagtttgcat    4380
ctgtcaggat caatttccca ttatgccagt catattaatt actagtcaat tagttgattt    4440
ttatttttga catatacatg tgaatgaaag accccacctg taggtttggc aagctagctt    4500
aagtaacgcc attttgcaag gcatggaaaa atacataact gagaatagaa aagttcagat    4560
caaggtcagg aacagatgga acagctgaat atgggccaaa caggatatct gtggtaagca    4620
gttcctgccc cggctcaggg ccaagaacag atggaacagc tgaatatggg ccaaacagga    4680
tatctgtggt aagcagttcc tgccccggct cagggccaag aacagatggt ccccagatgc    4740
ggtccagccc tcagcagttt ctagagaacc atcagatgtt tccagggtgc cccaaggacc    4800
tgaaatgacc ctgtgcctta tttgaactaa ccaatcagtt cgcttctcgc ttctgttcgc    4860
gcgcttatgc tccccgagct caataaaaga gcccacaacc cctcactcgg ggcgccagtc    4920
ctccgattga ctgagtcgcc cgggtacccg tgtatccaat aaaccctctt gcagttgcat    4980
ccgacttgtg gtctcgctgt tccttgggag ggtctcctct gagtgattga ctacccgtca    5040
gcgggggtct ttcatttggg ggctcgtccg ggatcgggag acccctgccc agggaccacc    5100
gacccaccac cgggaggtaa gctggccagc aacttatctg tgtctgtccg attgtctagt    5160
gtctatgact gattttatgc gcctgcgtcg gtactagtta gctaactagc tctgtatctg    5220
gcggacccgt ggtggaactg acgagttcgg aacacccggc cgcaaccctg ggagacgtcc    5280
cagggacttc gggggccgtt tttgtggccc gacctgagtc ctaaaatccc gatcgtttag    5340
gactcttttgg tgcaccccccc ttagaggagg gatatgtggt tctggtagga gacgagaacc    5400
taaaacagtt cccgcctccg tctgaattttt tgctttcggt ttgggaccga agccgcgccg    5460
cgcgtcttgt ctgctgcagc atcgttctgt gttgtctctg tctgactgtg tttctgtatt    5520
tgtctgaaaa tatgggcccg ggctagactg ttaccactcc cttaagtttg accttaggtc    5580
actggaaaga tgtcgagcgg atcgctcaca accagtcggt agatgtcaag aagagacgtt    5640
gggttacctt ctgctctgca gaatggccaa cctttaacgt cggatggccg cgagacggca    5700
cctttaaccg agacctcatc acccaggtta agatcaaggt cttttcacct ggcccgcatg    5760
gacacccaga ccaggtcccc tacatcgtga cctgggaagc cttggctttt gacccccctc    5820
cctgggtcaa gccctttgta caccctaagc ctccgcctcc tcttcctcca tccgccccgt    5880
ctctccccct tgaacctcct cgttcgaccc cgcctcgatc ctccctttat ccagccctca    5940
ctccttctct aggcgccccc atatggccat atgagatctt atatgggggca ccccgcccc    6000
ttgtaaactt ccctgaccct gacatgacaa gagttactaa cagcccctct ctccaagctc    6060
acttacaggc tctctactta gtccagcacg aagtctggag acctctggcg gcagcctacc    6120
aagaacaact ggaccgaccg gtggtacctc acccttaccg agtcggcgac acagtgtggg    6180
tccgccgaca ccagactaag aacctagaac ctcgctggaa aggaccttac acagtcctgc    6240
tgaccacccc caccgccctc aaagtagacg gcatcgcagc ttggatacac gccgcccacg    6300
```

```
tgaaggctgc cgaccccggg ggtggaccat cctctagact gccatggctc tcccagtgac    6360
tgccctactg cttcccctag cgcttctcct gcatgcagag gtgaagctgc agcagtctgg    6420
ggctgagctg gtgaggcctg gtcctcagt gaagatttcc tgcaaggctt ctggctatgc     6480
attcagtagc tactggatga actgggtgaa gcagaggcct ggacagggtc ttgagtggat    6540
tggacagatt tatcctggag atggtgatac taactacaat ggaaagttca agggtcaagc    6600
cacactgact gcagacaaat cctccagcac agcctcatg cagctcagcg gcctaacatc     6660
tgaggactct gcggtctatt tctgtgcaag aaagaccatt agttcggtag tagatttcta    6720
ctttgactac tggggccaag gaccacggt caccgtctcc tcaggtggag gtggatcagg     6780
tggaggtgga tctggtggag gtggatctga cattgagctc acccagtctc caaaattcat    6840
gtccacatca gtaggagaca gggtcagcgt cacctgcaag gccagtcaga atgtgggtac    6900
taatgtagcc tggtatcaac agaaaccagg acaatctcct aaaccactga tttactcggc    6960
aacctaccgg aacagtggag tccctgatcg cttcacaggc agtggatctg ggacagattt    7020
cactctcacc atcactaacg tgcagtctaa agacttggca gactatttct gtcaacaata    7080
taacaggtat ccgtacacgt tcggaggggg gaccaagctg gagatcaaac gggcggccgc    7140
aattgaagtt atgtatcctc ctccttacct agacaatgag aagagcaatg gaaccattat    7200
ccatgtgaaa gggaaacacc tttgtccaag tcccctattt cccggacctt ctaagccctt    7260
ttgggtgctg gtggtggttg gtggagtcct ggcttgctat agcttgctag taacagtggc    7320
ctttattatt ttctgggtga ggagtaagag gagcaggctc ctgcacagtg actacatgaa    7380
catgactccc cgccgccccg ggcccacccg caagcattac cagccctatg ccccaccacg    7440
cgacttcgca gcctatcgct ccagagtgaa gttcagcagg agcgcagacg cccccgcgta    7500
ccagcagggc cagaaccagc tctataacga gctcaatcta ggacgaagag aggagtacga    7560
tgttttggac aagagacgtg gccgggaccc tgagatgggg ggaaagccga aaggaagaa     7620 ccctcaggaa ggcctgtaca atgaactgca gaaagataag atggcggagg cctacagtga    7680
gattgggatg aaaggcgagc gccggagggg caagggcac gatggccttt accagggtct     7740
cagtacagcc accaaggaca cctacgacgc ccttcacatg caggccctgc cccctcgcta    7800
acagccactc gagcccccc ccctaacgtt actggccgaa gccgcttgga ataaggccgg     7860
tgtgcgtttg tctatatgtt attttccacc atattgccgt cttttggcaa tgtgagggcc    7920
cggaaacctg gccctgtctt cttgacgagc attcctaggg gtctttcccc tctcgccaaa    7980
ggaatgcaag gtctgttgaa tgtcgtgaag gaagcagttc ctctggaagc ttcttgaaga    8040
caaacaacgt ctgtagcgac cctttgcagg cagcggaacc ccccaccctgg cgacaggtgc    8100 ctctgcggcc aaaagccacg tgtataagat acacctgcaa aggcggcaca accccagtgc    8160
cacgttgtga gttggatagt tgtggaaaga gtcaaatggc tctcctcaag cgtattcaac    8220
aaggggctga aggatgccca gaaggtaccc cattgtatgg gatctgatct ggggcctcgg    8280
tgcacatgct ttacatgtgt ttagtcgagg ttaaaaaacg tctaggcccc ccgaaccacg    8340
gggacgtggt tttcctttga aaaacacgat aataccatgg tgagcaaggg cgaggagctg    8400
ttcaccgggg tggtgcccat cctggtcgag ctggacggcg acgtaaacgg ccacaagttc    8460
agcgtgtccg gcgagggcga gggcgatgcc acctacggca agctgaccct gaagttcatc    8520
tgcaccaccg gcaagctgcc cgtgccctgg cccaccctcg tgaccaccct gacctacggc    8580
gtgcagtgct tcagccgcta ccccgaccac atgaagcagc acgacttctt caagtccgcc    8640
```

-continued

| | |
|---|---|
| atgcccgaag gctacgtcca ggagcgcacc atcttcttca aggacgacgg caactacaag | 8700 |
| acccgcgccg aggtgaagtt cgagggcgac accctggtga accgcatcga gctgaagggc | 8760 |
| atcgacttca aggaggacgg caacatcctg gggcacaagc tggagtacaa ctacaacagc | 8820 |
| cacaacgtct atatcatggc cgacaagcag aagaacggca tcaaggtgaa cttcaagatc | 8880 |
| cgccacaaca tcgaggacgg cagcgtgcag ctcgccgacc actaccagca gaaccccccc | 8940 |
| atcggcgacg cccccgtgct gctgcccgac aaccactacc tgagcaccca gtccgccctg | 9000 |
| agcaaagacc ccaacgagaa gcgcgatcac atggtcctgc tggagttcgt gaccgccgcc | 9060 |
| gggatcactc tcggcatgga cgagctgtac aagggcagcg cgccaccaa cttcagcctg | 9120 |
| ctgaagcagg ccggcgacgt ggaggagaac cccggcccca tggagacaga cactcctg | 9180 |
| ctatgggtac tgctgctctg gttccaggt ccactggtg acccagctct gccgtcctgc | 9240 |
| aaggaggacg agtacccagt gggctccgag tgctgcccca gtgcagtcc aggttatcgt | 9300 |
| gtgaaggagg cctgcgggga gctgacgggc acagtgtgtg aaccctgccc tccaggcacc | 9360 |
| tacattgccc acctcaatgg cctaagcaag tgtctgcagt gccaaatgtg tgacccagcc | 9420 |
| atgggcctgc gcgcgagccg gaactgctcc aggacagaga cgccgtgtg tggctgcagc | 9480 |
| ccaggccact tctgcatcgt ccaggacggg gaccactgcg ccgcgtgccg cgcttacgcc | 9540 |
| acctccagcc cgggccagag ggtgcagaag ggaggcaccg agagtcagga caccctgtgt | 9600 |
| cagaactgcc ccccgggac cttctctccc aatgggaccc tggaggaatg tcagcaccag | 9660 |
| accaagtgca gctggctggt gacgaaggcc ggagctggga ccagcagctc ccactgggta | 9720 |
| tagctcga | 9728 |

<210> SEQ ID NO 10
<211> LENGTH: 3519
<212> TYPE: DNA
<213> ORGANISM: Homo sapiens

<400> SEQUENCE: 10

| | |
|---|---|
| tccttcatac cggcccttcc cctcggcttt gcctggacag ctcctgcctc ccgcagggcc | 60 |
| cacctgtgtc cccagcgcc gctccaccca gcaggcctga gccctctct gctgccagac | 120 |
| accccctgct gcccactctc ctgctgctcg ggttctgagg cacagcttgt cacaccgagg | 180 |
| cggattctct ttctctttct cttttctcttc tggcccacag ccgcagcaat ggcgctgagt | 240 |
| tcctctgctg gagttcatcc tgctagctgg gttcccgagc tgccggtctg agcctgaggc | 300 |
| atggagcctc ctggagactg ggggcctcct ccctggagat ccaccccaa aaccgacgtc | 360 |
| ttgaggctgg tgctgtatct caccttcctg ggagcccct gctacgcccc agctctgccg | 420 |
| tcctgcaagg aggacgagta cccagtgggc tccgagtgct gccccaagtg cagtccaggt | 480 |
| tatcgtgtga aggaggcctg cggggagctg acgggcacag tgtgtgaacc ctgccctcca | 540 |
| ggcacctaca ttgcccacct caatggccta agcaagtgtc tgcagtgcca aatgtgtgac | 600 |
| ccagccatgg gcctgcgcgc gagccggaac tgctccagga cagagaacgc cgtgtgtggc | 660 |
| tgcagcccag gccacttctg catcgtccag gacggggacc actgcgccgc gtgccgcgct | 720 |
| tacgccacct ccagcccggg ccagagggtg cagaagggag gcaccgagag tcaggacacc | 780 |
| ctgtgtcaga actgccccc ggggaccttc tctcccaatg ggaccctgga ggaatgtcag | 840 |
| caccagacca gtgcagctg gctggtgacg aaggccggag ctgggaccag cagctcccac | 900 |
| tgggtatggt ggtttctctc agggagcctc gtcatcgtca ttgtttgctc cacagttggc | 960 |
| ctaatcatat gtgtgaaaag aagaaagcca agggtgatg tagtcaaggt gatcgtctcc | 1020 |

```
gtccagcgga aaagacagga ggcagaaggt gaggccacag tcattgaggc cctgcaggcc    1080
cctccggacg tcaccacggt ggccgtggag gagacaatac cctcattcac ggggaggagc    1140
ccaaaccact gacccacaga ctctgcaccc cgacgccaga gatacctgga gcgacggctg    1200
ctgaaagagg ctgtccacct ggcggaacca ccggagcccg gaggcttggg ggctccgccc    1260
tgggctggct tccgtctcct ccagtggagg gagaggtggg gcccctgctg gggtagagct    1320
ggggacgcca cgtgccattc ccatgggcca gtgagggcct ggggcctctg ttctgctgtg    1380
gcctgagctc cccagagtcc tgaggaggag cgccagttgc ccctcgctca cagaccacac    1440
acccagccct cctgggccag cccagagggc ccttcagacc ccagctgtct gcgcgtctga    1500
ctcttgtggc ctcagcagga caggccccgg gcactgcctc acagccaagg ctggactggg    1560
ttggctgcag tgtggtgttt agtggatacc acatcggaag tgattttcta aattggattt    1620
gaattcggct cctgttttct atttgtcatg aaacagtgta tttggggaga tgctgtggga    1680
ggatgtaaat atcttgtttc tcctcaaact gtcacctccc ggtgtttctt gctgaacaag    1740
gagttccagg atggctgctg ggctgttcgg gggacccctg ccctcctccc gtcatgcctg    1800
ggggttcact ccacccagag aggagccctg gccgccccett catatcccaa cagctgagct    1860
ctcagtgggc tcttctgacc tctgtggctc cgtccgaggc tattgctgtg gattctgatg    1920
ctcaaatggt gtcagatttg cccagtaaaa accccagatc tacatctgac ctacacttcc    1980
cagctgtgtc caccgagaaa ccccagtatc agtgacgcct gctgtgccca gccctctcca    2040
cctgctccgg gaacccgcca ggcccaggtc ccgctggcag gggcttcacc aggcctctga    2100
gccacacatt catttaatgg tcgggatgag gccccttttcc ccacatctga agttagaagc    2160
ggtgagggga atgaccctgc agccatgcca tgaggatgga ggccacatag cccctccgag    2220
catgcccgct ccacccogcc ctaccccctc tcctttcctt gtcacctgcc tcagcagag    2280 cccccaggct gagccaccca ccccaactcc tctcctgcca cccettgtcc tgtggaagct    2340 ttggcttagc gtcctggggt gtggagaggc ccatgcaggc caggtggagc cctgggcccc    2400
tagaaagcag cacttctggc tgccccaccc cgtgtcaccc tctccccaac tggaggcgtg    2460
gtctccaggg accacgggcc tccctgtgca tggaccggct cctgaccacc gtccagggtc    2520
attgccaggg tacctttcta gaggctgacc ccatagacct ggctgccccc cagtgctaga    2580
tgggagccaa gcacagcctg cccttctgcc cacagtcccg ggggcaggtg ggagcatggg    2640
gccatggagt gagcgggcag gggtggcaga gggctccctg gtcaggggcc ccaacttccc    2700
ttcccccagg gaggccacct gacatctggg ctccaggcac agcaggaagc ccacctgccc    2760
caacctgtag ctcctcctcc tgggaggagc catggatcct ggaaaagctc tggggccacc    2820
tcccaggttt gggggacag agctccaaga gacgacggct ggggacacga gccctcatgg    2880
ggccgctgtg tgctcacccc ttgatttttct tcttttcatg catgagatta ggccaagtgt    2940
ggagaaatca atgatgttga cgatgaggct ccctgagaga aatcacaccc agcgggagct    3000
gctgctccca ggtctggcct cggtcaccag ccacctgctg catccgcggg agtggggccg    3060
aggacatggg agtggcaggt gcagcccccg gtactcactc agcccagggg agtgtccctg    3120
gctcccaggg ctctgggagg tgagggcagg tcccggggga ggctgggtta gtggcagctc    3180
cgggatgaga cctcagaggt ctgtctgact tgtccaagcc cggctatggg gaggtggggg    3240
gaaggaagga agaggagaga aataaggaga ggctgggcaa agaagacagg acggcagagg    3300
gagaggggag agaagtggga ggcagccagc agcgcagggc cctgagagta tttcagcggc    3360
```

```
accgctgtcc tgggccgccc ggtgccacat ctttgaaaac agttgtttaa tttaagcttg   3420
tccactcagt agctgttgaa tgtgggaggt tatcttgttc tattcaagtt gctataaaaa   3480
taaaaactac catagactgg gaaaaaaaaa aaaaaaaaa                          3519
```

<210> SEQ ID NO 11
<211> LENGTH: 893
<212> TYPE: DNA
<213> ORGANISM: Mus musculus

<400> SEQUENCE: 11

```
gctcttggcc tgaagtttct tgatcaagaa aatggaacct ctcccaggat gggggtcggc    60
accctggagc caggccccta cagacaacac cttcaggctg gtgccttgtg tcttcctttt   120
gaacttgctg cagcgcatct ctgcccagcc ctcatgcaga caggaggagt tccttgtggg   180
agacgagtgc tgccccatgt gcaacccagg ttaccatgtg aagcaggtct gcagtgagca   240
tacaggcaca gtgtgtgccc cctgtccccc acagacatat accgcccatg caaatggcct   300
gagcaagtgt ctgccctgcg gagtctgtga tccagacatg gcctgctga cctggcagga   360 gtgctccagc tggaaggaca ctgtgtgcag atgcatccca ggctacttct gtgagaacca   420
ggatgggagc cactgttcca catgcttgca gcacaccacc tgccctccag gcagagggt   480 agagaagaga gggactcacg accaggacac tgtatgtgct gactgcctaa cagggacctt   540
ctcacttgga gggactcagg aggaatgcct gccctggacc aactgcagtg catttcaaca   600
ggaagtaaga cgtgggacca acagcacaga caccacctgc tcctcccagg tcgtctacta   660
cgttgtgtcc atccttttgc cacttgtgat agtgggagct gggatagctg gattcctcat   720
ctgcacgcga agacacctgc acaccagctc agtggccaag gagctggagc ctttccagga   780
acaacaggag aacaccatca ggtttccagt caccgaggtt gggtttgctg agaccgagga   840
ggagacagcc tccaactgaa caaattctgg gtgacaagac accgaggaga cgt          893
```

<210> SEQ ID NO 12
<211> LENGTH: 2089
<212> TYPE: DNA
<213> ORGANISM: Rattus norvegicus

<400> SEQUENCE: 12

```
cacttttagt tttagctggg gctcatgaga gtgtgtgagg aggtccaaag tccatggggc    60
tcctggcctg cagtgtcttg attaagaaaa tggaacctct cccgggatgg gagtcgtcac   120
cctggagccg gcagacaac accttcaggc tggtgccgtg tgtcttcctt ttgaacttgt   180
tgcagtgtat ctctgcccag cccttgtgca gacaggagga gttttctgtt ggggatgagt   240
gctgccccat gtgcaatcca ggttaccatg tgaagcaggt ctgcagtgag catacaggca   300
cagtgtgtgc ccctgtcccc cacagacct ataccgccca tgcgaatggc ctgagcaagt   360
gtctgccctg cggagtctgt gatccagaca tgggcctgct gacctggcag gagtgctcca   420
gctggaagga cactgtgtgc agatgcatct caggttactt ctgtgagaac caggatgggg   480
gcgcctgttc cacatgcttg cctcacgccg cctgccctcc aggacagagg gtacagaaga   540
gaggtactta cagccatgac actgtatgtg ctgactgcct acaggaacc ttctcacttg   600 gcgggactca ggaggaatgc ctgccctgga ccaagtgcag taccttttcaa cgggaagtaa   660 acatgggac cagcagcaca gacaccaccct gctccttcca gaccttctac atcgtcgttg   720
tgatagtggg agttgcgata gtgggagctg gggtagttga attcctcctc cgcaagcaaa   780
gacagcggca taccagcata gtggccagtg agctggaggc tttccagcag gagcaacaag   840
```

| | |
|---|---|
| aggacgccat caggtttcca gtcatcgagg ttggtccttc tgtgaccgag gaggaggcag | 900 |
| ccttcaactg catgaattcg gggtgatgag acaccttgga gaccctgatg ggaagtttcc | 960 |
| atatgccaga ggggcacggc agatgccctg ggctgctacg gcatcacatg cagggggaga | 1020 |
| tgttgccatg gcccagggtg tagcagttgc tttgtccttc ttagtgttaa atgggatcat | 1080 |
| ctgcgcccat gcaaacgatc caaagtctgt atcagtgaca gttaccacag accctatgcc | 1140 |
| ctacttccca atcttccag acagcctgtc taaaccctag gcctttgacc gtcctggaaa | 1200 |
| tgttaaaggc tgctcatcca gagggctgct gagcacggcc ttctgggtc agggtgcttg | 1260 |
| cgatgagaca agaatatggc attggtggat tttattttga agtttctggg gctggaatct | 1320 |
| tgcccatacc aggcaagtgc tttattcctg agctacattc ccaagactct ttccgttttt | 1380 |
| tatcttgagg caaagtcaca cggaattgtc tgggccaacc atggactcct tctgtatctt | 1440 |
| gggcaagcct caaacttgac gcttctacct ctgctcttca agtaacactg tgatgacctg | 1500 |
| cgtggtcctc cagacggggc gggtcaatgc cttctatttt ctttgtgtgt gtgtgtgtgt | 1560 |
| gtgtgtgtgt gtgtgtgtgt gtgtgcacac gcgtacctgt tacccccttt tcccaccgga | 1620 |
| cctagcccca gagagttttc tgcaggcccc agagaactaa gttttactcc ctcagacaca | 1680 |
| agtctgctga gggattgatt aatcactgac tccacacctc tcctcagtgt acctgacctg | 1740 |
| tcaaagctgg tcttcagtac ttgttcctta gtagctagcc atcttgagcc agcccgaggc | 1800 |
| tcatcaattc agctagatcg gcctaccact gagcgttggg catcccttg gctctgcctt | 1860 |
| ctcagcgctg gtttagggc acacagcact atgccaaact tctaaagtgg attctgggga | 1920 |
| tgagcccagt ttcaagaatg caggtccttt ctcatgctgt ggaacagcac tcttagtgac | 1980 |
| caaaccattc ccttggcttc agaatgaatg tctaagttat tttctacttg tcataggaaa | 2040 |
| taaatatttt tgttacacaa aaaaaaaaaa aaaaaaaaa aaaaaaaa | 2089 |

<210> SEQ ID NO 13
<211> LENGTH: 846
<212> TYPE: DNA
<213> ORGANISM: Macaca mulatta

<400> SEQUENCE: 13

| | |
|---|---|
| atggagcctc ctggaggttg ggggtctcct ccccggagac ccgcccccaa agccgacttc | 60 |
| ttgacgctgg tgctgtatct caccttcctg gatcccccct gctacgcccc agctctgccc | 120 |
| tcctgcaaag aggacgagta cccagtgggc tctgagtgct gtcccaagtg cggtccaggt | 180 |
| ttccacgtga ggcaggcctg tggggagcag acgggcacgg tgtgtgaacc ctgctctccg | 240 |
| gggacctaca ttgctcactt caatggcctg agcaagtgtc tgcagtgcca atgtgtgac | 300 |
| ccagccatgg gcctgcgcac aagccggaac tgctccacga cagcgaacgc cctgtgtggc | 360 |
| tgcagcccag ccacttctg catcatccag gacgggggacc actgcgccgc gtgccgcgct | 420 |
| tacgccacct ccagcccggg ccagagggta cagaagggag gcactgagag tcaggacacc | 480 |
| ctgtgtcaga actgccccccc ggggaccttc tcttccaatg ggaccctgga ggaatgccag | 540 |
| cacgggacca agtgcagcaa atggctggtg acggaggccg acctgggac cagcagcttc | 600 |
| cgctgggtgt ggtggtttct ctcagggacc ctcatcgtca ttgtcattgt tggcctaata | 660 |
| cttggcctaa tatgtgtgaa aagaagaaag tcaaggggcg atgtagtcaa ggtgatcgtc | 720 |

```
tccgtccagc ggaagagaca ggaggcagaa ggtgaagcca tagtcactga ggccctgcag      780
gcccctccgg acatcaccac agtggccgtg gaagagacag aacctgcatt cactgggagg      840
agctga                                                                  846
```

TNFRSF14 / HVEM PROTEINS AND METHODS OF USE THEREOF

CROSS-REFERENCE TO RELATED APPLICATIONS

This application is a U.S. National Stage entry under 35 U.S.C. § 371 of International patent Application No. PCT/US2016/025840, filed Apr. 4, 2016, which claims the benefit of priority of U.S. Provisional Patent Application No. 62/142,450 filed on Apr. 2, 2015, and U.S. Provisional Patent Application No. 62/303,980 filed on Mar. 4, 2016, the contents of which are hereby incorporated by reference in their entireties.

STATEMENT OF GOVERNMENT SUPPORT

This invention was made with government support under grant numbers CA183876 and CA190384 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Apr. 1, 2016, is named MSKCC_008_WO1_SL.txt and is 33,621 bytes in size.

COPYRIGHT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

INCORPORATION BY REFERENCE

For countries that permit incorporation by reference, all of the references cited in this disclosure are hereby incorporated by reference in their entireties. In addition, any manufacturers' instructions or catalogues for any products cited or mentioned herein are incorporated by reference. Documents incorporated by reference into this text, or any teachings therein, can be used in the practice of the present invention.

BACKGROUND

Follicular Lymphoma (FL) is the second most common type of lymphoma and is generally considered incurable with the current treatment options. FL arises from germinal center (GC) B-cells, a highly specialized population of immune cells that is capable of explosive growth upon antigen encounter. It is known that FL is a disease that is highly dependent on interactions from other cells in the tumor microenvironment. However, which of these multiple interactions are important for the development and maintenance of the disease is presently not clear. While recent genomic studies have catalogued the most common FL mutations, providing new insights into the mechanisms that cause B-cell malignancies, there remains a need in the art for a better understanding of how FL interacts with the tumor microenvironment and a translation of these understandings into new and improved methods for treatment of follicular lymphoma, as well as other forms of cancer.

Tumor necrosis factor receptor superfamily member 14 (TNFRSF14), which is also referred to as herpes virus entry mediator or "HVEM", is a multi-functional tumor suppressor in lymphoma. It is a cell surface receptor expressed in the hematopoietic system—specifically on B-cells and T-cells. HVEM is frequently mutated or deleted in lymphomas, such as follicular lymphoma (FL) and diffuse large B-cell lymphoma (DLBCL). HVEM is mutated in around 44% of FL patients. Furthermore, HVEM mutation status correlates with FL patient survival.

SUMMARY OF THE INVENTION

Some of the main aspects of the present invention are summarized below. Additional aspects are described in the Detailed Description of the Invention, Examples, Drawings, and Claims sections of this disclosure. The description in each section of this patent disclosure, regardless of any heading or sub-heading titles, is intended to be read in conjunction with all other sections. Furthermore, the various embodiments described in each section of this disclosure can be combined in various different ways, and all such combinations are intended to fall within the scope of the present invention.

The present invention is based, in part, on certain discoveries that are described in more detail in the "Examples" section of this patent application. For example, it has now been discovered that loss of cell surface expression of TNFRSF14/HVEM significantly accelerates development of follicular lymphoma (FL) in an in vivo mouse model.

Furthermore it has now been shown that treatment with a "soluble HVEM ectodomain polypeptide" can inhibit the proliferation of B-cell lymphoma cell lines in vitro and inhibit B-cell lymphoma tumor growth in vivo in a BTLA-dependent manner. Building on these discoveries, the present invention provides various compositions and methods for the treatment of B-cell lymphomas.

In some embodiments the present invention provides a nucleic acid molecule comprising: (a) a nucleotide sequence encoding a chimeric antigen receptor (CAR), and (b) a nucleotide sequence encoding a HVEM ectodomain polypeptide, such as a soluble HVEM ectodomain polypeptide. In other embodiments the present invention provides a nucleic acid molecule comprising: (a) a nucleotide sequence encoding a chimeric antigen receptor (CAR), and (b) a nucleotide sequence encoding an antibody, wherein the antibody is an anti-HVEM antibody of an anti-BTLA antibody. In some such embodiments the CAR binds to a cell surface antigen present on the surface of B-cell lymphoma cells. In some such embodiments the CAR binds to a cell surface antigen selected from the group consisting of CD19, CD20, CD22, CD30, Igk, and ROR1. In some preferred embodiments the CAR binds to CD19. In some embodiments the present invention provides vectors that comprise any of such nucleic acid molecules—such as expression vectors and cloning vectors. In some embodiments the present invention provides a cell that comprises any of such nucleic acid molecules, or any such vectors—i.e. a genetically modified cell. In some such embodiments the cell is a T cell.

In some embodiments the present invention provides genetically modified T cells comprising: (a) a nucleotide sequence encoding a chimeric antigen receptor (CAR), and (b) a nucleotide sequence encoding a HVEM ectodomain polypeptide, such as a soluble HVEM ectodomain polypeptide. In other embodiments the present invention provides genetically modified T-cells comprising: (a) a nucleotide sequence encoding a chimeric antigen receptor (CAR), and (b) a nucleotide sequence encoding an antibody, wherein the antibody is either an anti-HVEM antibody or an anti-BTLA antibody. Such genetically modified T-cells are a type of "CAR T cells." In some such embodiments the CAR binds to a cell surface antigen present on the surface of B-cell lymphoma cells. In some such embodiments the CAR binds to a cell surface antigen selected from the group consisting of CD19, CD20, CD22, CD30, Igk, and ROR1. In some preferred embodiments the CAR binds to CD19. In some such embodiments the nucleotide sequence encoding the chimeric antigen receptor (CAR) and the nucleotide sequence encoding either the soluble HVEM ectodomain polypeptide, the anti-HVEM antibody, or the anti-BTLA antibody, are within the same nucleic acid molecule. Conversely, in other embodiments the nucleotide sequence encoding the chimeric antigen receptor (CAR) and the nucleotide sequence encoding either the soluble HVEM ectodomain polypeptide, the anti-HVEM antibody, or the anti-BTLA antibody, are not within the same nucleic acid molecule (i.e. the nucleotide sequence encoding the chimeric antigen receptor (CAR) and the nucleotide sequence encoding either the soluble HVEM ectodomain polypeptide, anti-HVEM antibody, or anti-BTLA antibody can be provided in different nucleic acid molecules, e.g. in different vectors).

In some embodiments the present invention provides certain non-CAR-based compositions that can be useful for the targeted delivery of HVEM ectodomain polypeptides (such as soluble HVEM ectodomain polypeptides), anti-HVEM antibodies, or anti-BTLA antibodies (i.e. "active agents") to B-cell lymphoma cells. For example, in one embodiment the present invention provides a composition (for example a pharmaceutical composition) comprising (i) an active agent, and (b) a "targeting antibody" (which term includes antigen-binding antibody fragments) that binds to a cell surface antigen on a B-cell lymphoma cell. In some such embodiments the active agent and the targeting antibody are covalently linked. Conversely in other embodiments the active agent and the targeting antibody are not covalently linked. In some embodiments the active agent and/or the targeting antibody are provided in a delivery particle, such as a nanoparticle, liposome, polymeric micelle, lipoprotein-based drug carrier, and/or dendrinier. In some such embodiments the targeting antibody binds to CD19, CD20, CD22, CD30, IgK or ROR1 on the surface of B-cell lymphoma cells. In some preferred embodiments the targeting antibody binds to CD19. In other preferred embodiments the targeting antibody binds to CD20. In some such embodiments the anti-CD20 antibody rituximab, or an antigen-binding fragment thereof, is used.

In some embodiments the present invention provides various methods of treatment of B-cell lymphomas. In some embodiments such methods comprise administering to a subject in need thereof an effective amount of a HVEM ectodomain polypeptide, such as a soluble HVEM ectodomain polypeptide. In some embodiments such methods comprise administering to a subject in need thereof an effective amount of an anti-HVEM antibody or an anti-BTLA antibody. In certain embodiments the subject is a mammal, such as a human, a non-human primate, or a mouse. In preferred embodiments the subject is a human.

Some of such treatment methods involve using CAR T-cells to target the HVEM ectodomain polypeptide (e.g. the soluble HVEM ectodomain polypeptide), the anti-HVEM, or the anti-BTLA antibody (i.e. the "active agents") to tumor cells in the subject. For example some of such treatment methods involve administering to a subject in need thereof any of the genetically modified T cells described above or elsewhere in this patent disclosure. Conversely, some of such treatment methods involve using other means (i.e. non-CAR T cell based methods) to target the active agents to tumor cells in the subject. In some such methods the active agents are targeted to a B-cell lymphoma/lymphoma cell using a "targeting antibody" (which term includes antigen-binding antibody fragments) that binds to an antigen on the surface of a B-cell lymphoma/lymphoma cell. In some such embodiments the targeting antibody binds to CD19, CD20, CD22, CD30, IgK, or ROR1 on B-cell lymphoma cells. In some preferred embodiments the targeting antibody binds to CD19. In other preferred embodiments the targeting antibody binds to CD20. In some such embodiments the anti-CD20 antibody rituximab, or an antigen-binding fragment thereof, is used. In some such embodiments the active agent is covalently attached to the targeting antibody. In some embodiments the active agents and targeting antibody are present in a single fusion protein. In some embodiments the active agent need not be covalently attached to the targeting antibody. In some embodiments the active agent and/or the targeting antibody maybe provided in delivery particles, such as nanoparticles, liposomes, polymeric micelles, lipoprotein-based drug carriers, and/or dendrimers.

Any of the treatment methods described above, and elsewhere in this patent disclosure, may be combined with one more other treatment methods useful in B-cell lymphoma therapy. Such other treatment methods include, but are not limited to, treatment with an anti-CD20 antibody, rituximab, ibrutinib, cyclophosphamide, doxorubicin, vincristine, prednisone, and/or idelalisib, and/or treatment by chemotherapy, radiation therapy, immunotherapy, or surgery.

In some embodiments the present invention provides compositions for use in treating B-cell lymphomas, wherein such compositions comprise a HVEM ectodomain polypeptide, such as a soluble HVEM ectodomain polypeptide. In some embodiments the present invention provides compositions for use in treating B-cell lymphomas, wherein such compositions comprise an anti-HVEM antibody or an anti-BTLA antibody. In other embodiments the present invention provides compositions for use in treating B-cell lymphomas, wherein the composition comprises a nucleotide sequence encoding a HVEM ectodomain polypeptide, such as a soluble HVEM ectodomain polypeptide. Similarly, in some embodiments the present invention provides compositions for use in treating B-cell lymphomas, wherein the composition comprises a nucleotide sequence encoding an anti-HVEM antibody or an anti-BTLA antibody.

In those embodiments described above, or elsewhere in this patent disclosure, that involve HVEM ectodomain polypeptides, such as a soluble HVEM ectodomain polypeptides, in some of such embodiments the polypeptide comprises, consists of, or consists essentially of, a HVEM CRD1 domain. In some such embodiments the polypeptide comprises a HVEM CRD1 domain and a HVEM CDR2 domain. In some such embodiments the polypeptide comprises a HVEM CRD1 domain, a HVEM CDR2 domain, and a HVEM CDR3 domain. In some such embodiments the polypeptide does not comprise a HVEM CDR3 domain. In some such embodiments the polypeptide does not comprise a HVEM CRD2 domain. In some such embodiments the polypeptide does not comprise a HVEM CRD2 and does not comprise a HVEM CDR3 domain. In some such embodiments the polypeptide comprises a HVEM CDR1 and a HVEM CDR2 domain but does not comprise a HVEM CDR3 domain. In some such embodiments the polypeptide has one or more activities selected from the group consisting of: BTLA binding, BTLA activation, inhibition of proliferation of BTLA$^+$ B-cell lymphoma cells, inhibition of growth of a BTLA$^+$ B-cell lymphoma, stimulation of the activity of CD8+ T-cells, inhibition of the activation of B-cell receptors in B-cell lymphoma cells, inhibition of secretion of IL-21 by follicular T helper (TFH) cells, inhibition of secretion of IL-21 by B-cell lymphoma cells, inhibition of BCR pathway activation, and inhibition of BTK, SYK, and/or ERK activation in BTLA$^+$B-cell lymphoma cells. In some such embodiments the polypeptide comprises SEQ ID NO: 4, 6, or 8. In some such embodiments the polypeptide is encoded by a nucleotide sequence comprising SEQ ID NO: 3, 5, or 7. In some such embodiments the polypeptide is encoded by a nucleic acid molecule that also encodes a chimeric antigen receptor (CAR), such as, for example, the nucleic acid molecule provided herein as SEQ ID NO: 9.

In those embodiments described above, or elsewhere in this patent disclosure, that involve an anti-HVEM antibody or an anti-BTLA antibody, in some of such embodiments the antibody is a human antibody, a humanized antibody, or a chimeric antibody. In some such embodiments the antibody is an antibody fragment, such as, for example, a Fab, Fab', F(ab')2, Fv, scFv, or nanobody antibody fragment. Furthermore, in some such embodiments the antibody has one or more activities selected from the group consisting of: HVEM activation, BTLA activation, inhibition of proliferation of BTLA$^+$ B-cell lymphoma cells, inhibition of growth of a BTLA$^+$ B-cell lymphoma, stimulation of the activity of CD8+ T-cells, inhibition of the activation of B-cell receptors in B-cell lymphoma cells, inhibition of secretion of IL-21 by follicular T helper (TFH) cells, inhibition of secretion of IL-21 by B-cell lymphoma cells, inhibition of BCR pathway activation, and inhibition of BTK, SYK, and/or ERK activation in BTLA$^+$ B-cell lymphoma cells.

In those embodiments described above, or elsewhere in this patent disclosure, that involve a B-lymphoma or a B-cell lymphoma cell, in some of such embodiments the B-cell lymphoma/lymphoma cell is a Germinal Center ("GC") B-cell lymphoma/lymphoma cell. In some of such embodiments the B-cell lymphoma/lymphoma cell is a follicular lymphoma (FL) or FL cell. In some of such embodiments the B-cell lymphoma/lymphoma cell is a diffuse large B-cell lymphoma (DLBCL) or DLBCL cell. In some such embodiments the B-cell lymphoma/lymphoma cell is BTLA$^+$. In some such embodiments the B-cell lymphoma/lymphoma cell is BTLA$^{hi}$. In some such embodiments the B-cell lymphoma/lymphoma cell is HVEM$^-$. In some such embodiments the B-cell lymphoma/lymphoma cell comprises a HVEM mutation.

Some of the main embodiments of the present invention are summarized above. Additional aspects are provided and described in the Brief Description of the Figures, Detailed Description of the Invention, Examples, Claims, and Figures sections of this patent application. Furthermore, it should be understood that variations and combinations of each of the embodiments described herein are contemplated and are intended to fall within the scope of the present invention.

BRIEF DESCRIPTION OF THE FIGURES

FIG. 1A, Summary of HVEM mutations in 141 FL samples; FIG. 1B, Distribution of copy number (CN) status in the 41 patients harboring a HVEM CN alteration; FIG. 1C, Percentage of each type of mutation found in FL patients; FIG. 1D, Chr. 1p36 deletions affect the HVEM locus (MSKCC cohort, n=64); FIG. 1E, GISTIC analysis indicates frequent homozygous HVEM deletions; FIG. 1F, Frequency of deletions by zygosity in indolent FL; FIG. 1G, quantification of positive and negative cases represented on TMAs stained for HVEM and BTLA. FIG. 1H and FIG. 1I, immune-histochemical staining. In the first panel (FIG. 1H) strong staining with an anti-HVEM antibody was observed in the malignant cell population whereas BTLA remained largely negative. The second panel (FIG. 1I) is negative for HVEM but shows strong positivity for BTLA in all tumor cells. Original magnification ×400, scale bars equal FIG. 2A-G. HVEM acts as a tumor suppressor in a mouse model of FL.

FIG. 3A-F. BTLA deficiency recapitulates the effect of HVEM loss on lymphoma development in vivo. FIG. 3A, Kaplan-Meier analysis of disease free survival (vector, n=11: shRNA against BTLA, n=16, p<0.01); FIG. 3B, qRT-PCR analysis of BTLA mRNA expression in control (vector) and BTLA (shBTLA) lymphomas; FIG. 3C, Pathological analysis of shBTLA tumors stained for representative sections including H&E, Ki67, PNA and BCL6, scale bars=100 µm; FIG. 3D, Quantification of Ki67 staining in shBTLA tumors (n=6, p<0.01); FIG. 3E, Surface analysis of vavPBc12-vector and vavPBc12-shBTLA tumors; FIG. 3F, Immunoblot on representative tumors probed as indicated.

FIG. 4A and FIG. 4B, Quantification of FACS analysis of phosphorylated BTK (pBTK) expression in BCL1 cells after stimulation with anti-IgM in the presence of solHVEM (10 µg/ml) or Ibrutinib (10 nM) without (FIG. 4A) or with (FIG. 4B) the knockdown of BTLA (shBTLA); FIG. 4C, FACS analysis of BTLA expression on purified primary human FL B cells distinguishes samples with high (BTLA$^{hi}$) and low (BTLAlo) surface BTLA expression); FIG. 4D, FACS analysis for the indicated signaling molecules in human primary FL B cells that were BTLA$^{hi}$ or BTLAlo and stimulated with anti-human IgG (3 min; 10 µg/ml and H$_2$O$_2$ 1 mM) in the presence or absence of the soluble HVEM ectodomain (solHVEM; 10 µg/ml) (right); FIG. 4E, Percentage of pSyk inhibition was calculated by comparing the ratio of MFI of pSyk+/−solHVEM and was correlated to BTLA ratio of MFI (r=0.697, p=0.03, Purified FL B cells, n=10, grade 1 and grade 2).

FIG. 5A, Immunohistofluorescence staining for the FDC marker CD21/35 and the FRC marker Collagen 1 on control lymphomas (vector) and HVEM knockdown lymphomas (shHVEM) (n=3 for each, scale bars=100 μm); FIG. 5B and FIG. 5C, Systematic quantification of CD21/35 (left) and collagen I (right) staining in control (Vector) and HVEM deficient (shHVEM) lymphomas based on 12 areas in the T-cell zone and 30 areas in the B-cell zone per mice (cumulative number for 3 mice), respectively;  $p<0.01$; * $p<0.001$ by parametric t-test; FIG. 5D and FIG. 5E, CXCL13 (FIG. 5D) and CCL19 (FIG. 5E) expression by qRT-PCR on control (vector) and HVEM knockdown (shHVEM) lymphomas (mean of four replicates, error bars indicate standard deviation, * $p<0.01$); FIG. 5F, qRT-PCR measurement of the LTa, LTb, and TNFa mRNA expression in B cells isolated from the spleens of vector and shHVEM mice (n=3); FIG. 5G-I, qRT-PCR measurement of TNFa (FIG. 5G), LTa (FIG. 5H), and LTb (FIG. 5I) in B cell line BCL1 after 24 hrs of treatment with solHVEM (10 μg/ml).

FIG. 6A-I. Increased TFH cell recruitment supports to HVEM deficient lymphoma B cells. FIG. 6A, FACS identification and sorting of human GC derived TFH cells based on the markers CD3pos, CD4pos, CD25neg, PD1hi, CXCR-5hi, left: isotypic control; right; staining with anti-BTLA antibody; FIG. 6B and FIG. 6C, FACS measurement (FIG. 6B) and quantification (FIG. 6C) of intra-tumoral TFH cells in control and HVEM deficient murine lymphomas; FIG. 6D and FIG. 6E, qRT-PCR measurement of IL21 (FIG. 6D), and IL4 (FIG. 6E) in sorted intra-tumoral T cells (N=?); FIG. 6F, qRT-PCR measurement of the LTa, LTb, and TNFa mRNA expression in T cells isolated from the spleens of vector and shHVEM mice * p<?; G-I, qRT-PCR measurement of TNFa (FIG. 6G), LTa (FIG. 6H), and LTb (FIG. 6I) in cell sorted TFH (n=4) cultured with anti-CD3/anti-CD28 Mabs in presence or not of soluble HVEM (solHVEM, 10 μg/ml), each symbol represents an independent TFH sample.

FIG. 7A and FIG. 7B, FACS measurement of phosphorylated BTK (pBTK) in DOHH2 lymphoma cells that were stimulated with anti-IgG in the presence of absence of Pro37-Val202 solHVEM (5 μg/ml) or the BTK inhibitor ibrutinib (10 nM); quantified in (B) (* indicated $p<0.01$); FIG. 7C, immunoblot on myc/bcl2 cells after treatment with Leu39-Val202 solHVEM (5 μg/ml) probed as indicated; FIG. 7D, Analysis of cell proliferation across a panel of BTLA$^{hi}$ and BTLAlo lymphoma cell lines treated with Leu39-Val202 solHVEM (5 μg/ml); FIG. 7E, Representative picture of in vivo treatment of engrafted myc-bcl2 murine lymphomas, FIG. 7F, In vivo treatment of engrafted myc-bcl2 murine lymphomas with either vehicle or the Leu 39-Val202 HVEM ectodomain upon formation of well-palpable tumors 75 mm3 20 m of Leu39-Val202 solHVEM was intratumoral injected every three days (indicated by arrows); FIG. 7G, Immunoblot on lysates from Leu39-Val202 treated and untreated lymphomas proved as indicated; FIG. 7H, Microscopic pathology on Leu39-Val202 treated and untreated lymphomas stained as indicated, scale bars=100

FIG. 8A, Chr. 1p36 deletions in a second series of FL (UNMC, n=198); inset: GISTIC analysis of DNA copy number indicates frequent homozygous loss; FIG. 8B, Frequency of deletions by zygosity in transformed FLs; FIG. 8C, Distribution of the percentages of HVEM-positive tumor cells in FL tissue specimens arranged on a TMA. Colors represent staining intensity; FIG. 8D, Expression of HVEM in Human FLs samples in HVEM wt (left) and HVEM mutated or deleted samples (right); FIG. 8E, The number of cases presenting with the respective staining intensities for CD272 (BTLA) in the follicular lymphoma cells are shown; FIG. 8F, BTLA staining intensity in Human FLs in cases that are HVEM+ or HVEM−; FIG. 8G, Numbers indicate breakdown of how individual TMA sections scored.

FIG. 9A, Kaplan-Meier analysis of tumor onset using a second shRNA against HVEM (shHVEM-2) compared to empty vector (vector, n=11; shHVEM-2, n=12; $p<0.01$); FIG. 9B, qRT-PCR analysis of HVEM mRNA expression in control (vector) and HVEM (shHVEM) lymphomas; FIG. 9C, FACS analysis for the indicated surface markers on HVEM deficient lymphomas (shHVEM); FIG. 9D, quantification of Ki67 in vavPBcl2-vector and vavPBcl2-HVEM tumors (n=6; mean±s.d; t-test: * $p<0.01$); FIG. 9E, FACS analysis for the indicated surface markers on HVEM deficient lymphomas (shHVEM).

FIG. 10A-C. Analysis of variants in the VDJ region of mouse tumors. FIG. 10A, Analysis of μ heavy chain transcripts from three samples of shHVEM mice to evaluate clonality and monitor clonotypes within the samples. Table represents clones amplified above 1% (control samples had none above 0.66%). Clones with the same VDJ junction and minimal differences within the V and JH segments are represented as variants in the last column; FIG. 10B, Evolution tree shows ongoing clonal evolution of the dominant clone by connecting variants observed in the CDR3 region with (VH8.12/D2.4/JH1) in shHVEM sample #2. FIG. 10C, Pie charts represent VH family usage of the three samples (and control) analyzed to globally assess the B cell repertoire in each sample. Abundant clonal proliferation in samples 2 and 3 accordingly show clear repertoire biases.

FIG. 12A, Immunohistofluorescence staining of CD20pos B cells, Transglutaminasepos FRCs, and CD21Lpos FDCs in reactive lymph nodes and two separate human follicular lymphoma tissue specimens; FIG. 12B, Flowchart of the image processing for FRC density (Collagen I); briefly, images were thresholded and transformed to binaries images, then a watershed algorithm was applied and number of polygons evaluated and analyzed by ImageJ software; FIG. 12C, Number of polygons indicates FRC density in control lymphomas (vector) and HVEM knockdown lymphomas showing no difference in FRC contribution. 40 areas were selected in the T cell zone and analyzed per mice (n=3 per each group); FIG. 12D-F, qRT-PCR measurement of TNFa (FIG. 12D), LTa (FIG. 12E), and LTb (FIG. 12F) in mouse B-cell line EuMyc-Bcl2.

FIG. 13A and FIG. 13B, qRT-PCR measurement of the receptors for IL21 (IL-21ra; A), and IL4 (IL4ra; B) in purified lymphoma B cells; FIG. 13C, Viability of purified murine TFH cells (samples: n=4) that were cultured for 3 days with or without (UN) stimulation by anti-CD3/anti-CD28 in the presence or absence of the soluble HVEM ectodomain (solHVEM: 10 µg/ml); FIG. 13D, Cell-Sorted GC-TFH cultured with anti-CD3/anti-CD28 Mabs in presence or not of solHVEM; production of CXCL13(FIG. 13E) and IL-21(FIG. 13F) evaluated by ELISA.

FIG. 14A and FIG. 14B, Quantification of pSYK levels in DOHH2 lymphoma cells that were stimulated with anti-IgG in the presence or absence of Pro37-Val202 solHVEM (5 µg/ml) (* indicated p<0.01); representative FACS measurement in (FIG. 14B) FIG. 14C, FACS analysis of BTLA expression in a panel of lymphoma lines including murine myc/bcl2 lymphomas and human lines (DOHH2, Su-DHL6, Granta, Ly10); FIG. 14D, representative pictures of tumors from mice; FIG. 14E, tumor weight of mouse tumors (n=3, p<0.01).

FIG. 15A, Representative FACS plots. FIG. 15B, Quantification of mean fluorescence intensity of phospho-BTK after treatment with vehicle or drug.

FIG. 16A, Representative FACS plots. FIG. 16B, Quantification of mean fluorescence intentisty of phospho-SYK after treatment with vehicle or drug.

FIG. 25A, Schematic illustration of delivery of soluble HVEM polypeptides to lymphoma cells using CD19-specific chimeric antigen receptor (CAR)-modified T cells that are modified to constitutively secrete soluble HVEM. FIG. 25B, Schematic illustration of chimeric antigen receptor (CAR) molecule comprising a soluble HVEM sequence (HVEM P37-V202).

FIG. 26A, Viability of purified murine OT1 cells (n=2) that were cultured for 24 hours with or without stimulation by anti-CD3/anti-CD28 in the presence or absence of the soluble HVEM ectodomain (solHVEM: 10 m/m1); FIG. 26B, Percentage of activated murine OT1 cells identified by FACS, OT1 cells were culture as in FIG. 26A.

FIG. 28A, 19-28-HVEM-modified T cells exhibit enhanced in vitro cytotoxicity to B cells with high BTLA expression as compared to control 19-28 T cells. DOHH2 or Raji cells were incubated with GFP-labeled CAR-T cells at given T (target) to E (effector T cell) ratios. At the indicated times cells were labeled with Annexin V and DAPI, and the percentage of GFP—viable cells was assessed by FACS. FIG. 28B, FACS analysis of BTLA expression on B cell lines distinguishes samples with high and low surface BTLA expression. FIG. 28C-D, 19-28-HVEM-modified T cells exhibit enhanced cytotoxicity in vivo on DOHH2 tumors as compared to control 19-28 T cells. Xenografts were generated by s.c. injections of 5Mio DoHH2 human lymphoma cells mixed with Matrigel (BD) into flanks of NOD/SCID (NOD.CB17-Prkdcscid/J) mice. Upon visible tumor formation (20 mm$^3$), mice were given a single dose of 1 Mio anti-CD19 CAR T cells that are with or without HVEM secretion. T cells containing prostate-specific membrane antigen (PSMA) scFv was used as a control CAR. FIG. 28C, Representative tumors isolated upon mouse sacrifice. FIG. 28D, Quantification of tumor size.

DETAILED DESCRIPTION

Figures 1A, 1B, 1C, 1D, 1E, 1F, 1G, 1H, 1I:
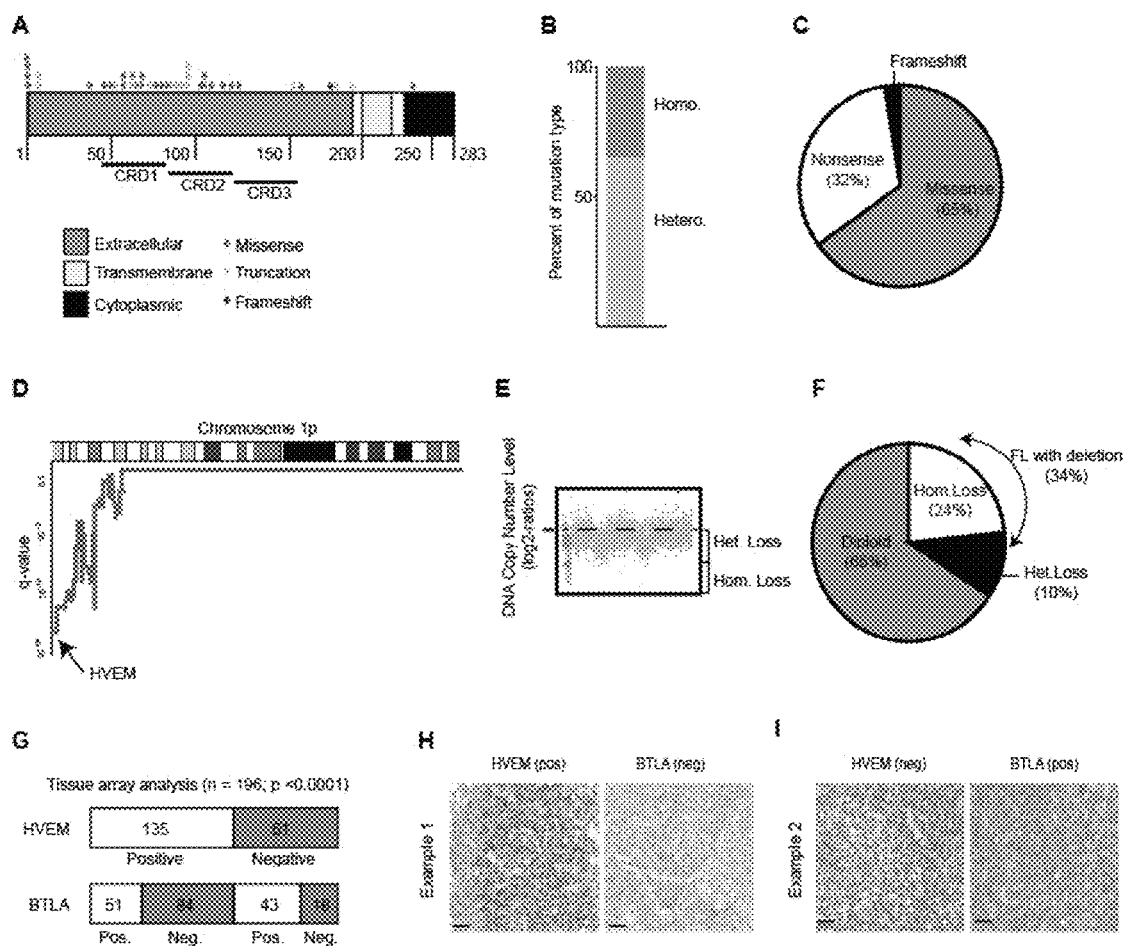
FIG. 1A-I. The HVEM-BTLA interaction is disrupted in the majority of human FLs.

The sub-headings provided below, and throughout this patent disclosure, are not intended to denote limitations of the various aspects or embodiments of the invention, which are to be understood by reference to the specification as a whole. For example, this Detailed Description is intended to read in conjunction with, and to expand upon, the description provided in the Summary of the Invention section of this application.

1. Definitions & Abbreviations

As used in this specification and the appended claims, the singular forms "a," "an," and "the" include plural referents, unless the context clearly dictates otherwise. The terms "a" (or "an") as well as the terms "one or more" and "at least one" can be used interchangeably.

Furthermore, "and/or" is to be taken as specific disclosure of each of the two specified features or components with or without the other. Thus, the term "and/or" as used in a phrase such as "A and/or B" is intended to include A and B, A or B, A (alone), and B (alone). Likewise, the term "and/or" as used in a phrase such as "A, B, and/or C" is intended to include A, B, and C; A, B, or C; A or B; A or C; B or C; A and B; A and C; B and C; A (alone); B (alone); and C (alone).

Units, prefixes, and symbols are denoted in their Système International de Unites (SI) accepted form. Numeric ranges provided herein are inclusive of the numbers defining the range. Where a numeric term is preceded by "about," the term includes the stated number and values±10% of the stated number.

An "active agent" is an agent (e.g. a molecule or a cell) as described and/or claimed herein that is, or that comprises, a soluble HVEM ectodomain polypeptide, an anti-HVEM antibody, or an anti-BTLA antibody, or a nucleotide sequence that encodes any of such agents. Active agents include, but are not limited to, cells (such as T cells), polypeptides/proteins, and nucleic acid molecules.

The terms "inhibit," "block," "reduce," and "suppress" are used interchangeably and refer to any statistically significant decrease in biological activity, including—but not limited to—full blocking of the activity.

"TNFRSF14" refers to "tumor necrosis factor receptor superfamily member 14."

"HVEM" refers to "herpes virus entry mediator."

TNFRSF14 and HVEM are one and the same. Accordingly, the terms TNFRSF14 and HVEM are used interchangeably throughout this patent disclosure. In some instances these proteins may be referred to herein as "TNFRSF14/HVEM."

"BTLA" refers to "B and T lymphocyte attenuator."

The terms "BTLA-positive" and "BTLA+" are used interchangeably herein to refer to tumors or cells that express (or express detectable levels of) BTLA.

The terms "BTLA-negative" and "BTLA−" are also used interchangeably herein and refer to tumors or cells that do not express (or do not express detectable levels of) BTLA.

The term "BTLA$^{hi}$" refers to tumors or cells that express high levels of BTLA.

The term "BTLA$^{lo}$" refers to tumors or cells that express low levels of BTLA.

The terms BTLA$^+$, BTLA$^-$, BTLA$^{hi}$, and BTLA$^{lo}$ are all used to denote expression levels of BTLA in relative terms. For example a cell or a tumor may be classified as BTLA$^+$ as opposed to BTLA$^-$. Similarly, a cell or a tumor may be classified as BTLA$^{hi}$ as opposed to BTLA$^{lo}$. The usage of such relative terms to denote expression levels, for example using "+" versus "−" and "hi" versus "lo" terminology, is standard in the art and the meaning of such terms will be clear to those of ordinary skill in the art. For example, one of skill in the art will understand that a cell or tumor may be designated as BTLA$^+$ based on determination of BTLA expression levels in comparison with suitable positive (i.e. BTLA expressing) and/or negative (i.e. non-BTLA expressing) controls. Similarly, one of skill in the art will understand that a cell or tumor may be designated as BTLA$^{hi}$ based on determination of BTLA expression levels in comparison with suitable highly expressing and/or weakly expressing controls. Suitable assays for making such comparative determinations are provided in Example 1, and include, but are not limited to, immunohistochemistry and flow cytometry or FACS-based assays. Similarly, suitable control cell types for making such comparative determinations are provided in Example 1.

"CAR" refers to a "chimeric antigen receptor."

"CAR T cells" refers to genetically modified T cells that have been engineered to express a CAR.

Various other terms are defined elsewhere in this patent disclosure, where used. Furthermore, terms that are not specifically defined herein may be more fully understood in the context in which the terms are used and/or by reference to the specification in its entirety. Where no explicit definition is provided all technical and scientific terms used herein have the meanings commonly understood by those of ordinary skill in the art to which this invention pertains.

2. TNFRSF14/HVEM Polypeptides

TNFRSF14 was originally identified as a mediator of the entry herpes simplex virus-1 into human and mouse cells for (Montgomery, Warner et al. 1996). The TNFRSF14 receptor is one of 29 currently known receptors within the TNF receptor superfamily. The TNFRSF14 receptor gene is located on chromosome 1p36 in humans—a site that has been frequently reported to harbor tumor suppressors due to its frequent deletion in multiple cancers (Bagchi and Mills 2008). TNFRS14 is expressed throughout the major human tissues but exhibits its highest levels of expression in cells of the hematopoietic system. TNFRSF14 is an insoluble transmembrane protein comprising an intracellular domain, a trans-membrane domain, and an extracellular domain or "ectodomain." The extracellular domain of TNFRSF14 comprises 3 cysteine rich domains or "CRDs"—referred to as CRD1, CRD2, and TNFRSF14 can interact with multiple different ligands, which bind to TNFRSF14 via its CRD domains. Some such ligands deliver co-stimulatory signals: such as the ligands "lymphotoxin-like, inducible expression, competes with herpes simplex virus glycoprotein D for HVEM, a receptor expressed by T lymphocytes" (or "LIGHT"), and LTa. Other ligands deliver co-inhibitory signals: such as CD160, glycoprotein D (gD), and "B and T lymphocyte attenuator" or "BTLA" (Murphy and Murphy 2010).

A full length human TNFRS14/HVEM protein sequence is provided in FIG. 29 and SEQ ID NO. 2. A nucleotide sequence that encodes the protein of SEQ ID NO. 2 (i.e. the full length human TNFRS14/HVEM protein) is provided in FIG. 29 and SEQ ID NO. 1. A further nucleotide sequence that encodes a full length human TNFRS14/HVEM protein is provided as SEQ ID NO. 10 (NCBI Reference Sequence: NM 003820.3). A nucleotide sequence that encodes a full length mouse TNFRS14/HVEM protein is provided as SEQ ID NO. 11 (NCBI Reference Sequence: NM 178931.2). A nucleotide sequence that encodes a full length rat TNFRS14/HVEM protein is provided as SEQ ID NO. 12 (NCBI Reference Sequence: NM 001015034.1). A nucleotide sequence that encodes a full length monkey TNFRS14/

HVEM protein sequence is provided as SEQ ID NO. 13 (NCBI Reference Sequence: 001043357.1). Other full-length TNFRS14/HVEM protein sequences, and nucleotide sequences that encode such protein sequences, are also known in the art. Some embodiments of the present invention involve these full-length HVEM sequences.

However, most of the embodiments of the present invention involve non-naturally occurring soluble fragments of the full-length insoluble HVEM protein referred to herein as "soluble HVEM ectodomain polypeptides." As discussed in the Examples section of this patent application, it has now been demonstrated that soluble HVEM ectodomain polypeptides inhibit B-cell tumor growth and that this activity involves binding to BTLA. It is already known that within the HVEM ectodomain, the CRD1 domain is the essential binding site for BTLA and that deletion of the CRD1 domain blocks the inhibitory activity of HVEM, and there is also evidence that the CRD2 domain of HVEM provides structural support of CRD1 binding ligands such as BTLA (see M.L.del Rio, 2010, Gonzales 2004, and Bjordahl 2013, the contents of each of which are hereby incorporated by reference). Thus, the "soluble HVEM ectodomain polypeptides" of the present invention comprise at least a CRD1 domain (and may, optionally, comprise the CRD2 and/or CRD3 and/or other HVEM ectodomain regions), and do not comprise the HVEM trans-membrane or intracellular domains. Furthermore, the "soluble HVEM ectodomain polypeptides" of the present invention exhibit one or more of the following functional properties: tumor suppressor activity in BTLA+/hi B-cell lymphomas (e.g. ability to inhibit B-cell lymphoma cell growth in vitro and/or tumor growth in vivo in BTLA+/hi B-cell lymphomas), ability to increase/stimulate the activity of CD8+ T-cells, ability to inhibit/reduce activation of B-cell receptors in lymphoma cells, ability to inhibit/reduce the secretion of IL-21by follicular T helper (TFH) cells or lymphoma B cells, ability to inhibit BCR pathway activation in a BTLA-dependent manner, and ability to inhibit BTK, SYK, and/or ERK activation in BTLA+/hi lymphoma cells (e.g. DOHH2 cells). Suitable assays for assessing such functional properties are provided in the Examples section of this patent application.

The sequences of several exemplary soluble HVEM ectodomain polypeptides are provided herein—as summarized in Table 1, below. The amino acid numbering of all of the soluble HVEM ectodomain polypeptides described herein is based on SEQ ID NO. 2 (i.e. SEQ ID NO. 4 is amino acids 29-202 of SEQ ID NO. 2, SEQ ID NO. 6 is amino acids 37-202 of SEQ ID NO. 2, and SEQ ID NO. 8 is amino acids 39-202 of SEQ ID NO. 2, etc.). Amino acid residues Cys42-Cys75 of SEQ ID NO. 2 form the CRD1 domain of HVEM. Amino acid residues Cys78-Cys119 of SEQ ID NO. 2 form the CRD2 domain of HVEM. Amino acid residues Cys121-Cys162 of SEQ ID NO. 2 form the CRD3 domain of HVEM. The Examples section of this patent application describes experiments performed using some of such exemplary soluble HVEM ectodomain polypeptides.

TABLE 1

Sequences of Exemplary Soluble HVEM Ectodomain Polypeptides

| Soluble HVEM Ectodomain Polypeptide | Nucleotide Sequence | Amino Acid Sequence |
| --- | --- | --- |
| Gln29-Val202 | SEQ ID NO. 3 | SEQ ID NO. 4 |
| Pro37-Val202 | SEQ ID NO. 5 | SEQ ID NO. 6 |
| Leu39-Val202 | SEQ ID NO. 7 | SEQ ID NO. 8 |

In some embodiments the soluble HVEM ectodomain polypeptides of the invention comprise, or consist of, or consist essentially of, a CRD1 domain of an HVEM protein (e.g. amino acid residues Cys42-Cys75 of SEQ ID NO. 2, or amino acid residues that correspond thereto).

In some embodiments the soluble HVEM ectodomain polypeptides of the invention comprise, or consist of, or consist essentially of a CRD1 domain and a CRD2 domain of an HVEM protein (e.g. amino acid residues Cys42-Cys75 of SEQ ID NO. 2 and amino acid residues Cys78-Cys119 of SEQ ID NO. 2, or amino acid residues that correspond thereto).

In some embodiments the soluble HVEM ectodomain polypeptides of the invention comprise, or consist of, or consist essentially of a CRD1 domain, a CRD2domain, and a CDR3 domain of an HVEM protein (e.g. amino acid residues Cys42-Cys75 of SEQ ID NO. 2 and amino acid residues Cys78-Cys119 of SEQ ID NO. 2 and amino acid residues Cys121-Cys162 of SEQ ID NO. 2, or amino acid residues that correspond thereto).

In some embodiments the soluble HVEM ectodomain polypeptides of the invention do not comprise a CRD2 domain.

In some embodiments the soluble HVEM ectodomain polypeptides of the invention do not comprise a CRD3 domain.

In some embodiments the soluble HVEM ectodomain polypeptides of the invention do not comprise a CRD2 or CRD3 domain.

In some embodiments the soluble HVEM ectodomain polypeptides of the invention comprise, or consist of, or consist essentially of, the amino acid sequence of SEQ ID NO. 4, SEQ ID NO. 6, or SEQ ID NO. 8, or amino acid sequences that correspond thereto.

In some embodiments the soluble HVEM ectodomain polypeptides of the invention comprise, or consist of, or consist essentially of, an amino acid sequence starting at amino acid position 19, 20, 21, 22, 23, 24, 25, 26, 27, 28, 29, 30, 31, 32, 33, 34, 35, 36, 37, 38, 39,40, 41, or 42 of SEQ ID NO. 2, or amino acid residues that correspond thereto.

In some embodiments the soluble HVEM ectodomain polypeptides of the invention comprise, or consist of, or consist essentially of, an amino acid sequence starting at amino acid position 19, 20, 21, 22, 23, 24, 25, 26, 27, 28, 29, 30, 31, 32, 33, 34, 35, 36, 37, 38, 39,40, 41, or 42 of SEQ ID NO. 2, and ending at amino acid 75, 76, or 77 of SEQ ID NO. 2, or amino acid residues that correspond thereto (i.e. comprising a CDR1 domain).

In some embodiments the soluble HVEM ectodomain polypeptides of the invention comprise, or consist of, or consist essentially of, an amino acid sequence starting at amino acid position 19, 20, 21, 22, 23, 24, 25, 26, 27, 28, 29, 30, 31, 32, 33, 34, 35, 36, 37, 38, 39,40, 41, or 42 of SEQ ID NO. 2, and ending at amino acid 119 or 120 of SEQ ID NO. 2, or amino acid residues that correspond thereto (i.e. comprising a CRD1 and CRD2 domain).

In some embodiments the soluble HVEM ectodomain polypeptides of the invention comprise, or consist of, or consist essentially of, an amino acid sequence starting at amino acid position 19, 20, 21, 22, 23, 24, 25, 26, 27, 28, 29, 30, 31, 32, 33, 34, 35, 36, 37, 38, 39,40, 41, or 42 of SEQ ID NO. 2, and ending at amino acid 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201 202, 203, 204, 205, 206, 207, 208, or 209 of SEQ ID NO. 2, or amino acid residues that correspond thereto (i.e. comprising a CRD, CRD2, and CRD3 domain).

It should be noted that one of skill in the art can readily determine and/or identify amino acid positions in other sequences that "correspond" to any of the specific amino acid residues defined herein, regardless of whether those other sequences utilize a different numbering scheme or are present in a different HVEM sequences (such as in an HVEM sequence from a different species), for example by performing a sequence alignment to the sequence of SEQ ID NO. 2. It should also be noted that for all of the numbered sequences or numbered amino acid residues provided herein sequences and amino acid residues that "correspond" to such sequences/residues are also contemplated and encompassed herein.

Variants of any of the specific soluble HVEM ectodomain polypeptide sequences provided above and elsewhere in this patent disclosure are also contemplated and are intended to fall within the scope of the present invention. For example, in some embodiments variants of the specific sequences disclosed herein from other species (orthologs) may be used. Similarly, in other embodiments variants that comprise fragments of any of the specific sequences disclosed herein may be used. Likewise, in some embodiments variants of the specific sequences disclosed herein that comprise one or more amino acid substitutions, additions, deletions, or other mutations may be used. In some embodiments the variant amino acid sequences have at least about 40% or 50% or 60% or 65% or 70% or 75% or 80% or 85% or 90% or 95% or 98% or 99% identity with the specific soluble HVEM ectodomain polypeptides described herein. In all such cases, all variant soluble HVEM ectodomain polypeptides should comprise a CRD1 domain, or a portion thereof that is sufficient for binding to BTLA, and they should exhibit one or more of the following functional properties: HVEM activation, BTLA activation, inhibition of proliferation of BTLA$^+$ B-cell lymphoma cells, inhibition of growth of a BTLA$^+$ B-cell lymphoma, stimulation of the activity of CD8+ T-cells, inhibition of the activation of B-cell receptors in B-cell lymphoma cells, inhibition of secretion of IL-21 by follicular T helper (TFH) cells, inhibition of secretion of IL-21 by B-cell lymphoma cells, inhibition of BCR pathway activation, and inhibition of BTK, SYK, and/or ERK activation in BTLA$^+$ B-cell lymphoma cells. Suitable assays for assessing such functional properties are provided in the Examples section of this patent application.

It should be noted that all of the soluble HVEM ectodomain polypeptides contemplated by or described in the present patent disclosure may, in some embodiments, comprise a secretion signal sequence, or may be expressed via a precursor form that comprises a secretion signal sequence. In some embodiments an IgG Kappa secretion signal is used. In other embodiments an interleukin 2 (IL2) secretion signal is used. However, any suitable secretion signal sequence known in the art may be used.

In addition to providing amino acid sequences, the present invention also provides nucleic acid sequences. For example, in some embodiments the present invention provides nucleotide sequences that encode soluble HVEM ectodomain polypeptides, including, but not limited to, those that comprise, or consist of, or consist essentially of, the nucleotide sequences of SEQ ID NO. 3, SEQ IDNO. 5, or SEQ ID NO. 7. The present invention contemplates and provides nucleotide sequences that encode all of the soluble HVEM ectodomain polypeptides described herein—including those for which specific sequences are disclosed and the various variants of such sequences described herein. The present invention also provides DNA constructs (e.g. vectors and plasmids) comprising any of the nucleic acid molecules and/or nucleotide sequences described herein, or encoding any of the soluble HVEM ectodomain polypeptides described herein.

The present invention also provides genetically modified cells comprising any of the nucleic acid molecules and/or nucleotide sequences described herein, or encoding any of the soluble HVEM ectodomain polypeptides described herein.

It should be noted that, while the present invention is directed primarily to use of soluble HVEM ectodomain polypeptides, in some instances it may be possible to use insoluble (i.e. membrane-bound) proteins that comprise the sequences present in such soluble HVEM ectodomain polypeptides. For example, in those embodiments that involve CAR T-cells that express (and secrete) soluble HVEM ectodomain polypeptides, it may, in some instances, be possible to use a CAR T-cell that expresses an insoluble (i.e. membrane-bound) version of the HVEM ectodomain polypeptide, wherein rather than being secreted by the T-cell the HVEM ectodomain polypeptide sequences are membrane bound and are presented on the surface of the T-cell. Such embodiments are intended to fall within the scope of the present invention. Thus, unless stated otherwise, all of those embodiments of the present invention that involve a soluble HVEM ectodomain polypeptide can be performed using insoluble variants of such polypeptides that comprise the sequences present soluble HVEM ectodomain polypeptide as well as other sequences that result in presentation of such sequences in a cell membrane (e.g. on the surface of a cell).

3. Antibodies (Including Anti-Hvem and Anti-Btla Antibodies)

Several embodiments of the present invention involve antibodies. As used herein, the term "antibody" encompasses intact polyclonal antibodies, intact monoclonal antibodies, antibody fragments (such as Fab, Fab', F(ab')2, and Fv, and single chain Fv (scFv) fragments, single-domain antibodies (sdAb or nanobodies)), fusion proteins comprising an antigen determination portion of an antibody, bispecific antibodies generated from at least two intact antibodies, chimeric antibodies, humanized antibodies, human antibodies, and any other modified immunoglobulin molecule(s) comprising an antigen recognition site—so long as the antibodies comprise an antigen recognition site and exhibit the desired biological activity.

Various different types of antibody fragments, and methods of making and using such antibody fragments, are known in the art. See, for example, Fridy et al., Nature Methods. 2014 December;11(12):1253-60 (the contents of which are hereby incorporated by reference) for a description of the production of nanobody repertoires multi-specific antibodies. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well-known subunit structures and three-dimensional configurations. Antibodies can be naked, or conjugated to other molecules such as toxins, radioisotopes, or any of the other specific molecules recited herein.

In some embodiments the present invention involves antibodies against BTLA and/or antibodies against HVEM.

In some embodiments such antibodies may be any suitable type of anti-BTLA antibody or anti-HVEM antibody. In certain preferred embodiments an antibody fragment that binds to BTLA or HVEM is used. For example, in certain embodiments a Fab, Fab', F(ab')2, Fv, scFv, or sdAb (nanobody) fragment is used. In certain preferred embodiments the antibody fragment is a scFv fragment. In other preferred embodiments the antibody fragment is a nanobody. In certain embodiments such antibodies (including antibody fragments) bind to their respective target antigens (i.e. BTLA or HVEM) with high affinity and/or high specificity. In certain preferred embodiments such antibodies (including antibody fragments) both bind to and activate their respective target antigens (i.e. BTLA or HVEM) on the surface of B-cells—i.e. they act as agonists for their respective target antigens. For example such activating/agonist antibodies may mimic the biological activity of one or more natural ligands of their respective target antigens (i.e. BTLA or HVEM). Examples of antibodies (including antibody fragments) that are specific for BTLA are described in WO 2010106051 A1, and that are specific for HVEM are described in Park et al., Cancer Immunol. Immunother. 2012 February;61(2):203-14. However, any other suitable antibodies (including antibody fragments) may be used.

The term "humanized antibody" refers to an antibody derived from a non-human (e.g., murine) immunoglobulin, which has been engineered to contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, or hamster) that have the desired specificity, affinity, and capability (Jones et al., 1986, Nature, 321:522-525; Riechmann et al., 1988, Nature, 332:323-327; Verhoeyen et al., 1988, Science, 239:1534-1536). In some instances, the Fv framework region (FW) residues of a human immunoglobulin are replaced with the corresponding residues in an antibody from a non-human species that has the desired specificity, affinity, and capability.

Humanized antibodies can be further modified by the substitution of additional residues either in the Fv framework region and/or within the replaced non-human residues to refine and optimize antibody specificity, affinity, and/or capability. In general, humanized antibodies will comprise substantially all of at least one, and typically two or three, variable domains containing all or substantially all of the CDR regions that correspond to the non-human immunoglobulin whereas all or substantially all of the FR regions are those of a human immunoglobulin consensus sequence. Humanized antibody can also comprise at least a portion of an immunoglobulin constant region or domain (Fc), typically that of a human immunoglobulin. Examples of methods used to generate humanized antibodies are described in U.S. Pat. Nos. 5,225,539 or 5,639,641.

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more distinct sources, typically two or more distinct species. Typically, the variable region of both light and heavy chains corresponds to the variable region of antibodies derived from one species of mammals (e.g., mouse, rat, rabbit, etc.) with the desired specificity, affinity, and capability while the constant regions are homologous to the sequences in antibodies derived from another (usually human) to avoid eliciting an immune response in that species.

A "monoclonal antibody" (mAb) refers to a homogeneous antibody population involved in the highly specific recognition and binding of a single antigenic determinant, or epitope. This is in contrast to "polyclonal antibodies" that typically include different antibodies directed against different antigenic determinants.

Furthermore, "monoclonal antibody" refers to such antibodies made in any number of ways including, but not limited to, by hybridoma, phage selection, recombinant expression, and transgenic animals.

In particular, monoclonal antibodies can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g. radioimmunoassay (RIA); enzyme-linked immunosorbent assay (ELISA)) can then be propagated either in in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid.

Alternatively, monoclonal antibodies can be made using recombinant DNA methods, as described in U.S. Pat. No. 4,816,567. The polynucleotides encoding a monoclonal antibody are isolated from mature B-cells or hybridoma cells, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant monoclonal antibodies or antigen-binding fragments thereof of the desired species can be isolated from phage display libraries expressing CDRs of the desired species as described (McCafferty et al., 1990, Nature, 348:552-554; Clackson et al., 1991, Nature, 352:624-628; and Marks et al., 1991, J. Mol. Biol., 222:581-597).

Polyclonal antibodies can be produced by various procedures well known in the art. For example, a host animal such as a rabbit, mouse, rat, etc. can be immunized by injection with an antigen to induce the production of sera containing polyclonal antibodies specific for the antigen. The antigen can include a natural, synthesized, or expressed protein, or a derivative (e.g., fragment) thereof. Various adjuvants may be used to increase the immunological response, depending on the host species, and include, but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art. Antibodies can be purified from the host's serum.

4. Compositions & Methods Involving Car T Cells

Cancer immunotherapy involves engineering patients' own immune cells to recognize and attack their tumors—an approach that is frequently referred to as adoptive cell transfer (ACT). Such methods have yielded promising results in clinical trials so far, including those for treatment of lymphoma. In ACT T cells collected from a patient's own blood are genetically engineered to produce recombinant receptors on their surface called chimeric antigen receptors or "CARs." CARs contain an antigen-binding domain designed to recognize and bind to a specific cell surface antigen on the patient's tumor cells. The engineered. CAR T cells are expanded in vitro and then infused into the patient. After the infusion, the cells multiply in the patient's body and can recognize and kill cancer cells in the patient that express the cell surface antigen. There are several CAR T cell clinical trials ongoing, including several for lymphoma. Several of the lymphoma trials involve the use of CAR cells expressing a CAR designed to bind to the antigen CD19 (i.e. CD19-specific CARs)—as CD19 is frequently expressed on the surface of lymphoma. cells. There are also lymphoma trials ongoing that utilize CD20-specific, CD22-specific, or CD30-specific CAR T cells. See Brentjens, Riviere et al. 2011, Brentjens, Davila et al. 2013, Sadelain 2015, Jackson, Rafiq et al. 2016, Ramos, Heslop et al. 2016 for additional description regarding CAR cell therapy and clinical trials, including CD19- CAR T cell therapy for lymphoma. The contents of each of these references are hereby incorporated by reference in their entireties.

Several of the embodiments of the present invention involve CARs, CAR T cells, and CAR T cell therapy/ACT for the treatment of lymphoma. For example, in some embodiments the present invention provides vectors and nucleotide sequences that comprise both CAR-encoding nucleotide sequences and nucleotide sequences that encode soluble HVEM ectodomain polypeptides. Similarly, in other embodiments the present invention provides vectors and nucleotide sequences that comprise both CAR-encoding nucleotide sequences and nucleotide sequences that encode antibodies (such as antibody fragments) that bind to HVEM or BTLA. Transduction of T-cells with such vectors result in the production of CAR T cells that express the desired chimeric antigen receptor and also express—and secrete—the desired active agents described herein (e.g. soluble HVEM ectodomain polypeptides, HVEM antibodies, or BTLA antibodies). In some embodiments the present invention provides CAR T cells that express both a CAR and a soluble HVEM ectodomain polypeptide, whether following transduction with one of the specific modified vectors described herein that contain CAR and HVEM sequences within the same nucleic acid molecule, or following transduction with separate CAR-encoding and soluble HVEM ectodomain polypeptide-encoding nucleic acid molecules/vectors). Similarly, in some embodiments the present invention provides CAR T cells that express both a CAR and an HVEM antibody or a BTLA antibody, whether following transduction with one of the specific modified vectors described herein that contain CAR and antibody sequences within the same nucleic acid molecule, or following transduction with separate CAR-encoding and antibody-encoding nucleic acid molecules/vectors). The present invention also provides methods of treatment that utilize such CAR T cells. In such embodiments the CAR can be one that binds to any suitable cell surface receptor expressed on the surface of the cells of interest, i.e. B-cell lymphoma cells, including BTLA+/hi B-cell lymphoma cells. For example, in some embodiments the CAR may be a CD19-specific CAR, a CD20-specific CAR, a CD22-specific CAR, a CD30-specific CAR, an Igk-specific, a ROR1-specific CAR, or a CAR that binds to any other suitable cell surface receptor.

Methods of making and using CARs and CAR T cells are known in the art, and the compositions and methods of the present invention can be made and used with reference to the existing literature regarding CAR T-cell generation and use—including that literature that teaches how to generate and use CD19-specific CAR T cells. For example, reference is made herein to the following references—the entire contents of which are hereby incorporated by reference: (Brentjens, Santos et al. 2007, Pegram, Purdon et al. 2015). The present invention provides certain modifications of current CAR T cell schemes, including known CD19-specific CAR T cell schemes. For example the compositions and methods of the present invention can be used to enable the targeted treatment of B-cell lymphomas with a soluble HVEM ectodomain polypeptide that is secreted from CAR T cells. A schematic illustration of this approach is provided in FIG. 25—where CD19-specific CARs are shown as an example. Similarly, the compositions and methods of the present invention can be used to enable the targeted treatment of B-cell lymphomas with an anti-HVEM or anti-BTLA antibody that is secreted from CAR T cells. This could be achieved, for example, by replacing the soluble HVEM ectodomain polypeptide sequences shown the schematic of FIG. 25 with sequences that encode an anti-HVEM or anti-BTLA antibody.

Figure 25A:
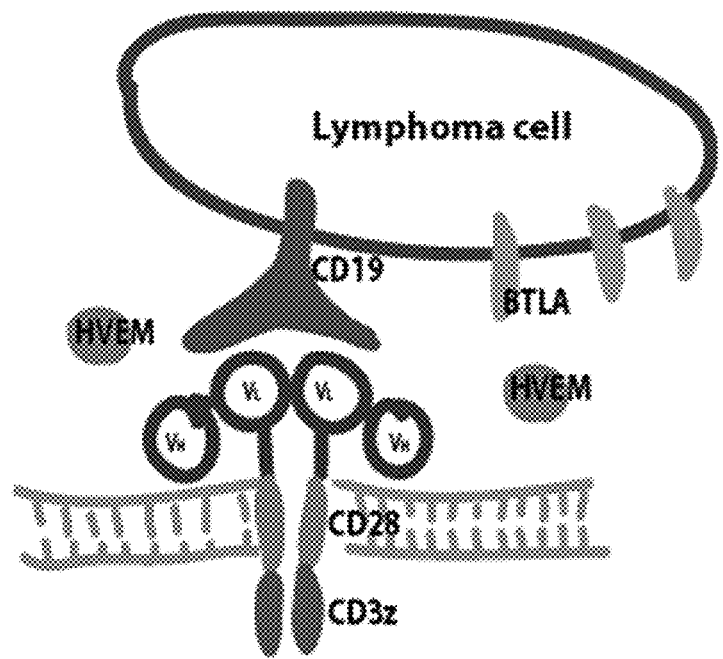
FIG. 25A-B.

In one embodiment the present invention provides certain novel vectors for CAR T cell generation. In one embodiment the present invention provides a nucleic acid molecule comprising: (a) a nucleotide sequence encoding a chimeric antigen receptor (CAR), and (b) a nucleotide sequence encoding a soluble HVEM ectodomain polypeptide. In another embodiment the present invention provides a nucleic acid molecule comprising: (a) a nucleotide sequence encoding a chimeric antigen receptor (CAR), and (b) a nucleotide sequence encoding an anti-HVEM antibody or an anti-BTLA antibody. In some such embodiments the nucleic acid molecule of also optionally comprises a nucleotide sequence encoding a reporter protein, such as green fluorescent protein (GFP). The nucleotide sequence encoding the chimeric antigen receptor (CAR) can be any suitable sequence that encodes a CAR of the desired specificity that is known in the art. For example, in one embodiment the sequence may be that from a SFG-1928z vector encoding a CD19-specific CAR. Such SFG-1928z vectors are known the in art. See, for example, the disclosure of WO 2014134165, the contents of which are hereby incorporated by reference. However, sequences of other CD19-specific CARs, and CARs having different specificities, are known in the art and can be used herein. The nucleotide sequence encoding the soluble HVEM ectodomain polypeptide can be any nucleotide sequence that encodes a soluble HVEM ectodomain polypeptide—as described and defined herein. The nucleotide sequences encoding the anti-HVEM or anti-BTLA antibodies can be any suitable nucleotide sequence— for example as further described and defined herein. In preferred embodiments a secretion signal is included upstream of the nucleotide sequence encoding the soluble HVEM ectodomain polypeptide or the nucleotide sequence encoding the antibodies. The arrangement of the CAR-encoding nucleotide sequence relative to the nucleotide sequence encoding the soluble HVEM ectodomain polypeptide (or the anti-HVEM or anti-BTLA antibody) in the nucleic acid molecule/vector can be varied. FIG. 25 provides one exemplary arrangement for expression of a soluble HVEM ectodomain polypeptide. However, other arrangements that enable expression of both the CAR molecule and the soluble HVEM ectodomain polypeptide (or the anti-HVEM or anti-BTLA antibody) from the same vector can be employed—for example using internal ribosome entry sites, proteolytic cleavage sites, or any other suitable means. In some embodiments, including that shown in FIG. 25, the soluble HVEM ectodomain polypeptide is initially expressed as a GFP fusion, and the GFP and HVEM components are then proteolytically cleaved—for example as a result of inclusion of a P2A proteolytic cleavage/recognition sequence. This enables GFP expression to be used as surrogate to monitor expression of the soluble HVEM ectodomain polypeptide. In some embodiments different expression reporters/markers may be used in place of GFP. Alternatively, in other embodiments an expression reporter need not be used.

5. Non CAR T Cell-Based Compositions and Methods for Targeted Delivery

In some embodiments the present invention provides certain non-CAR-based compositions and methods useful for the targeted delivery of the active agents described herein (such as soluble HVEM ectodomain polypeptides and anti-HVEM or anti-BTLA antibodies) to lymphoma cells. Such compositions and methods involve using a suitable "targeting agent" that can bind to a molecule expressed on, or in the vicinity of, lymphoma cells, e.g. in a subject's tumor. In some such embodiments the targeting agent may be an antibody, or antigen-binding domain of an antibody. For example, in some embodiments the present invention provides a composition that comprises both (a) a soluble HVEM ectodomain polypeptide (or an anti-HVEM or anti-BTLA antibody), and (b) an antibody, or antigen-binding domain thereof that is specific for a cell surface antigen on a B-cell lymphoma cell (for example a BTLA$^+$ lymphoma cell). In some such embodiments the composition is, or comprises, a fusion protein wherein the fusion protein comprises both (a) a soluble HVEM ectodomain polypeptide (or an anti-HVEM or anti-BTLA antibody), and (b) an antibody, or antigen-binding domain thereof that is specific for a cell surface antigen on a B-cell lymphoma cell (for example a BTLA$^+$ lymphoma cell). However, in other embodiments that composition may comprise both components separately, such as in a nanoparticle, a liposome, a polymeric micelle, a lipoprotein-based drug carrier, a dendrimer, or in any other suitable vehicle by which the antibody component of the composition can be used to deliver the active agent specifically to the desired lymphoma cells. In some embodiments the cell surface antigen may be selected from the group consisting of CD19, CD20, CD22, CD30, BTLA, Igk, and ROR1. In some embodiments the targeting agent may be rituximab (a CD20-specific antibody), or the antigen-binding domain thereof

6. Methods of Treatment

Several of the embodiments of the present invention involve methods of treatment. As used herein, the terms "treat," "treating," and "treatment," refer to therapeutic measures that result in a detectable improvement in one or more clinical indicators or symptoms of a B-cell lymphoma in a subject. For example, such terms encompass either transiently or permanently improving, alleviating, abating, ameliorating, relieving, reducing, inhibiting, preventing, or slowing at least one clinical indicator or symptom, preventing additional clinical indicators or symptoms, reducing or slowing the progression of one or more clinical indicators or symptoms, causing regression of one or more clinical indicators or symptoms, and the like. For example, "treating" a B-cell lymphoma according to the present invention includes, but is not limited to, reducing the rate of growth of B-cell lymphoma (or of B-cell lymphoma cells), halting the growth of a B-cell lymphoma (or of B-cell lymphoma cells), causing regression of a B-cell lymphoma (or of B-cell lymphoma cells), reducing the size of a B-cell lymphoma tumor (for example as measured in terms of tumor volume or tumor mass), reducing the grade of a B-cell lymphoma tumor, eliminating a B-cell lymphoma tumor (or B-cell lymphoma tumor cells), preventing, delaying, or slowing recurrence (rebound) of a B-cell lymphoma tumor, improving symptoms associated with a B-cell lymphoma, improving survival timed for a B-cell lymphoma patient, inhibiting or reducing spreading of a B-cell lymphoma (e.g. metastases), and the like. Similarly, "treating" a B-cell lymphoma can include, but is not limited to, reducing activation of B-cell receptors, reducing activity of IL-21-secreting follicular T helper cells, and/or increasing activity of CD8+ T-cells, in a patient's tumor.

In some embodiments the methods of treatment described herein may be performed in combination with other methods of treatment useful for the treatment of B-cell lymphomas, including, but not limited to, administration of other agents (including, but not limited to, DNA damaging agents, an anti-CD20 antibody, rituximab, ibrutinib, cyclophosphamide, doxorubicin, vincristine, prednisone, and idelalisib), surgical methods (e.g. for tumor resection), radiation therapy methods, treatment with chemotherapeutic agents, radiation therapy, immunotherapy, adoptive cell transfer (ACT), targeted delivery of EphA7 tumor suppressor proteins, treatment with an or any other suitable method. Similarly, in certain embodiments the methods of treatment provided herein may be employed together with procedures used to monitor disease status/progression, such as biopsy methods and diagnostic methods (e.g. MM methods or other imaging methods).

6.1 Subjects

The terms "subject," "individual," and "patient"—which are used interchangeably herein, are intended to refer to any subject, preferably a mammalian subject, and more preferably still a human subject, for whom diagnosis, prognosis, or therapy is desired. Mammalian subjects include humans, domestic animals, farm animals, sports animals, and zoo animals including, e.g., humans, non-human primates, dogs, cats, mice, rats, guinea pigs, and the like.

In most of the embodiments of the present invention the subject has, or is suspected of having, a B-cell lymphoma. In some such embodiments the B-cell lymphoma is follicular lymphoma (FL). In other embodiments the B-cell lymphoma is diffuse large B-cell lymphoma (DLBCL).

In some embodiments the subject has a B-cell lymphoma that is, or has a B-cell lymphoma that comprises lymphoma cells that are, BTLA$^+$ (i.e. that express detectable levels of BTLA) or BTLA (i.e. that express high levels of BTLA). In some embodiments the subject has a B-cell lymphoma that is not BTLA- or has a B-cell lymphoma that comprises lymphoma cells that are not BTLA- (i.e. that do not express detectable levels of BTLA).

In some embodiments the subject has a B-cell lymphoma that is, or has a B-cell lymphoma that comprises lymphoma cells that are, HVEM- (i.e. that do not express detectable levels of HVEM), or HVEMlo (i.e. that express low levels of HVEM), or that comprise one or more HVEM mutations, such as mutations that inhibit or prevent the normal tumor suppressor function of HVEM or that are associated with poor outcomes in B-cell lymphoma patients. Many such HVEM mutations are known in the art.

6.2 Administration Routes

The various different "active agents" provided herein can be administered to a subject via any suitable route, including by systemic administration or by local administration. "Systemic administration" means that the active agent is administered such that it enters the circulatory system, for example, via enteral, parenteral, inhalational, or transdermal routes. Enteral routes of administration involve the gastrointestinal tract and include, without limitation, oral, sublingual, buccal, and rectal delivery. Parenteral routes of administration involve routes other than the gastrointestinal tract and include, without limitation, intravenous, intramuscular, intraperitoneal, intrathecal, and subcutaneous. Preferably parenteral administration is used. More preferably still, intravenous parenteral administration is used. "Local administration" means that a pharmaceutical composition is administered directly to where its action is desired (e.g., at or near the site of a B-cell lymphoma), for example via direct intratumoral injection. It is within the skill of one of ordinary skill in the art to select an appropriate route of administration taking into account the nature of the specific active agent being used and nature of the specific B-cell lymphoma to be treated.

6.3 Effective Amounts

An "effective amount" of any active agent, composition, or pharmaceutical composition disclosed herein is an amount sufficient to sufficient to achieve, or contribute towards achieving, one or more outcomes described in the "treatment" definition above. An appropriate "effective" amount in any individual case may be determined using standard techniques known in the art, such as dose escalation studies, and may be determined taking into account such factors as the nature of the active agent, the desired route of administration, the desired frequency of dosing, the specific B-cell lymphoma being treated, the subjects, age, sex, and/or weight, etc. Furthermore, an "effective amount" may be determined in the context of any other treatment to be used. For example, in those situations where an active agent as described herein is to be administered or used in conjunction with other treatment methods or other agents, then the effective amount may be less than it would be where no such additional treatment method is used.

7. Methods for Determining Whether a Subject is a Candidate for Treatment

In some embodiments the present invention provides methods for determining whether a subject is a candidate for treatment using any of the compositions or methods provided herein. In some embodiments such methods involve determining or measuring or detecting decreased or absent expression or activity of HVEM, or presence of HVEM mutations, in a B-cell lymphoma or in B-cell lymphoma cells of the subject, whereby if the subject's B-cell lymphoma or B-cell lymphoma cells express decreased or absent expression or activity of HVEM, or presence of HVEM mutations, then the subject may be a candidate for treatment. Similarly in other embodiments such methods involve determining or measuring or detecting expression of, or high levels of expression of, BTLA in a B-cell lymphoma or in B-cell lymphoma cells of the subject, whereby if the subject's B-cell lymphoma or B-cell lymphoma cells express detectable levels of BTLA (i.e. are $BTLA^+$) or express high levels of BTLA (i.e. are $BTLA^{hi}$) then the subject may be a candidate for treatment. Furthermore, in other embodiments such methods involve a combination of these two approaches—i.e. determining or measuring or detecting both (a) decreased or absent expression or activity of HVEM, or presence of HVEM mutations, and (b) expression of, or high levels of expression of, BTLA in a B-cell lymphoma or in B-cell lymphoma cells of the subject.

8. Compositions

Several of the embodiments of the present invention involve compositions, for example pharmaceutical compositions. The term "composition" refers to a composition comprising at least one of the "active agents" described herein, and one or more additional components—such as diluents, buffers, saline (such as phosphate buffered saline), cell culture media, and the like. Where such "compositions" are "pharmaceutical compositions" the one or more additional components must be components that are suitable for delivery to a living subject, such as diluents, buffers, saline (such as phosphate buffered saline), carriers, stabilizers, dispersing agents, suspending agents, and the like.

The term "pharmaceutical composition" refers to a preparation that is in such form as to permit the biological activity of the active ingredient to be effective, and which contains no additional components that are unacceptably toxic to a subject to which the composition would be administered. Pharmaceutical compositions can be in numerous dosage forms, for example, tablet, capsule, liquid, solution, soft-gel, suspension, emulsion, syrup, elixir, tincture, film, powder, hydrogel, ointment, paste, cream, lotion, gel, mousse, foam, lacquer, spray, aerosol, inhaler, nebulizer, ophthalmic drops, patch, suppository, and/or enema. Pharmaceutical compositions typically comprise a pharmaceutically acceptable carrier, and can comprise one or more of a buffer (e.g. acetate, phosphate or citrate buffer), a surfactant (e.g. polysorbate), a stabilizing agent (e.g. human albumin), a preservative (e.g. benzyl alcohol), a penetration enhancer, an absorption promoter to enhance bioavailability and/or other conventional solubilizing or dispersing agents. Choice of dosage form and excipients depends upon the active agent to be delivered and the disease or disorder to be treated or prevented, and is routine to one of ordinary skill in the art.

EXAMPLES

The invention is further described in the following non-limiting Examples. Numbers in parentheses in these Examples refer to the numbered references in the reference list that follows this Examples section.

Example 1

Role of HVEM Inactivation in B Cell Lymphomas, and In Vitro and In Vivo Effects of Treatment with Soluble HVEM Polypeptides The results presented in this Example demonstrate that the HVEM-BTLA interaction has a tumor suppressive function in B-cell lymphomas, and, importantly, demonstrate that administration of a soluble HVEM ectodomain protein reverses these effects and blocks lymphoma growth in vivo.

Unless specifically stated otherwise any reference to "solHVEM" in Example 1 or in FIG. 1-14, refers to the Leu39-Val202 soluble HVEM ectodomain polypeptide of SEQ ID NO. 8 (as encoded by the nucleotide sequence of SEQ ID NO. 7).

The germinal center (GC) microenvironment has been implicated in the pathogenesis of B cell lymphomas. However, a precise mechanism linking the genetic pathogenesis of lymphoma and the microenvironment has not been defined. The HVEM (TNFRSF14) receptor gene is among the most frequently mutated genes in GC lymphomas. Loss of HVEM leads to the cell autonomous activation of proliferation signals and drives the development of GC lymphomas in vivo. In addition, HVEM deficient lymphoma B cells shape a tumor permissive microenvironment marked by an exacerbated lymphoid stroma activation and increased recruitment of T follicular helper (TFH) cells. Most of these changes result from disruption of inhibitory cell-cell interactions between HVEM and the BTLA (B and T Lymphocyte Attenuator) receptors. Importantly, it has now been found that exogenous administration of an HVEM ectodomain protein fragment (either solHVEM L39-V202 or P37-V202) impairs proliferative signals, normalizes cytokine production, and blocks lymphoma growth in vivo. Hence, loss of HVEM promotes lymphoma development through dual effects on B cells and their microenvironment that are directly amendable to exogenous intervention.

Introduction & Background for Example 1

Most human lymphomas arise from germinal center (GC) B-cells. These include diffuse large B cell lymphomas (DLBCL) and follicular lymphomas (FL) which continue to pose a significant health challenge. Recent genomic studies have yielded important new insight into lymphoma pathogenesis and have catalogued recurrent genomic lesions (Challa-Malladi et al., 2011; Cheung et al., 2010; Lohr et al., 2012; Morin et al., 2011; Okosun et al., 2014; Oricchio et al., 2011; Pasqualucci et al., 2014). In addition, the germinal center (GC) microenvironment has been discussed as a key factor in lymphoma development (Ame-Thomas et al., 2007; Amin et al., 2015; Mourcin et al., 2012; Pangault et al., 2010). However, precise mechanisms linking the GC microenvironment to the emergence of GC lymphomas are unknown.

The GC microenvironment is critical for most aspects of B cell function and likely contributes to lymphoma development and maintenance. GCs are dynamic structures that are composed of multiple hematopoietic and stromal cell types (Chang and Turley, 2015; De Silva and Klein, 2015). For example, the main lymphoid stromal cell subtypes, fibroblastic reticular cells (FRCs) and follicular dendritic cells (FDCs), contribute to B-cell recruitment, survival, and differentiation (Aguzzi et al., 2014; Fletcher et al., 2015). In turn, activated B cells produce TNF family cytokines TNFa and LTa1b2 that stimulate FRCs and FDCs (Roozendaal and Mebius, 2011). CXCL13 derived from these stromal cells is the major attractant for TFH cells that in turn support B cells through CD40L and secretion of cytokines IL-4 and IL-21 (Crotty, 2014). Notably, follicular lymphoma (FL) B cells retain a strong dependence on the GC microenvironment, which is thought to form a permissive niche for lymphomagenesis as a result of the crosstalk with malignant B cells (Ame-Thomas and Tarte, 2014; Mourcin et al., 2012; Rehm et al., 2011).

Cancer specific gene alternations can shed light on the underlying tumor biology. For example, somatic mutations in the HVEM (Herpes Virus Entry Mediator; TNFRSF14) receptor gene are among the most frequent genetic lesions in GC lymphomas and have been variably associated with prognosis (Cheung et al., 2010; Launay et al., 2012; Lohr et al., 2012). Exactly how HVEM mutations contribute to the biology of GC lymphomas is not known.

Studies of the HVEM receptor in T lymphocytes inform our current knowledge of this receptor's function. In T lymphocytes HVEM engages in stimulating cell-cell interactions by binding to LIGHT or CD160 receptors, whereas HVEM binding to the BTLA receptor (B and T Lymphocyte Attenuator) results in an inhibitory signal (Bjordahl et al., 2013; Cai and Freeman, 2009; Pasero et al., 2012; Steinberg et al., 2011). Expression of HVEM and its partner receptors is lineage restricted. For example, normal B cells variably express HVEM and BTLA depending on their differentiation and activation stage but they lack LIGHT and CD160, whereas follicular T helper (TFH) cells are characterized by their high BTLA expression (M'Hidi et al., 2009; Murphy et al., 2006)

The studies presented herein examine the function of HVEM in GC lymphomagenesis using a genetically and pathologically accurate mouse model. Furthermore, the studies presented herein also demonstrate that a soluble form of the HVEM receptor (solHVEM Leu39-Val202) can repair the effects of HVEM loss in lymphoma.

Results

Unless specifically stated otherwise any reference to "solHVEM" in Example 1 refers to the Leu39-Val202 soluble HVEM ectodomain polypeptide of SEQ ID NO. 8 (as encoded by the nucleotide sequence of SEQ ID NO. 7).

The interaction between the HVEM and BTLA receptors is lost in most human FLs

Figures 8A, 8B, 8C, 8D, 8E, 8F, 8G:
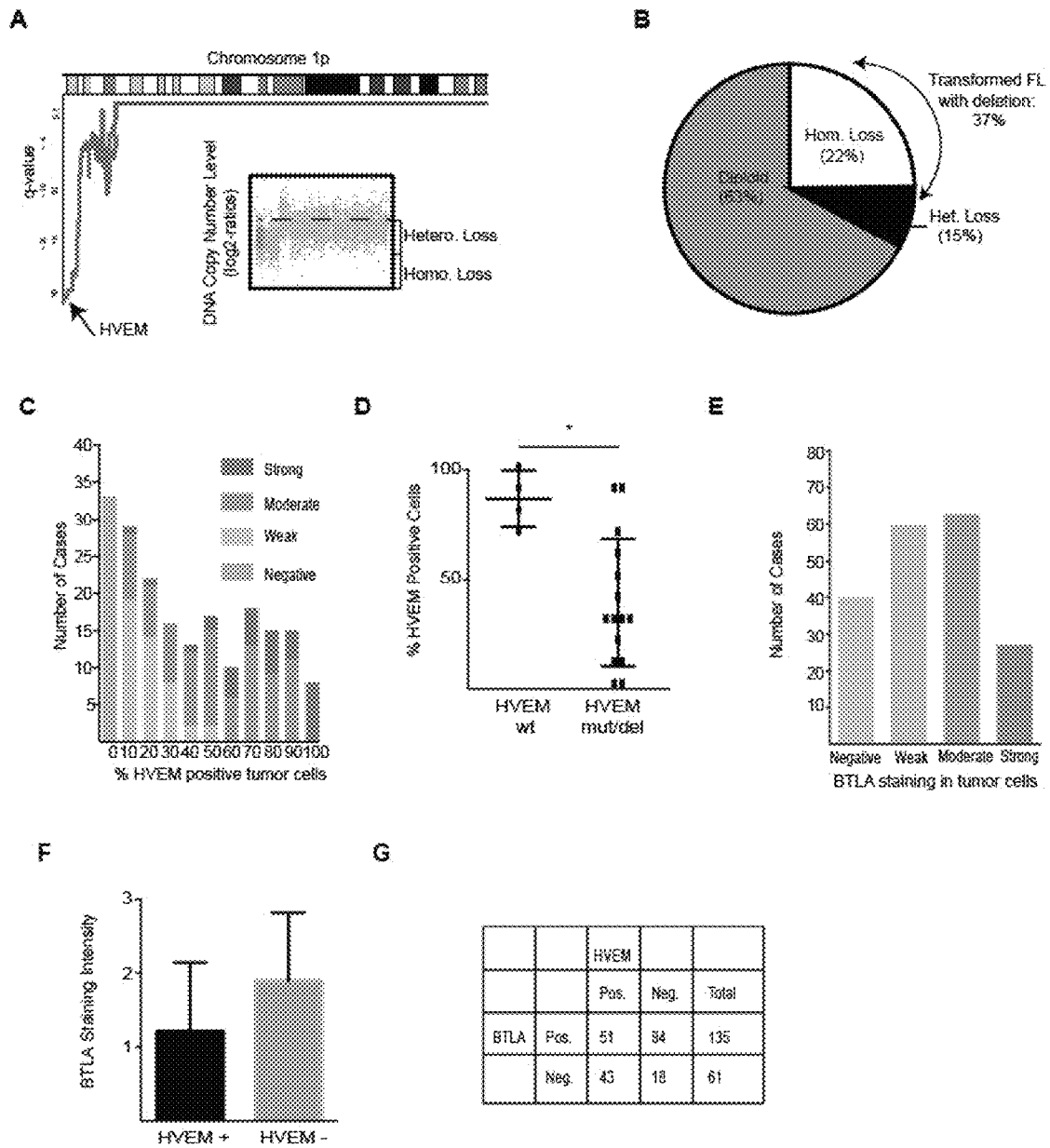
FIG. 8A-G. HVEM mutations and deletions in human lymphomas.

In a large collection (n=141) of human FLs it was found that HVEM mutations were present in 28% (n=40) of samples, and that one third (35%) of these were homozygous mutations (FIG. 1A-C)(Cheung et al., 2010; Launay et al., 2012; Lohr et al., 2012; Ross et al., 2007). HVEM mutations target the receptor's ectodomain and include missense (65%), nonsense (32.5%), and frame shift mutations (2.5%). Moreover, HVEM localizes to minimal common region of the chromosome 1p36 deletion—a region that is commonly lost across B cell malignancies (Cheung et al., 2010; Fitzgibbon et al., 2007). Meta-analysis of two separate series of array CGH data (MSKCC: n=64 (Oricchio et al., 2011); UNMC cohort: n=198 (Bouska et al., 2014)) shows that loss of the HVEM locus occurs in 34% of indolent FL samples (n=262), and 37% of transformed FLs (n=67) (FIG. 1D-F, FIGS. 8A and B). GISTIC (Genomic Identification of Significant Targets in Cancer) analysis indicates that 22-24% of these lesions are homozygous losses in both indolent and transformed samples (FIG. 1E and FIG. 8A). Hence, the genomic evidence indicates a powerful selection against the HVEM receptor gene during FL development.

In the present study HVEM protein expression in human FLs was examined. Tissue microarrays comprising 198 FL samples were evaluated for HVEM protein expression by immunohistochemistry. Samples were scored as HVEM positive when at least 20% of tumor cells showed specific staining. Using this cut-off, 62 samples (31.3%) were HVEM negative and 136 samples (68.7%) classified as HVEM positive (FIG. 1G, FIG. 8C). This proportion is consistent with the genomic data and reduced or absent protein expression was confirmed in HVEM mutated or deleted samples for samples (n=14) with available genomic and protein data (FIG. 8D).

BTLA is a known HVEM binding partner and the only HVEM receptor expressed on B cells (Murphy et al., 2006). Therefore BTLA expression was evaluated across the lymphoma tissue arrays. For a positive BTLA score (i.e. BTLA+) it was required that tumor cells showed a stronger stain than reactive GC B cells, which are weakly positive and were used as on-slide controls. Using this cut-off for BTLA, 102 samples were negative (51.2%) and 95 samples (48.2%) scored as positive (FIG. 1G, FIG. 8E). Together, 146 of 198 samples (74%) were negative for either HVEM or BTLA. Their association was tested using the chi-squared test and it was found that there was a significant negative (mutual exclusive) association such that HVEM positive tumors were more likely to lose BTLA than would be expected by chance (OR=0.254; 95% CI 0.126-0.511; p<0.0001) (FIG. 1G-I, FIGS. 8F and 1G). Mutations or deletions of BTLA were not observed and were most likely silenced transcriptionally. In this regard, it is noted that BTLA expression is controlled by the KMT2D (MLL2) methyltransferase in FL (Ortega-Molina et al., 2015). Hence, it appears that the interaction between HVEM and BTLA receptors is disrupted in the majority of human FLs, indicating that this is a potentially important tumor suppressor pathway.

HVEM acts as a tumor suppressor in a mouse model of follicular lymphoma

Figures 2A, 2B, 2C, 2D, 2E, 2F, 2G:
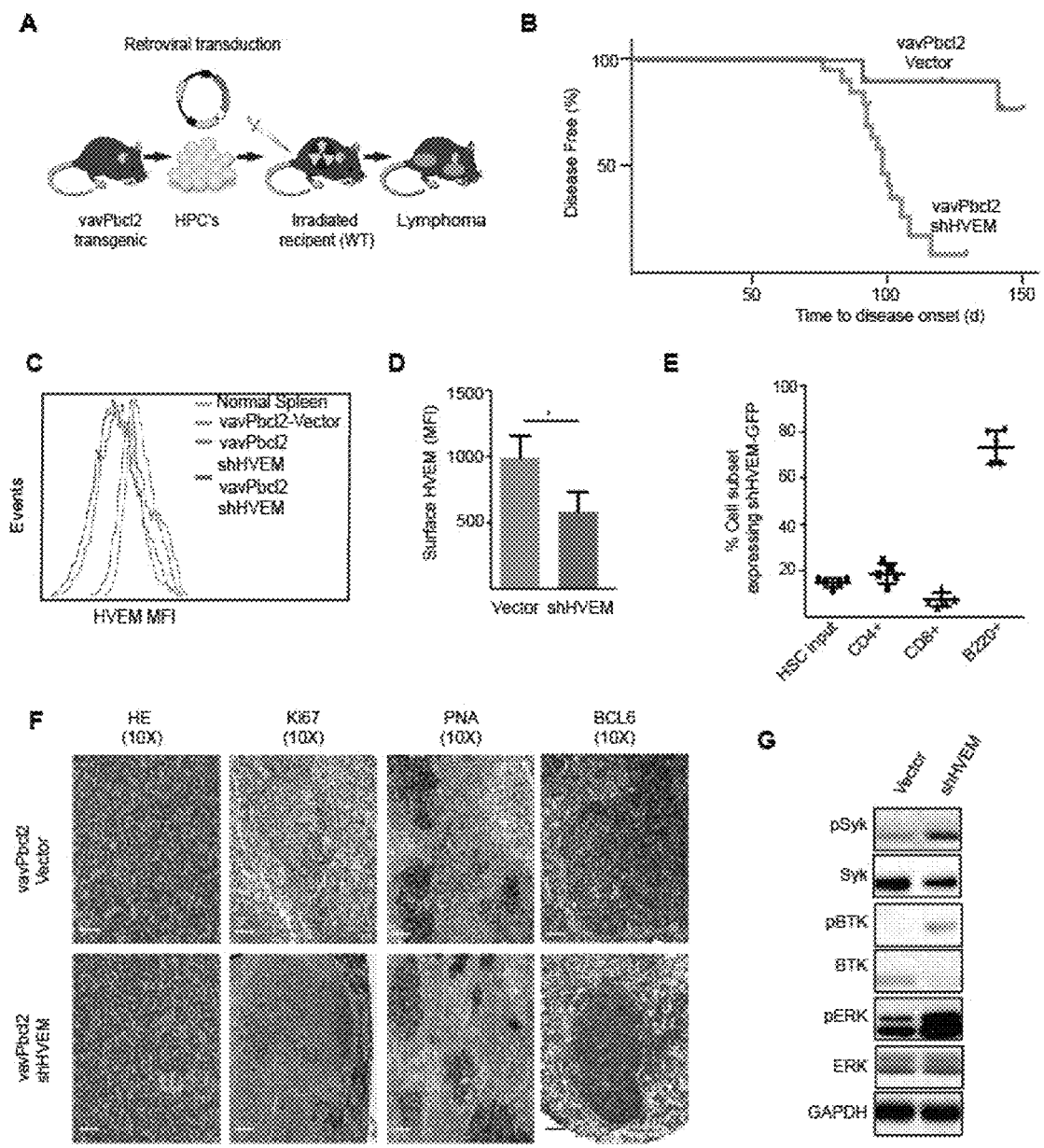
FIG. 2A, schematic representation of vavPBc12 mosaic mouse model.
FIG. 2B, Kaplan-Meier analysis of disease free survival (Vector, n=11; shRNA against HVEM, n=19)
FIG. 2C, FACS analysis for surface HVEM in B lymphocytes isolated from normal spleen, control lymphomas (vavPBc12-vector), and two independent lymphomas expressing the shRNA against HVEM (vavPBc12-shHVEM)
FIG. 2D, Quantification of HVEM FACS measurements (n=5 for each genotype, *p<0.01)
FIG. 2E, GFP expression of shHVEM in different mouse cell populations, HSCs (pre-injection into mouse), CD4+, CD8+, B220+(after sacking mouse) (n=5)
FIG. 2F, Pathology and immunohistochemistry for the indicated markers on murine lymphoma comparing control lymphoma (vavPBc12-vector) to HVEM deficient lymphomas (vavPBc12-HVEM), scale bars=100 µm.
FIG. 2G, Immunoblot on murine control lymphomas (vector) and HVEM deficient (HVEM) lymphomas probed as indicated.
Figures 9A, 9B, 9C, 9D, 9E:
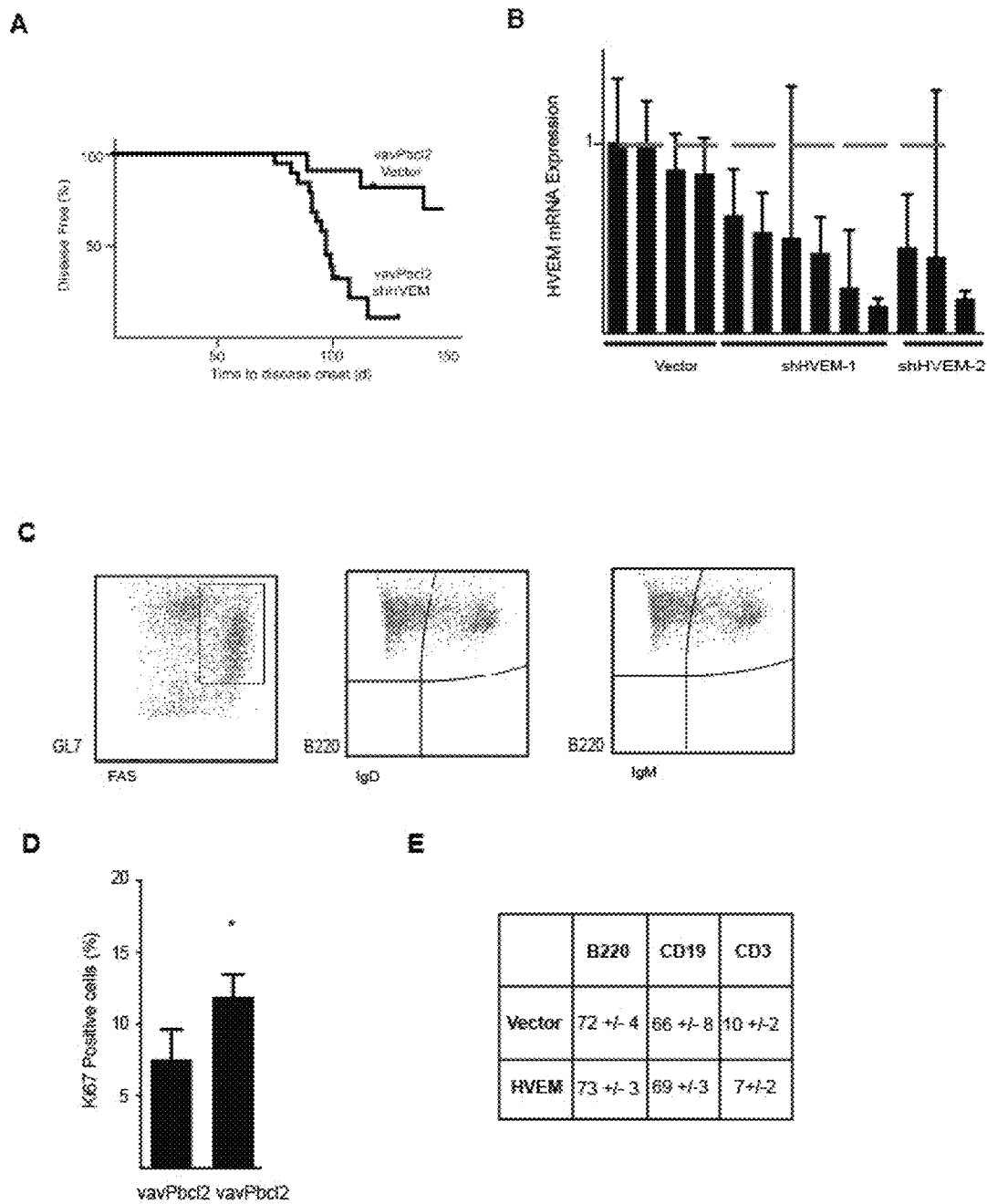
FIG. 9A-E. HVEM knockdown promotes FL development in vivo.

To elucidate the role of HVEM inactivation in FL development the vavPBc12 model that recapitulates key aspects of the genetics and pathology of human BCL2-positive FLs (Egle et al., 2004; Oricchio et al., 2011) was used. Briefly, vavPBc12 hematopoietic progenitor cells (HPCs) isolated from fetal livers were transduced with retroviruses expressing short hairpin RNAs (shRNAs) against HVEM or empty vector controls. These cells were then transplanted into lethally irradiated mice, and the recipients were monitored for lymphoma development (FIG. 2A). Knockdown of HVEM (red, n=19) caused a significant acceleration and increased penetrance of lymphoma development compared to controls (blue, n=11). Ninety percent of control animals remained tumor free for >100 days compared to only 10% of animals receiving the shHVEM (p<0.01) (FIG. 2B). These results were confirmed with a second shRNA against HVEM (FIG. 9A). Knockdown of the HVEM mRNA was also confirmed and decreased HVEM surface expression was observed by FACS (FIGS. 2C and D, FIG. 9B). To test whether the HVEM knockdown in the B cell compartment was responsible for lymphoma development, the expression of the shHVEM co-expressed with the GFP reporter was tracked from the initial HPC infection into the derived hematopoietic compartments. The initial transduction efficiency of the HPCs was ~15% and enrichment was found only in the FACS sorted lymphoma B cells—where over 80% expressed the shHVEM and GFP (FIG. 2E). Hence, these studies demonstrate that loss of HVEM leads to a B cell autonomous expansion and lymphoma development in vivo.

Pathological analysis of murine HVEM wild type and HVEM deficient lymphomas shows typical hallmarks of GC derived FLs. Typical follicular architecture, and expression of GC markers PNA, BCL6, and GL7, was found by immunohistochemistry and FACS analysis (FIG. 2F, FIG. 9C). Immunohistochemistry further showed increased Ki67 staining in HVEM deficient lymphomas consistent with increased proliferation and reduced latency (FIG. 9D). FACS analysis showed that all lymphomas were largely composed of small B220+ and CD19+B cells and HVEM deficient tumors showed a modest reduction in infiltrating CD3+ T cells (FIG. 9E). A detailed, deep sequencing-based B cell receptor (BCR) analysis further revealed an oligoclonal disease and associated repertoire bias, with somatic hypermutation (SHM) yielding intraclonal diversity. This likely reflected ongoing clonal evolution of a GC-driven disease (FIG. 10). A survey of signaling molecules further indicated activation and phosphorylation of signaling molecules related to the B cell receptor pathway (BCR) such as SYK, BTK, and also ERK activation in HVEM deficient compared to control lymphomas (FIG. 2G).

In human FL samples a mutually exclusive pattern of HVEM and BTLA expression was noticed. Studies in T cells have indicated that HVEM and BTLA can directly interact on the same cell—in cis (Cheung et al., 2009). These findings raise the possibility that loss of BTLA may similarly promote lymphoma development (FIG. 1G-I). Therefore, the effect of BTLA knockdown was tested in the same vavBcl2 mouse lymphoma model described above. Briefly, BTLA knockdown caused a significant acceleration of lymphoma development (n=11 vector, n=16 for BTLA, p<0.01) (FIGS. 3A and 3B). Tumor pathology revealed follicular structures, composition of predominant B220+ and CD19+B cells, and BTLA deficient lymphomas had higher Ki67 than controls and expressed the GC markers PNA and BCL6 (FIG. 3C-E). Similar to HVEM deficient lymphomas, activation of mitogenic signals such as increased ERK phosphorylation was observed by immunoblot (FIG. 3F). Hence, these studies demonstrate that loss of either HVEM or BTLA can cooperate with Bc12 and promote lymphoma development in vivo.

HVEM controls mitogenic signals in a cell autonomous and BTLA dependent manner

Figures 4A, 4B, 4C, 4D, 4E:
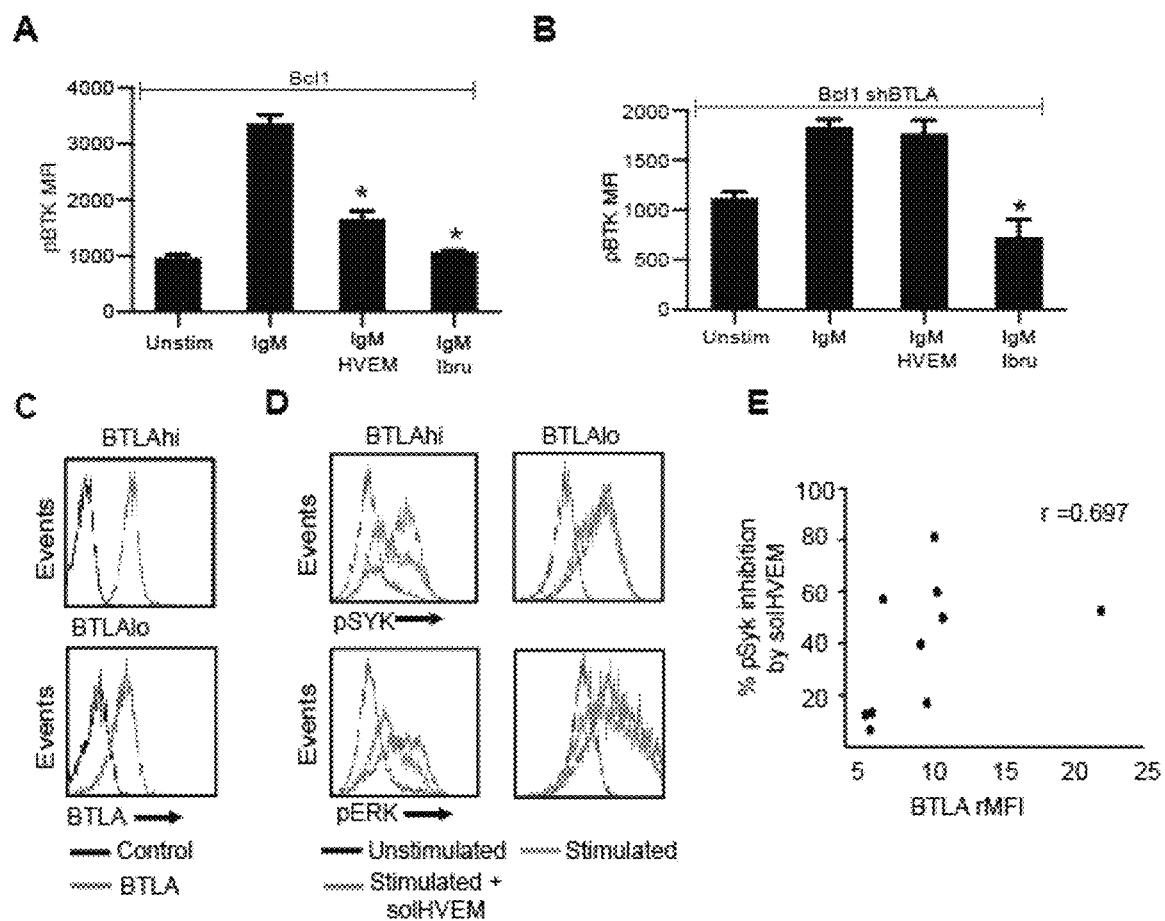
FIG. 4A-E. HVEM blocks BCR signaling in a cell autonomous and BTLA dependent manner.
Figure 11:
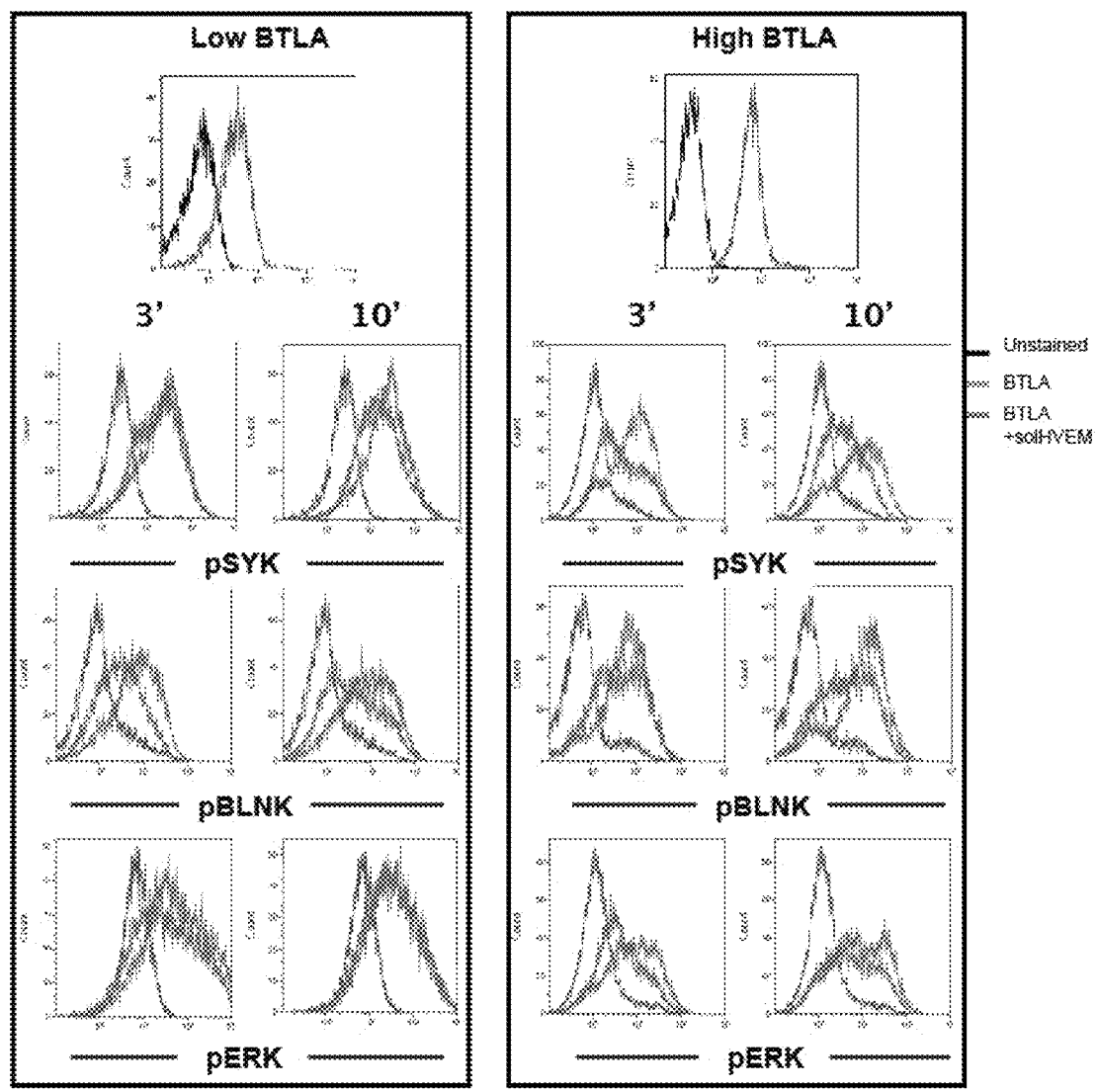
FIG. 11. Effect of HVEM on murine and human FL B cells. A FACS analysis of BTLA expression on purified human FL B cells distinguishes samples with high (BTLA$^{hi}$) and low (BTLAlo) surface BTLA expression (top); FACS analysis for the indicated signaling molecules in human primary FL B cells that were BTLA$^{hi}$ or BTLAlo and stimulated with anti-human IgG (3 min and 10 min; 10 μg/ml and $H_2O_2$ 1 mM) in the presence or absence of the soluble HVEM ectodomain (solHVEM; 10 μg/ml).

Loss of HVEM and BTLA leads to BCR activation in murine lymphomas (FIGS. 2G and 3F). Activation of the BCR signal could be a direct effect related to BTLA's ability to bind CD79 or alternatively it could be secondary to changes in local cytokine levels (Vendel et al., 2009). In order to directly test whether HVEM has a direct, cell autonomous, and BTLA-dependent effect on signaling, isolated lymphoma B cells were treated with a purified soluble HVEM ectodomain protein fragment (solHVEM: Leu39-Va1202) that retains HVEM's binding properties (Cheung et al., 2005; del Rio et al., 2010). Briefly, the BCR signaling pathway in BCL1 mouse lymphoma cells was stimulated with IgM in the presence or absence of solHVEM (10 µg/ml) or the pharmacological BTK inhibitor ibrutinib (10 nM) and BTK phosphorylation was measured as an indicator of BCR pathway activation by flow cytometry. The addition of solHVEM blocked BTK phosphorylation and activation similar to the pharmacological inhibitor (FIG. 4A). The ability of solHVEM to block the BCR signal transduction required BTLA and knockdown of BTLA prevented BTK inhibition in BCL1 cells (FIG. 4B). Similar observations were made in primary human FL B cells. BTLA expression was analyzed across ten samples of purified human FL B cells by FACS, and the samples were divided into BTLA" and BTLA[10] groups (FIG. 4C). The B cells were stimulated with anti-IgG in the presence or absence of solHVEM (10 µg/1111) and inhibition of SYK and ERK was observed in BTLA" cells whereas solHVEM had little effect in the BTLA[10] cells (FIG. 4D, FIG. 11). Cumulative analysis of all ten primary human FL B cells confirmed a significant relationship between the ability of solHVEM to block SYK phosphorylation and BTLA surface expression (r=0.697, p=0.03) (FIG. 4E).

HVEM Deficient Lymphomas have an Excessive Activation of the Tumor Stroma

Figures 5A, 5B, 5C, 5D, 5E, 5F, 5G, 5H, 5I:
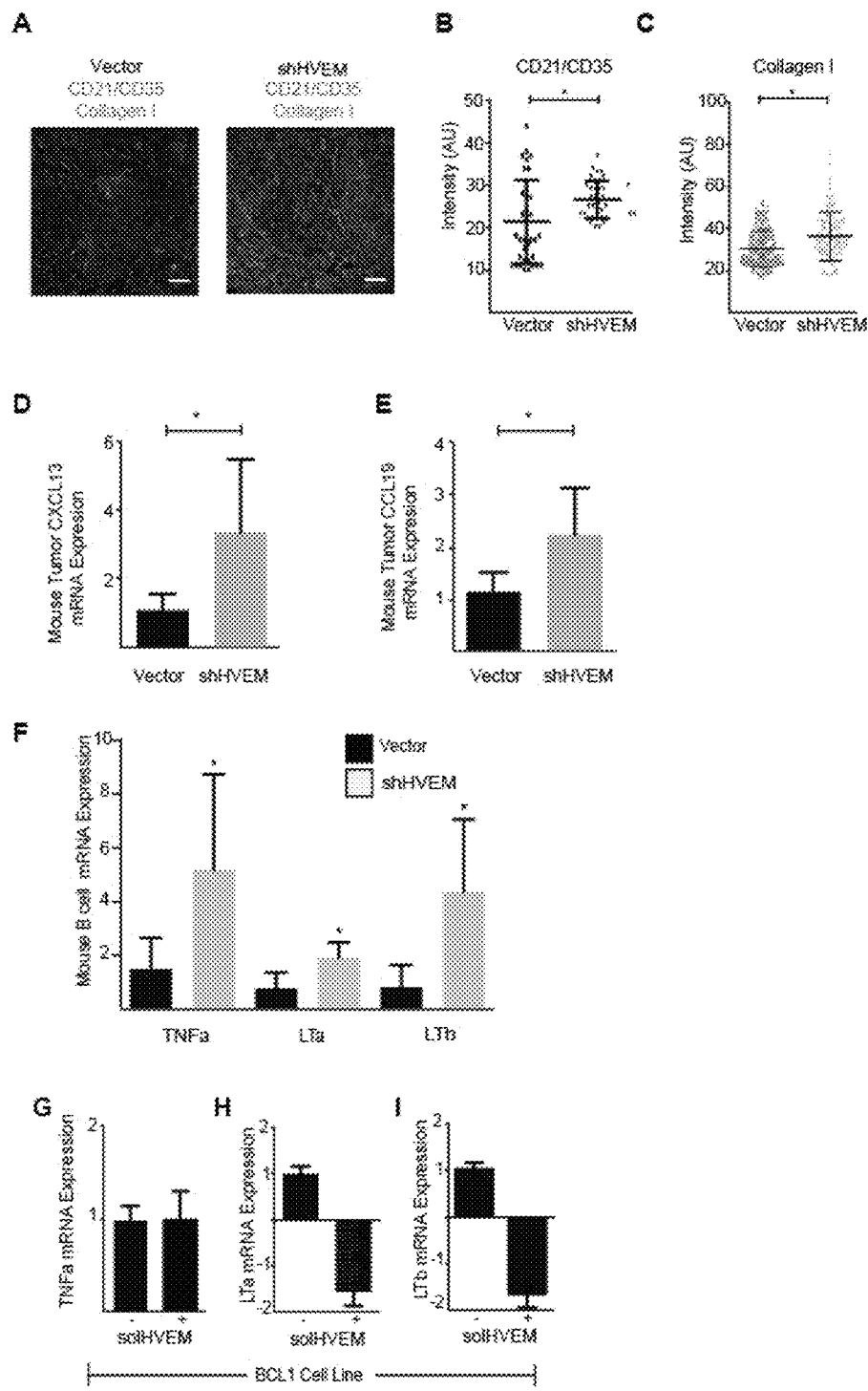
FIG. 5A-I. Abnormal activation of the lymphoid stroma in B-cell lymphomas.
Figures 12A, 12B, 12C, 12D, 12E, 12F:
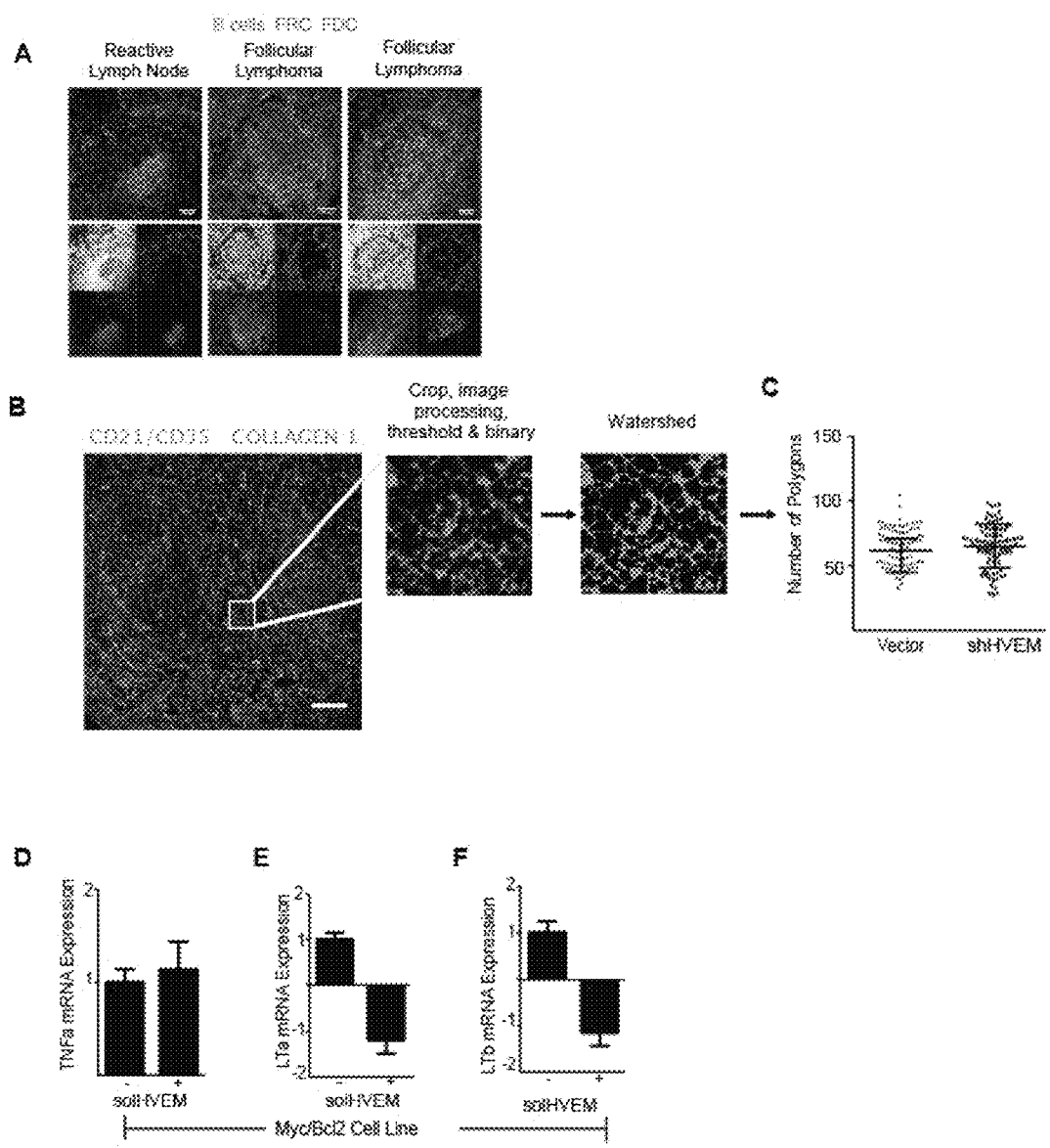
FIG. 12A-F. Analysis of the lymphoid stroma in B cell lymphomas.

In human FLs the malignant B cells are admixed with lymphoid stroma that provides support to the malignant B cells (Mourcin et al., 2012). These non-hematopoietic lymphoma components include in particular CD21Lpos follicular dendritic cells (FDCs) and transglutaminasepos fibroblast reticular cells (FRCs) (FIG. 12A). In the mouse lymphomas we observed an activation of the tumor stroma in the absence of any immunization and this was significantly more pronounced in the HVEM deficient lymphomas (FIG. 5A). Quantitative analysis of microscopic images showed a significant (p<0.05) increase of the CD21/CD35pos FDC network within follicles in HVEM deficient tumors compared to control tumors (n=3 for each) (FIG. 5B). Similarly, type I collagen density in perifollicular areas was significantly (p<0.05) increased in HVEM deficient lymphomas indicating activation of FRCs in the absence of a cellular expansion of ERTR7pos FRC network (FIG. 5B, FIGS. 12B and 12C). Consistent with these microscopic observations, significantly elevated expression of FDC and FRC derived cytokines CXCL13 and CCL19 was found in the HVEM deficient tumors compared to controls (n=5, p<0.01) (Mueller and Germain, 2009) (FIGS. 5D and 5E).

The TNF family cytokines TNFa and LTa and LTb are essential and non-redundant activators of stromal FRCs and FDCs (Roozendaal and Mebius, 2011). Therefore, expression of these cytokines in murine lymphomas was examined. Significantly increased production of all three factors was observed in purified B220+B cells from HVEM deficient lymphoma compared to control lymphomas (FIG. 5F n=5, p<0.05). Moreover, treatment of two different mouse lymphoma lines (BCL1 and Myc/Bc12) with the HVEM ectodomain (solHVEM; 10 µg/ml) readily decreased the expression of LTa and LTb but did not reduce TNFa (FIG. 5G-I, FIG. 12D-F). Hence, HVEM deficient lymphoma B cells show aberrant production of stroma inducing TNF family cytokines.

Increased Follicular T Helper (TFH) Cells in HVEM Deficient Lymphomas

Figures 6A, 6B, 6C, 6D, 6E, 6F, 6G, 6H:
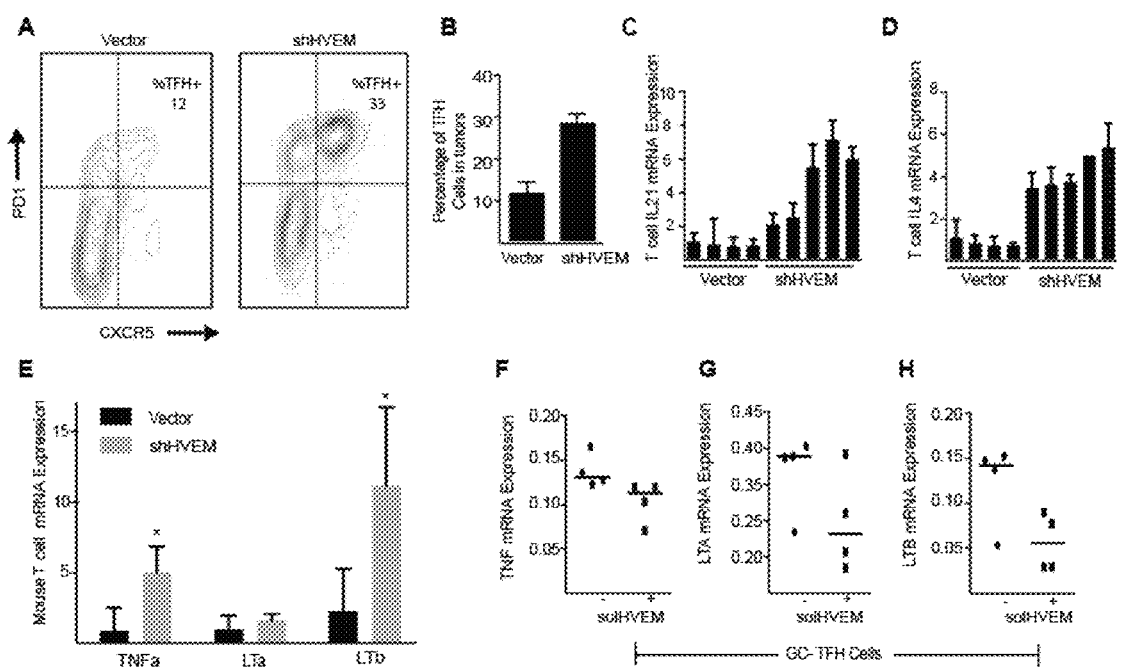
Figures 13A, 13B, 13C, 13D, 13E, 13F:
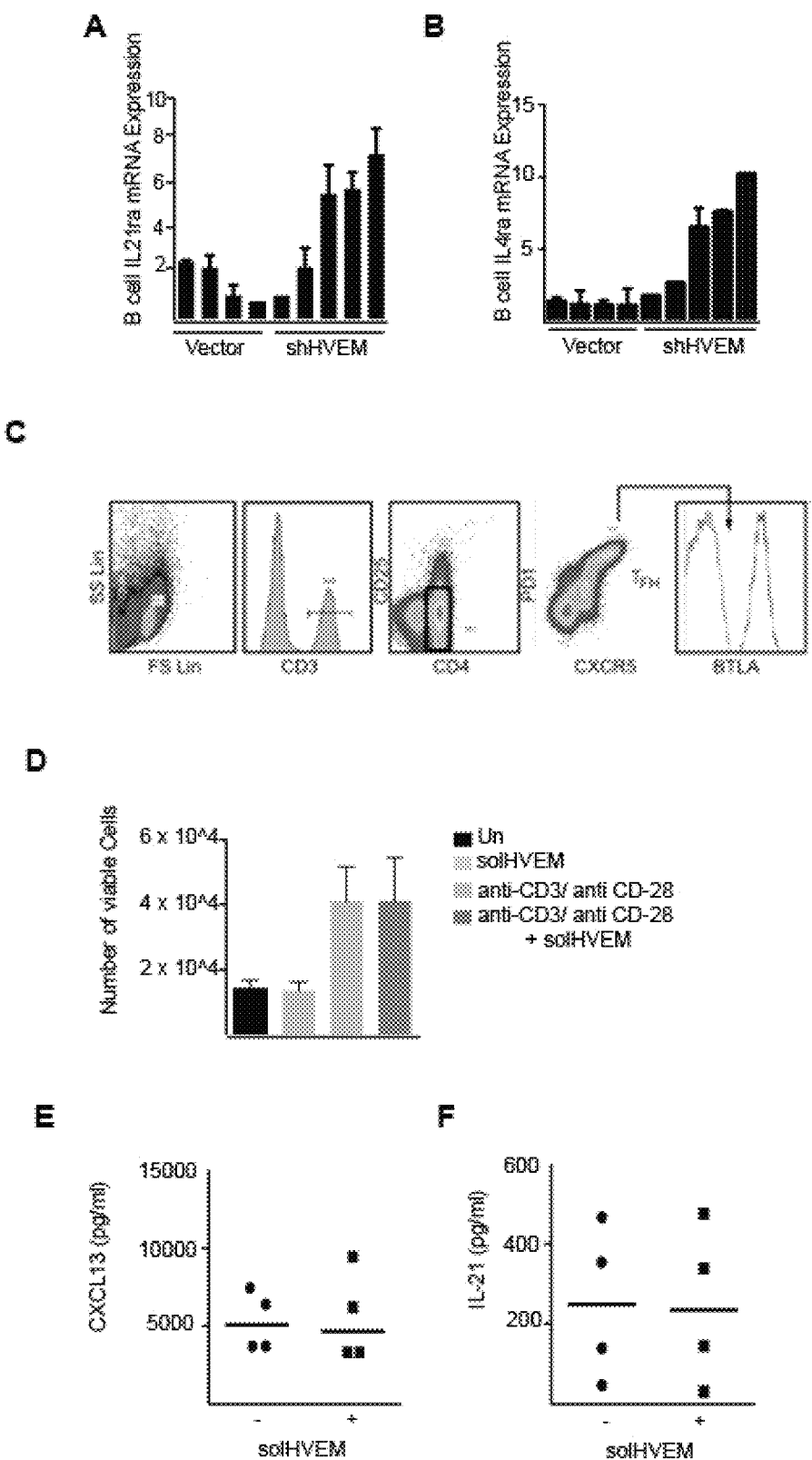
FIG. 13A-E. Analysis of TFH cell function in HVEM deficient lymphomas.
Figures 14A, 14B, 14C, 14D, 14E:
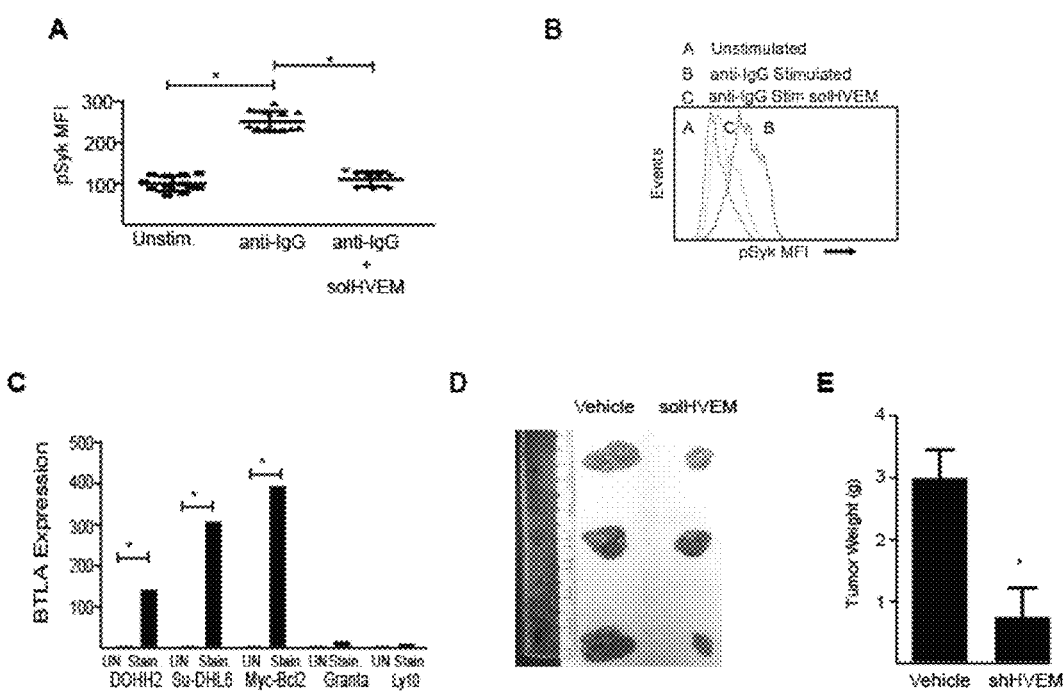
FIG. 14A-E. Effect of solHVEM (either Leu39-Val202 or Pro37-Val202) on murine and human FL B cells.

The stroma-derived cytokine CXCL13 is the main chemoattractant for CXCR5pos follicular T helper cells (TFH) (Crotty, 2014). Consistent with the increased CXCL13 production in HVEM deficient lymphomas (FIG. 5D) a significant increase in the abundance of TFH cells was observed in the HVEM deficient tumors compared to control tumors (n=3 for each; p<0.01) (FIGS. 6A and 6B). This increase in TFH cell numbers is associated with an elevated expression of the TFH derived cytokines. Specifically, increased expression of IL21, IL4, and the stroma activating cytokines TNFa, LTa, and LTb was observed in FACS purified CD3+ T cells from HVEM deficient versus control lymphomas (n for each genotype=5, p<0.01) (FIG. 6C—6E). Further, it was observed that the increased production of IL21 and IL4 by TFH cells was matched with an elevated expression of the IL21 and IL4 receptors on FACS purified lymphoma B cells from HVEM deficient lymphomas (p<0.01) (FIGS. 13A and 13B). Human TFH cells are characterized by high-level expression of the BTLA receptor (FIG. 13C) and experiments were performed to test whether HVEM directly affected these tumor infiltrating T cells. In order to test the direct effect of HVEM on TFH cells purified human TFH cells were isolated and treated with solHVEM as before in the presence or absence of stimulation with anti-CD3 and anti-CD28. SolHVEM did not affect TFH cell numbers or viability, and reductions in the expression of LTa and LTb, but not of TNFa, IL21, or CXCL13, were observed (FIG. 6F—H, FIG. 13D-F). Hence, HVEM deficient lymphomas recruit increased numbers of TFH cells that contribute to stroma activation and support B cell growth through IL4 and IL21 production.

The HVEM Ectodomain Protein Counters Lymphoma Growth In Vitro and In Vivo

Figures 7A, 7B, 7C, 7D:
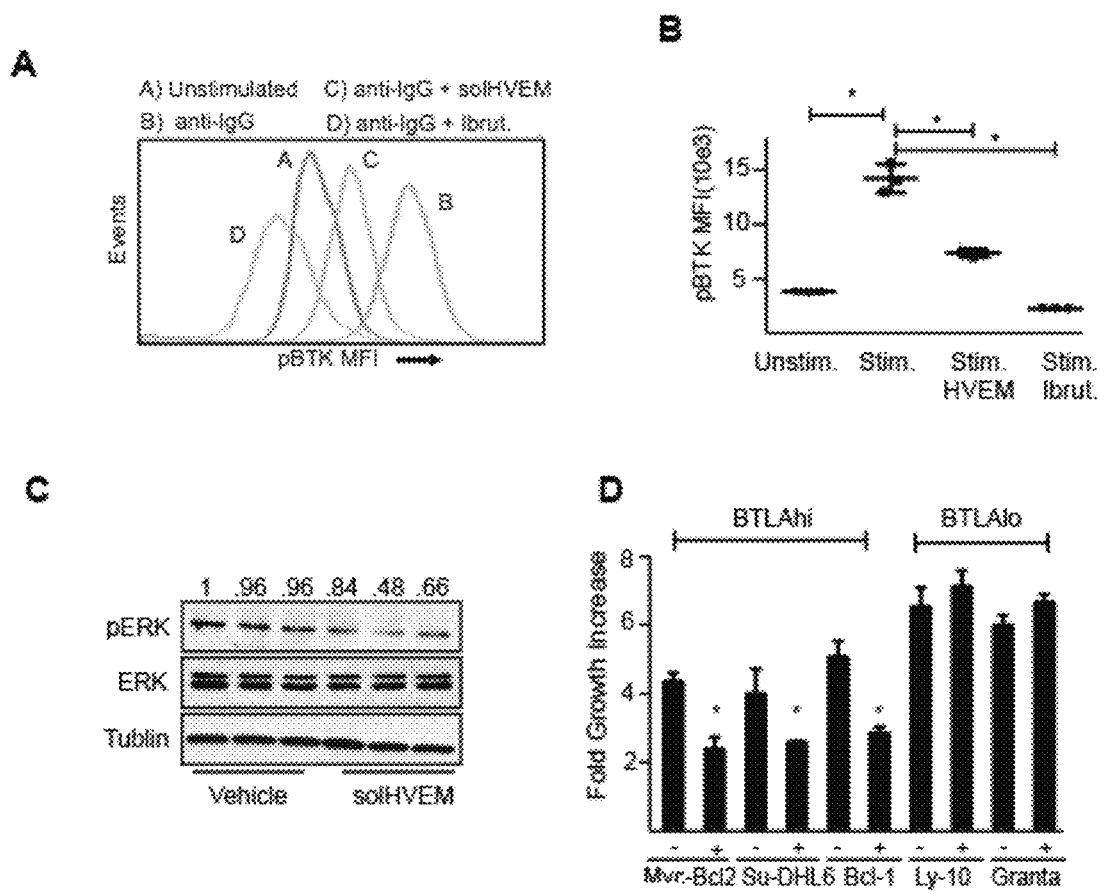
FIG. 7A-H. The solHVEM (either Leu39-Val202 or Pro37-Val202) protein restores tumor suppressive effects of HVEM.
Figure 7E:
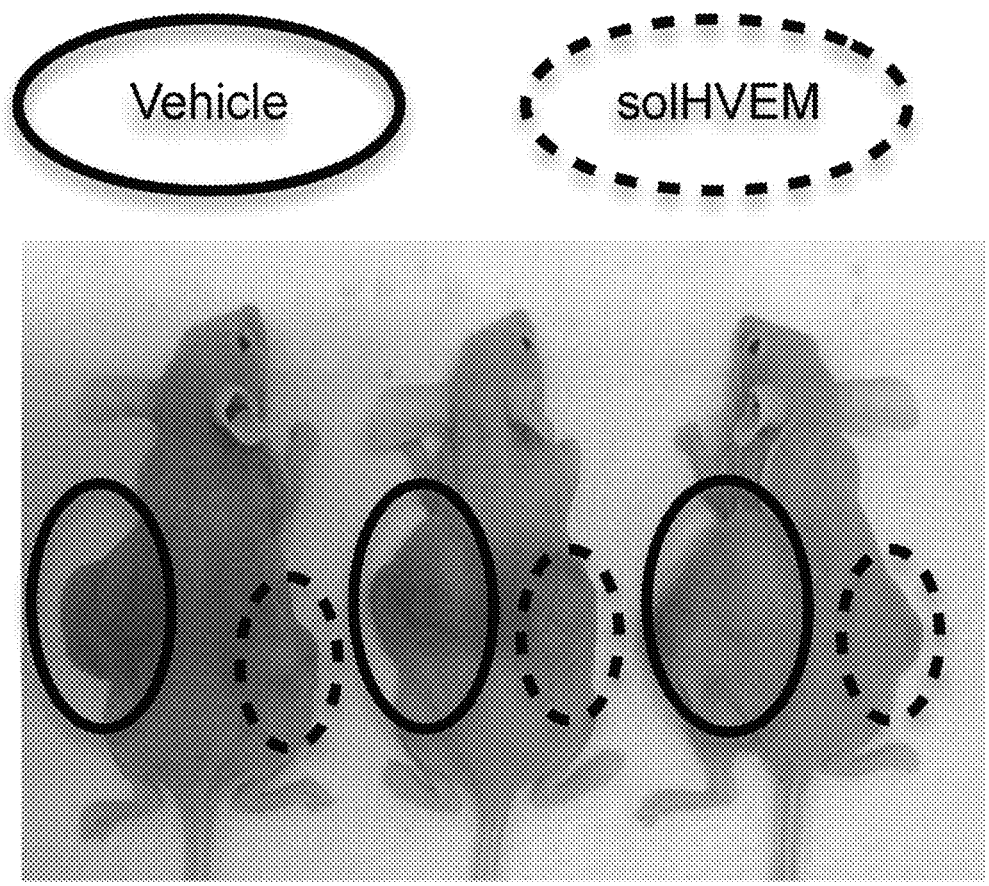
Figure 7F:
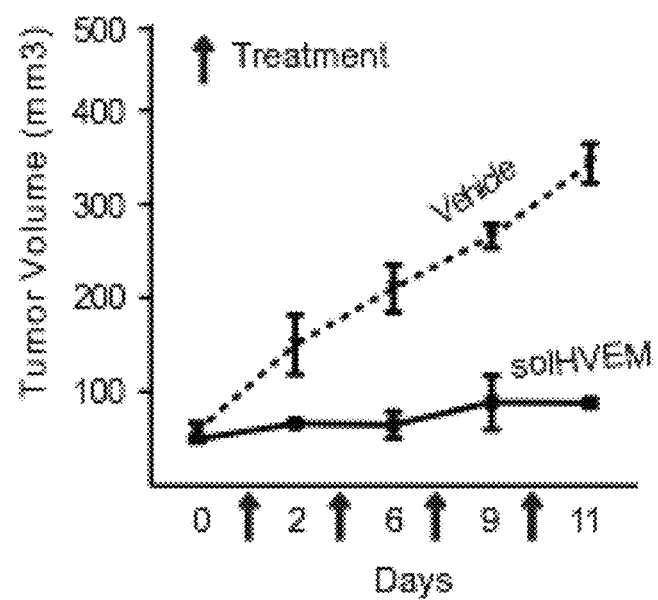
Figure 7G:
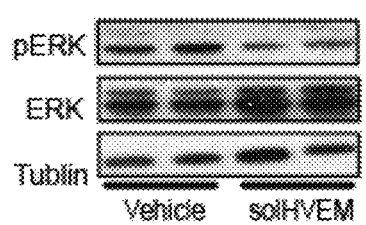
Figure 7H:
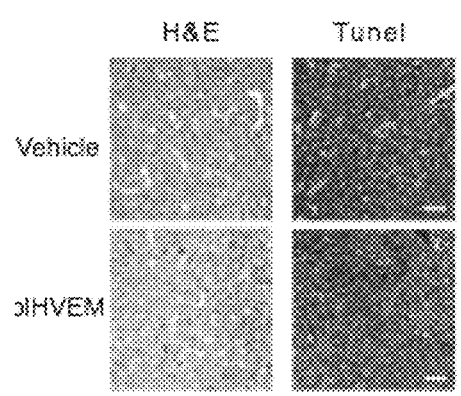

It has been demonstrated herein that the solHVEM protein can inhibit BCR pathway activation in a BTLA-dependent manner and reverse, at least in part the aberrant cytokine production in lymphoma B cells and TFH cells. Building on these findings, experiments were performed to test whether solHVEM would have any single agent activity against lymphomas. First, the expression of the BTLA receptor was characterized across a panel of human and mouse lymphoma (mostly DLBCL) cell lines. Consistent with the findings in human FL samples and primary FL B cells (FIGS. 1 and 4), it was found that cell lines fell into BTLA$^{hi}$ (DOHH2, SU-DHL6, murine MYC/BCL2) and BTLA$^{lo}$ (Granta, Su-DHL10) (FIG. 14C) groups. SolHVEM (10 µg/ml) readily blocked BTK, SYK, and ERK activation in DOHH2 cells that are BTLA" and that have a homozygous deletion of HVEM (not shown) (FIG. 7A-7C-FIGS. 7A and 7B data was generated using SolHVEM Pro37-Val202, i.e. SEQ ID No. 6). Across the full panel, solHVEM caused a significant growth inhibition in all BTLA$^{hi}$ lymphoma cells, whereas BTLA$^{lo}$ cells showed overall higher baseline growth rates and were not affected by solHVEM (FIG. 7D). Next, experiments were performed to test if solHVEM had any effect on established BTLA$^{hi}$ lymphomas in vivo. Briefly, aggressive MYC/BCL2 double positive murine lymphoma cells that express BTLA (BTLA$^{hi}$) were transplanted into the flanks of J:Nu nude mice and mice were treated with 20 µg of solHVEM or vehicle (PBS) every three days for a total four times once the engrafted tumors reached a volume of ~50 mm3. Treatment with the solHVEM protein prevented any further tumor growth, whereas the vehicle treated tumors expanded rapidly (n=4 for vehicle and solHVEM; p<0.01) (FIGS. 7E and 7F, FIGS. 14D and 14E). The effect of solHVEM was not merely cytostatic and TUNEL stains showed abundant apoptosis and immunoblots indicate ERK inhibition in vivo (FIGS. 7G and 7H). Hence, solHVEM has significant single agent activity against lymphomas in vivo. Similar results were obtained both in vitro and in vivo with a different soluble HVEM molecule consisting of the extracellular region from amino acids Pro37 to Val202 (SEQ ID NO. 6). These results are summarized in Example 2.

Discussion

Dual Function of the HVEM-BTLA Tumor Suppressor Axis in Lymphoma

The GC is the origin of most human B cell lymphomas and the data presented herein provides new insight into their pathogenesis. It has now been shown that the HVEM-BTLA interaction is disrupted in 75% of GC B cell lymphomas—indicating that it is a critical barrier to lymphoma development. The HVEM receptor gene is among the most frequent genetic targets in lymphoma and somatic mutations and chromosomal deletions result in complete inactivation in a large fraction of GC lymphomas including FLs and DLBCLs. BTLA is the only HVEM interacting receptor expressed in B cells and lymphomas that retain wild type HVEM are likely to silence expression of the BTLA receptor gene. However, BTLA is not a target of mutations or deletions. Instead BTLA is a target of the KMT2D (MLL2)

histone methyltransferase and KMT2D inactivation in lymphomas may contribute to reduced BTLA expression (Ortega-Molina et al., 2015).

HVEM loss has dual effects on lymphoma B cells and also reshapes the local microenvironment. First, loss of HVEM stimulates BCR signaling and B cell growth in a cell autonomous and BTLA-dependent manner. The inhibitory BTLA receptor has two ITIM domains that can interact with B cell receptor signaling molecules (CD79, SHP1/2) (Gavrieli et al., 2003; Vendel et al., 2009; Watanabe et al., 2003). Stimulation of BTLA by cell surface HVEM or soluble HVEM leads to inhibition of BCR signaling molecules and blocks lymphoma cell proliferation. In T cells this interaction has been shown to occur in cis on the same cell (Cheung et al., 2009). A similar cis interaction in B cells leads to a cell autonomous growth advantage and is likely a key factor driving the genetic HVEM inactivation.

In addition to its cell autonomous effects on B cell growth, HVEM is also a key driver of the lymphoma niche. HVEM-deficient B lymphocytes produce increased amounts of TNF family cytokines (TNFa, LTa, LTb) that are the key activators of lymphoid stroma cells such as FDCs and FRCs (Ame-Thomas et al., 2007; Guilloton et al., 2012; Roozendaal and Mebius, 2011). The activated lymphoid stroma in HVEM deficient mouse lymphomas closely resembles the abnormal stroma activation seen in human FLs (Mourcin et al., 2012). Human FL cells depend on their stroma which supports FL B cells, at least in part, through increased CCL19 and CXCL13 mediated recruitment of IL4, IL21, and CD40L producing TFH cells (Ame-Thomas et al., 2015{Pangault, 2010 #1807; Ame-Thomas et al., 2012). HVEM deficiency is sufficient to trigger these exact changes in cytokine production and cellular composition that together contribute to a lymphoma permissive niche in vivo.

HVEM produces direct effects through BTLA interactions and also indirect effects secondary to altered cytokine production. For example, lymphoid stromal cells do not express BTLA (not shown) and effects on the lymphoid stroma are mostly secondary to increased production of TNF family cytokines. On the other hand, BTLA is present at very high levels on TFH cells. Accordingly, in the present study it was noted that TFH cells are subject to both increased CXCL13 mediated recruitment and also direct effects of HVEM on TFH cells. Similarly, HVEM directly engages BTLA on lymphoma B cells and in addition TFH derived cytokines such as IL4 and IL21 provide further support B cell growth. HVEM may have additional direct and secondary effects. The results presented herein show that loss of HVEM disrupts a critical node that controls B cell growth and maintains a balanced GC environment.

Restoring the HVEM-BTLA Interaction for Therapy

HVEM is one of the most frequently mutated genes in FL and DLBCL. Accordingly, a therapeutic strategy tailored to HVEM deficient lymphomas would be highly beneficial. Notably, the interactions between the tumor suppressive HVEM and BTLA receptors occur at the cell surface and are therefore directly accessible. In the present study a soluble HVEM ectodomain was able to bind BTLA and induce significant single agent effects on BCR signaling, cytokine production, and tumor growth in vivo. These therapeutic effects of solHVEM depend on BTLA expression, indicating that alternate strategies may be needed to treat BTLA deficient lymphomas, and suggesting that BTLA expression can be a predictor of solHVEM response. The results presented herein provide proof-of-concept for therapeutic strategies aimed at restoring, at least in part, the tumor suppressive functions of HVEM in GC lymphomas. Enhanced ligands based on HVEM or BTLA activating antibodies, and improved vehicles for tumor specific HVEM delivery, could also produce tumor suppressive functions effects in GC lymphomas.

Materials & Methods

Statistical Methods

Sample sizes for comparisons between cell types, or between mouse genotypes, followed Mead's recommendations (Festing, 2002). Samples were allocated to their experimental groups according to their pre-determined type (i.e mouse genotype) and therefore there was no randomization. Investigators were not blinded to the experimental groups. In the experiments for which data is provided in FIGS. 2B and 3A, only mice that developed lymphomas were considered; mice that didn't develop lymphomas were censored and indicated with ticks in the Kaplan-Meier curves. Quantitative PCR data were obtained from independent biological replicates (n values indicated in the corresponding Figure legends). Normal distribution and equal variance was confirmed in the large majority of data and, therefore, normality and equal variance was assumed for all samples. The Student's t-test (two-tailed, unpaired) was used to estimate statistical significance. Survival in mouse experiments was represented with Kaplan-Meier curves, and significance was estimated with the log-rank test. For association analysis between HVEM and BTLA expression in human FL tissue biopsies, a Chi-square test was used.

Exon Sequencing of HVEM in FL

Cases were analyzed as described previously (Li et al., 2014; Yildiz et al., 2015). Briefly, primers to amplify and sequence all coding exons and adjacent intronic sequences of HVEM were designed using the primer 3 program (http://primer3.ut.ee/) and sequence information generated using direct sequencing as described. Mutations were confirmed to be somatically acquired using unamplified lymphoma cell-derived DNA and paired CD3 cell-derived DNA from sorted cells as templates.

Deep Coverage Massively Parallel Re-Sequencing of HVEM

A customized multiplexed primer panel (Qiagen Gene Read Panel) was used to amplify all coding exons of HVEM. PCR products were pooled and sequencing libraries prepared using barcoded adapters. Sequencing was done on a HiSeq2000 sequencer. Bioinformatics nomination of sequence variants was performed using a custom algorithm. Fastq files were uploaded to the Qiagen GeneRead data portal (http://ngsdataanalysis.sabiosciences.com) to trim primer regions from the reads and to align to the human genome (build hg19) using bowtie26. The aligned bam files were individually downloaded from the Qiagen portal and submitted to VarScan (2.3.6) for variant calling with default parameters. SnpEff (3.4B) was used to annotate the variants with gene names and predicted impact on amino acid sequence; dbNSFP (2.1) was used to annotate predicted functional impact based on standard tools (Sift, Polyphen, MutationTaster). Variants found in 1000 Genomes phase 2 were excluded. Jacquard, a custom tool developed by the UM Bioinformatics Core, was used to combine all sample VCFs into a single matrix of variants by samples. All sequence variants with VAF>15% were validated in stock T and paired N DNA using Sanger sequencing.

Array Comparative Genomic Hybridization/Gistic Analysis

DNA from fresh frozen or OCT-embedded tissue was isolated and processed as previously described (Bouska et al., 2014; Oricchio et al., 2011, Bouska, 2014 #43). In short, labeling and hybridization was done according to protocols performed by Agilent Technologies. Data are available on GEO under accession no. GSE40989. Copy Number Data from the second dataset that consisted of 197 follicular lymphoma patients (UNMC dataset) has been generated using GeneChip Human Mapping 250K Nsp SNP array (Affymetrix) as described in (Bouska et al., 2014). To identify significantly amplified and deleted regions the Gistic 2.0 R package implementing the GISTIC algorithm (Beroukhim et al., 2010) was used. GISTIC has been run on segmented copy number data generated for each dataset using the DNAcopy R package from Bioconductor (Olshen et al., 2004).

Mouse Model of FL

The vavPBc12 mouse model, as adapted for adoptive transfer to retrovirally transduced HPCs, was used (see Egle et al., 2004) and Wendel et al., 2004). In short, vavPBc12 transgenic fetal liver cells were isolated from vavPBc12 heterozygous animals at embryonic day 14.5 (E14.5). The HPCs were grown in vitro for 4 days in a specially adapted growth medium and retrovirally transduced with MSCV vectors directing the expression of shRNAs of interest. The HPCs were transplanted into lethally irradiated wild type recipients and disease onset monitored once weekly by palpation. Data were analyzed in Kaplan-Meier format using log-rank (Mantel-Cox) test for statistical significance.

Immunohistochemical and TMA Methods

Immunohistochemistry (IHC) was applied to a tissue microarray (TMA) encompassing 1.5 mm duplicate cores of 199 formalin-fixed, paraffin-embedded (FFPE) tissue specimens from 186 patients diagnosed with FL (Kridel et al., 2015). 4 µm sections were cut and IHC was performed on a Ventana BenchMark XT platform (Ventana, Ariz.) using a mouse monoclonal antibody against HVEM (dilution 1:50; clone 2G6-2C7; Abnova, Walnut, Calif.) and a rabbit polyclonal antibody against CD272/BTLA (dilution 1:100; Epitomics, cat. # S2379; Toronto, ON). Slides were evaluated by two hematopathologists for the percentage of positive tumor cells (in 10% increments) and staining intensity (0=negative, 1=weak, 2=moderate, 3=strong). Representative images were acquired with a Nikon DS-Fil camera connected to a Nikon Eclipse E600 microscope. Spleens were collected for histology and immunochemistry analysis. Sections were stained with HE, PNA, BCL6, TUNEL, Ki67 as previously described (Oricchio et al., 2011). Ki67 positive cells were quantified using Metamorph software.

Flow Cytometry on FL Mouse Models

Flow cytometry analyses of cell suspensions obtained after mechanical dissociation were performed on a BD LSR Fortessa (Becton Dickinson, Franklin Lakes, N.J.). Tumor cell suspensions of representative tumors of each genotype were stained as described (Wendel et al., 2004). The following antibodies used in staining were obtained from BD Biosciences: CD8 (clone RA3-6B2), CD4 (clone 1D3), FAS (clone Jo2), T and B cell activation antigen (GL7), IgG (A85-1), IgM (R6-60.2), CD3 (clone 17A2) CXCR5 (clone RF8B2), or from ebiosciences: PD-1 (clone JH3), CD44 (clone IM7), CD62L (clone MEL14), or from Biolegend: HVEM (clone HMHV-1B18), BTLA (clone 6A6).

Purification and Analysis of B and T Cells from FL Mouse Models

B and T cells were isolated from the spleens of mice using bead cell separation. Whole cell lysates were subject to separation using either the Pan T Cell Isolation Kit or the B Cell Isolation Kit (Miltenyl Biotec) and isolated subject to manufacturer's instructions.

Total RNA was extracted from tumors, sorted T cells, and sorted B cells using the Qiagen RNA extraction kit. Reverse transcription was performed on 1 µg of total RNA using the M-MulV reverse transcriptase (New England BioLabs). qRT-PCR analysis was performed by the $\Delta\Delta Ct$ method as described (Mavrakis et al., 2008) using TaqMan Universal master mix on an ABI Prism 7000 Sequence Detection System (Applied Biosystems). Taqman Gene Expression assays from Applied Biosystems were used for: Gusb, IL-21, IL-4, IL-21ra, IL-4ra, HVEM, BTLA, p21, and CXCL13.

Immunohistofluorescence on Stromal Cells

Mouse spleens and human lymph nodes were snap frozen in OCT (Tissue-Tek OCT Compound). Twenty-micrometer sections were fixed in 4% PFA for 15 min at room temperature. Sections were incubated for 1 hour with a blocking solution (PBS, 10% BSA, 10% Donkey serum, 0.1% Saponin) then incubated in a humidified chamber overnight at 4° C. with the following primary antibodies: CD21/CD35 (Rat IgG2b, dilution 1/50, BD Biosciences) and collagen I (Rabbit polyclonal, dilution 1/100, Abcam) for mouse spleens; and CD21L (Mouse IgM, dilution 1/100, Dako), Transglutaminase-2 (Mouse IgG1, dilution 1/50, Abcam), and CD20 (Polyclonal Rabbit, dilution 1/50, Abacam) for human lymph nodes. After washes, slides were incubated with the corresponding secondary antibodies (Jackson ImmunoResearch) and were finally mounted in Mowiol anti-fade reagent containing SytoxBlue (dilution 1/500, Invitrogen) and analyzed by confocal microscopy on a SP8 (Leica Microsystems). ImageJ software was used for image analysis.

Human Cell Samples

Subjects were recruited under institutional review board approval and informed consent processes. Samples comprised lymph nodes (LN) obtained from patients with follicular lymphoma (FL) and tonsils collected from children undergoing routine tonsillectomy. Tissues were cut into pieces and flushed using syringes and needles. Tonsil TFH were sorted using a FACSAria (Becton Dickinson) as CD3posCD4posCXCR5hiICOShiCD25neg cells with a purity greater than 98% as described (Mourcin et al., 2012) {Pangault, 2010 #2203}. Primary FL B cells were purified using the B-cell isolation kit II (Miltenyi Biotech). Antibodies used in staining were: Miltenyi CD3 (clone BW264/56), Beckman Coulter CD4 (clone 13B8.2), eBiosciences (clone J105), and BD Biosciences CD25 (clone M-A251), CXCR5 (RF8B2), and BTLA (clone J168-540).

TFH Stimulation

Purified TFH were cultured in IMDM 10% FCS with or without anti-CD3 (0.6 µg/mL) and anti-CD28 (0.6 m/mL, Pelicluster Sanquin) MAbs in the presence or not of solHVEM (10 µg/mL). After 3 days of culture, the number of viable TFH was evaluated by flow cytometry using count beads (Flow Count, Beckman Coulter) and Topro-3 staining (Invitrogen). CXCL13 was quantified in culture supernatants by ELISA (R&D Systems) according to manufacturer's instructions.

Analysis of BCR Signaling in Human FL

Purified IgGpos FL B cells were stimulated using FITC-conjugated goat anti-human IgG (Invitrogen, 10 mg/mL) in the presence of $H_2O_2$ (1 mM) with or without solHVEM (10 µg/mL). The reaction was stopped by adding PFA at 4% final concentration for 15 min at room temperature. Fixed cells were permeabilized with methanol 80% for 20 min at −20° C. in dark before washing and rehydratation with PBS-1% BSA. Phosphoprotein activation was quantified using Alexa 647-conjugated anti-pSyk (clone 17A/p-ZAP70), anti-pBLNK (clone j117-1278), or anti-pERK1/2 (clone 20A, BD Biosciences) and analyzed on B cells expressing clonal heavy and light chain gated using the anti-IgG FITC Ab and a PE-conjugated anti-kappa Ab (Southern Biotech).

Phospho Flow Cytometry in Mouse Cells

For phospho-BTK, phospho-Syk staining, cells were pretreated for 60 min with either 5 μg/mL of sHVEM (R&D Systems) or 10 ng/mL Ibrutinib (ChemieTek PCI-32765) at 37° C. Cells were fixed by adding equal volume of formaldehyde directly to the cells. Cells were incubated for 10 minutes at room temperature, washed 2× in PBS and the residual cells were permeabilized in 1 mL of ice cold methanol (100%) for 30 min on ice. Cells were then washed twice and stained with the phospho-BTK (Bd Biosciences clone N35-88) and phospho-Syk (Bd Biosciences clone 17 A/P-Zap70) and analyzed on BD LSRFortessa.

Sequencing of VDJ Regions

RNA was prepared from potentially tumoral lymphoid tissues and from a normal mouse spleen as control. Expressed VDJ regions from μ heavy chain transcripts were sequenced through a next generation method. This strategy combined 5' RACE PCR, pyrosequencing and precise repertoire analysis with quantification of the most frequent clonotypes using IMGT/High-V-QuestmRNA and associated tools available on IMGT (the International ImMunoGeneTics information website (www.imgt.org). RACE-PCR started with a reverse primer hybridizing within the μ CH1 exon.

Cell Culture, and Cellular Proliferation Assays

Lymphoma cell lines DoHH2, Ly-10, Granta, Su-DHL-6 were maintained in RPMI 1640 with 10% fetal bovine serum, 1% L-Glutamine and 1% penicillin/streptomycin. Mouse lymphoma cell line myc-bcl2 was maintained in IMDM-DMEM (50:50) with 10% fetal bovine serum, 1% L-Glutamine, and 1% penicillin/streptomycin. Cell lines were seeded at 5×105/mL and were treated with 5 m/ml of sHVEM. After 24 hours cell number was counted using hemocytometer for a total of 72 hours after treatment.

In Vivo Growth and Treatment Studies

Transplant and treatment studies were generated as previously described (Schatz et al., 2011). In summary, subcutaneous injection of one million myc-bcl2 mouse lymphoma cells combined with Matrigel (BD) in the right and left flanks of mice J:Nu Nude (Foxn1 nu/Foxn1 nu). Once tumors reached 75-mm3 mice were treated every three days by intra tumor injection with 20 m of sHVEM diluted in PBS (right flank) or with vehicle control (left flank). Tumor sizes were measured and recorded every three days. Tumors were weighed after the animals were sacrificed and tumors excised.

Immunoblots

Immunoblots were performed using whole cell lysates or supernatants as previously described (Wendel et al., 2004). In brief, 30 μg protein/sample was resolved on SDS-PAGE gels and transferred to Immobilon-P membranes (Millipore). Antibodies were against, pSyk (Cell Signaling Technologies #2712), Syk (Cell Signaling Technologies #2710), pBTK (Cell Signaling Technologies #5082), BTK (Cell Signaling Technologies #3533) pERK (Cell Signaling Technologies #9102), ERK (Cell Signaling Technologies #4370) and Tubulin (Sigma-Aldrich). Enhanced chemiluminescence was used for detection (ECL; GE Healthcare).

Example 2

In Vitro and In Vivo Effects of Treatment with Additional Soluble HVEM Polypeptides Several of the experiments described in Example 1, above, involved use of a L39-V202 soluble HVEM polypeptide (having the sequence provided in SEQ ID NO. 8, which consists of amino acids L39-V202 of the full-length HVEM amino acid sequence (SEQ ID NO. 2)). Comparable results were also obtained using other soluble HVEM protein sequences. The results presented in this Example were obtained with a Pro37-Val202 soluble HVEM polypeptide (encoded by the nucleotide sequence of SEQ ID NO. 5, and having the amino acid sequence provided in SEQ ID NO. 6, which consists of amino acids Pro37-Val202 of the full-length HVEM amino acid sequence of SEQ ID NO. 2). Unless specifically stated otherwise any reference to "solHVEM" in Example 2 or in FIGS. 15-24, refers to the Pro37-Val202 soluble HVEM ectodomain polypeptide of SEQ ID NO. 6 (as encoded by the nucleotide sequence of SEQ ID NO. 5).

Figure 15A:
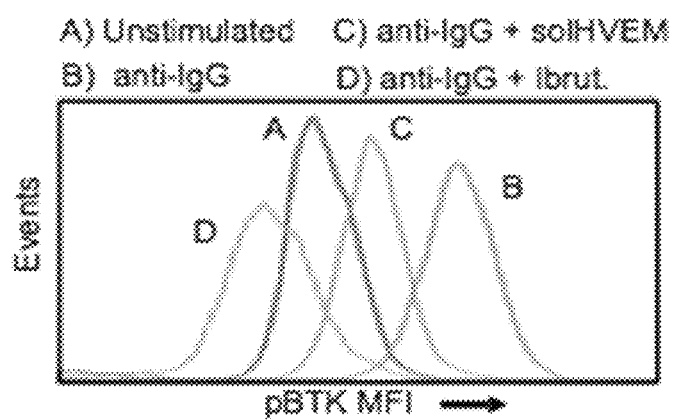
FIG. 15A-B. sTNFRSF14 opposes B cell receptor signaling in lymphoma B cells by decreasing P-BTK. A B-cell lymphoma cell line (DOHH2) was pre-treated for one hour with the soluble ectodomain of TNFRSF14 (sTNFRSF14) Pro 37-Val 202 (5 ug/ml) or the BTK inhibitor Ibrutinib (10nmM) and then stimulated for 5 mins at 37° C. with anti-IgG molecule. The cells were subsequently fixed and permeabilized and probed for pBTK expression using phospo-flow antibodies and analyzed on BD Fortessa.
Figure 15B:
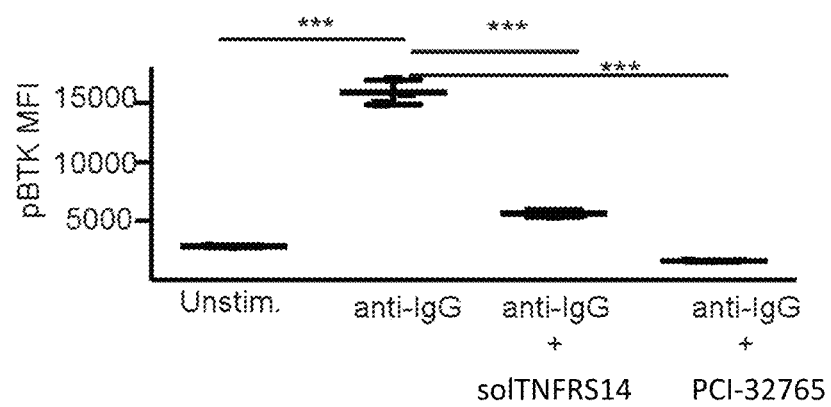
Figures 16A, 16B:
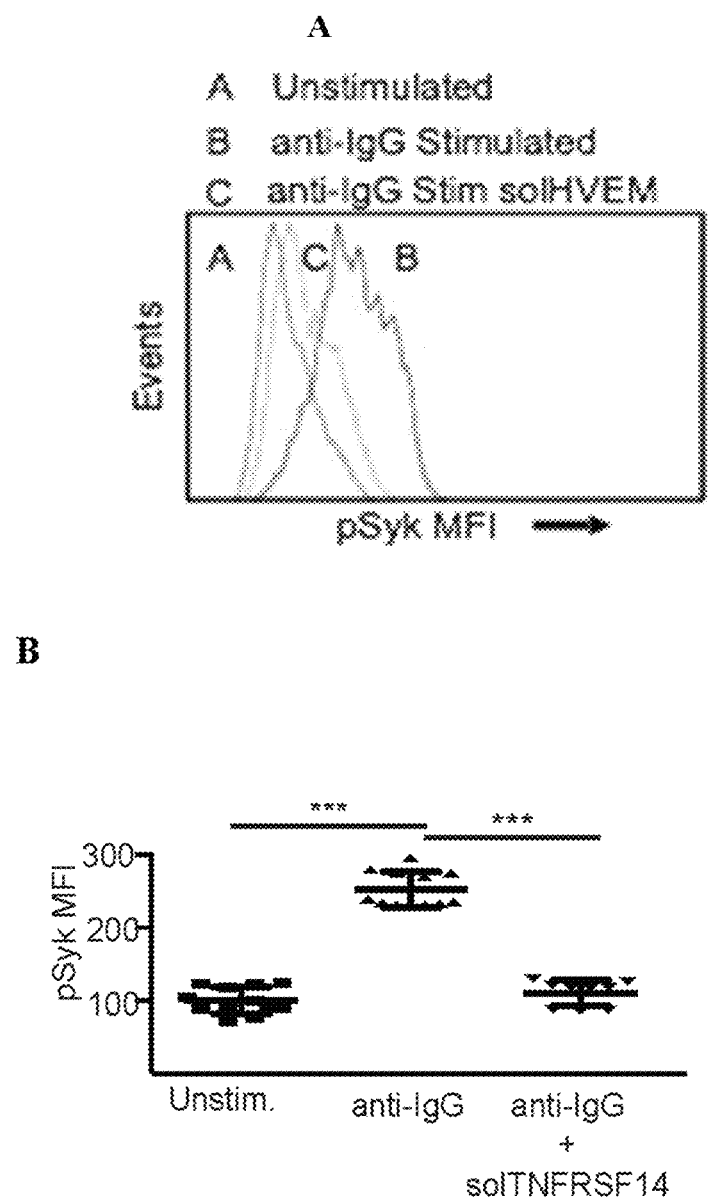
FIG. 16A-B. sTNFRSF14 opposes B-cell receptor signaling in lymphoma B cells by decreasing P-SYK. A B-cell lymphoma cell line (DOHH2) was pre-treated for one hour with the soluble ectodomain of TNFRSF14 (sTNFRSF14) Pro37-Val 202 (5 ug/ml) or the BTK inhibitor Ibrutinib (10nmM) and then stimulated for 5 mins at 37° C. with anti-IgG molecule. The cells were subsequently fixed and permeabilized and probed for pSYK expression using phospo-flow antibodies and analyzed on a BD Fortessa.

Some experiments were performed using DOHH2 cells—a cell line that expresses BTLA. Human DOHH2 cells were stimulated with anti-immunoglobulin G (anti-IgG) either alone, in conjunction with sTNFRSF14 (Pro37-Val202), or with the BTK ibrutinib. Anti-IgG treatment caused an ibrutinib-sensitive activation (phosphorylation) of BTK, which was effectively blocked by pre-incubating the DOHH2 cells with sTNFRSF14 for one hour before stimulating the cells (FIG. 15A-B). This inhibiting effect was also seen upstream of BTK in the BCR pathway—levels of phosphorylated SYK were also inhibited when pre-treated with sTNFRSF14 before activation with anti-IgG (FIG. 16A-B).

Figure 17:
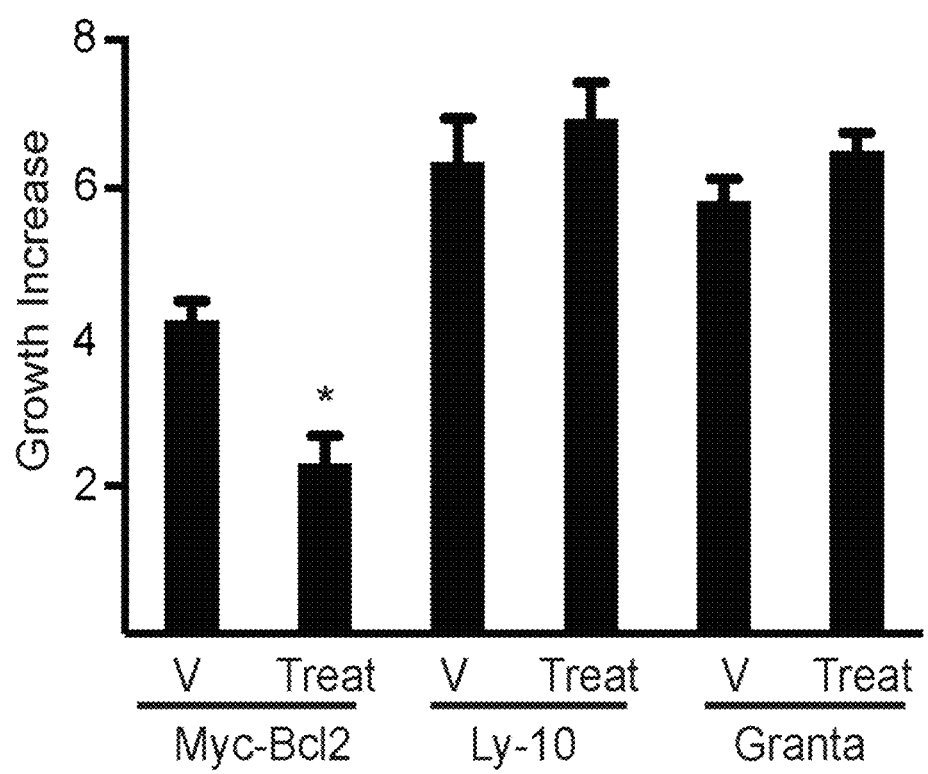
FIG. 17. sTNFRSF14 inhibits the growth of lymphoma cell lines in vitro. Three lymphoma cell lines (Myc-Bcl2, LY-10, Granta) were plated at $1\times10^5$ cells/ml and were treated with sTNFRSF14 (5 ug/ml) or vehicle each day for 72 hours. After 72 hours cells were counted using a hemocytometer. Each bar represents the average of three independent experiments.
Figure 18:
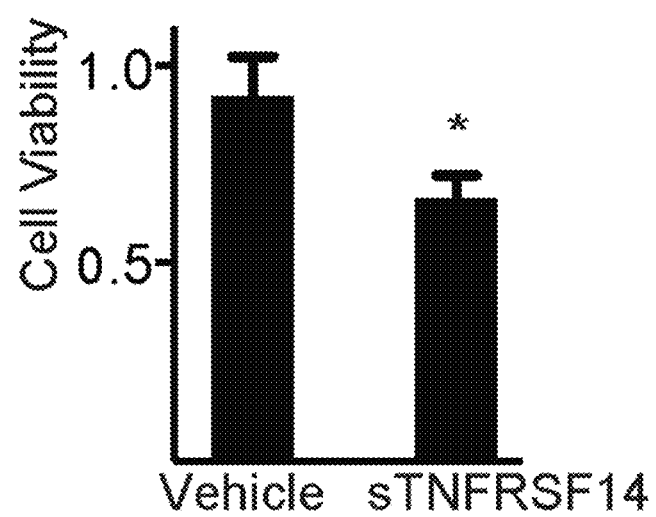
FIG. 18. sTNFRSF14 decreases cell viability in vitro. Cells of the myc-Bcl2 lymphoma cell line were plated at a density of $1\times10^5$ cells/ml and they were treated with sTNFRSF14 (5 ug/ml) or vehicle. After 24 hours of treatment cell viability was assessed using CellTiterGlo reagent.
Figure 19:
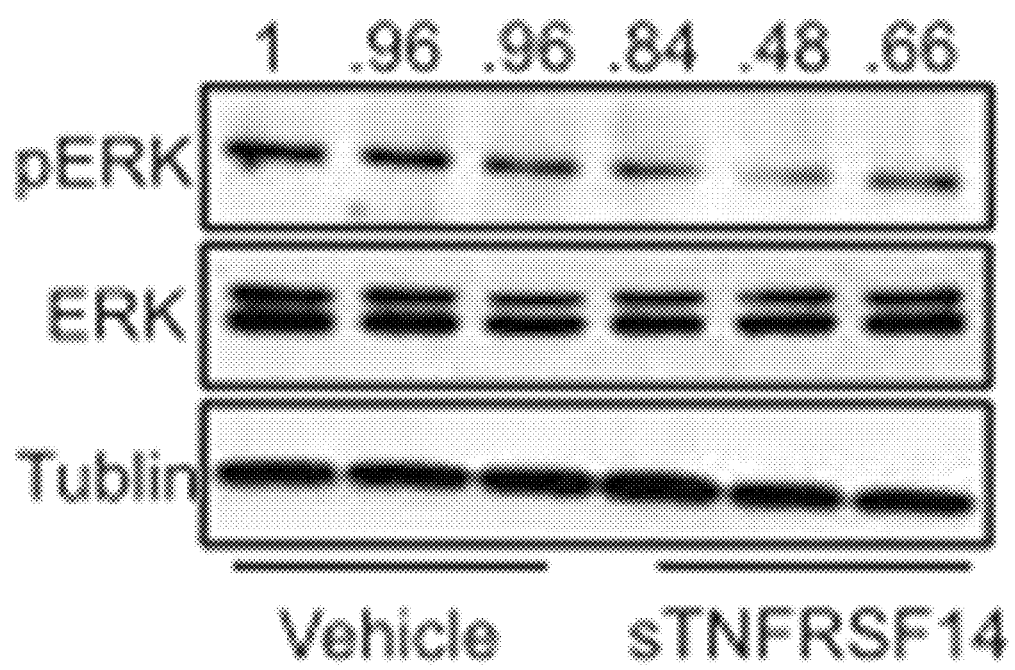
FIG. 19. In vitro effect of sTNFRSF14. Immunoblots of cell lines that were treated with 5 ug/ml of sTNFRSF14. Blots were probed as indicated.

Experiments were performed to determine if this inhibition of signaling in vitro was seen in other cell lines. Cell lines that either expressed high amounts of BTLA or did not express BTLA were exposed to 5 ug of sTNFRSF14 and cell growth was monitored over a three day time period. Strikingly, the cell lines in which the largest effect on growth were observed were those that expressed the highest levels of BTLA (Myc-Bcl2 cell line), whereas in cell lines that did not express BTLA sTNFRSF14 did not inhibit cell growth (FIG. 17). In vitro treatment caused a modest decrease in cell viability but clearly reduced the ERK phosphorylation levels in the cell lines that expressed high levels of BTLA (FIG. 18, FIG. 19).

Figure 20:
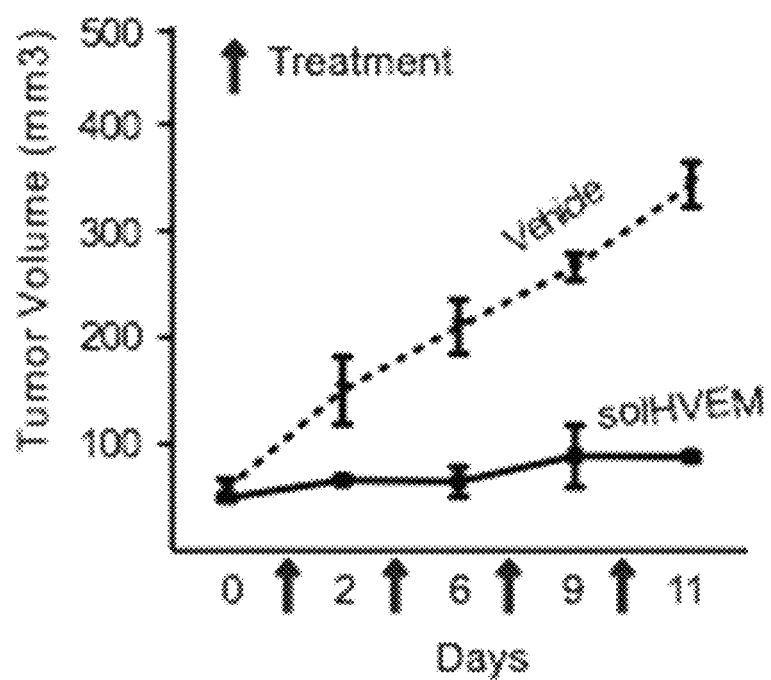
FIG. 20. sTNFRSF14 inhibits tumor growth in vivo. Xenograft myc-bcl2 lymphomas were grown in the flanks of mice. When the tumors reached a volume of approximately 0.5 cm$^3$ mice were treated every other day by intra-tumoral injection in the flanks with 20 ug/ml of sTNFRSF14diluted in PBS. The control (vehicle) animals were treated with PBS. Tumors were weighed and volumes were measured twice weekly.
Figure 21:
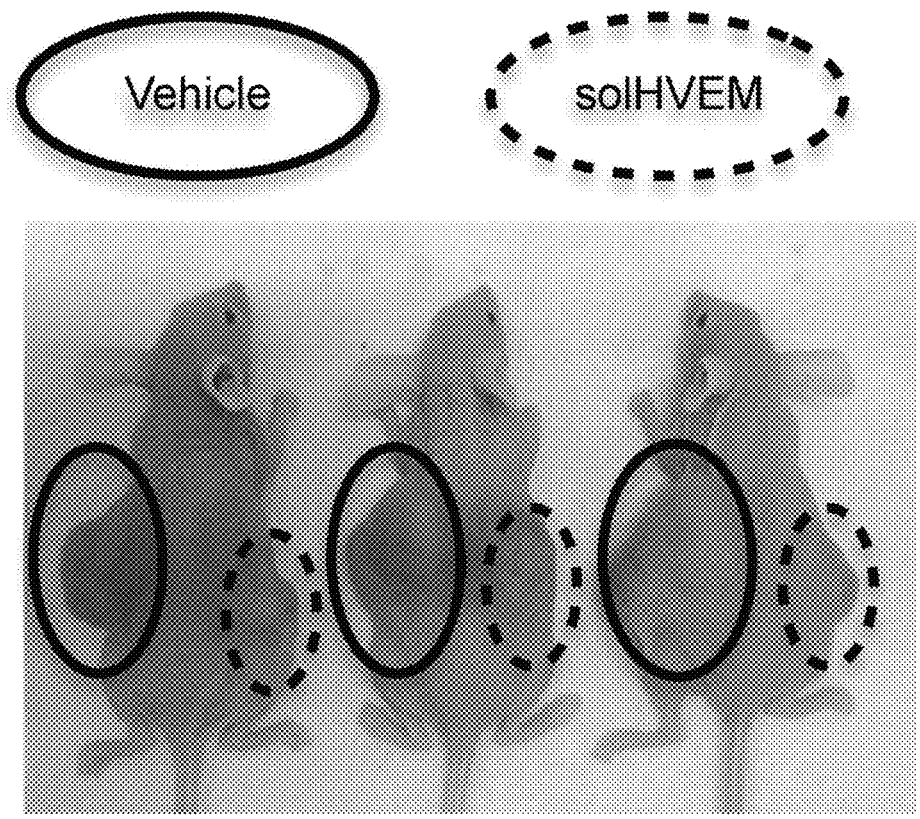
FIG. 21. sTNFRSF14 decreases lymphoma growth in a xenograft model. 5 million myc-Bcl2 cells were mixed with Matrigel and injected subcutaneously into the flanks of mice J:Nu Nude (Foxn1 nu/Foxn1 nu) mice. Animals were sacrificed according to IUCAC protocols. Upon sacrifice tumors were weighed and measured.
Figure 22:
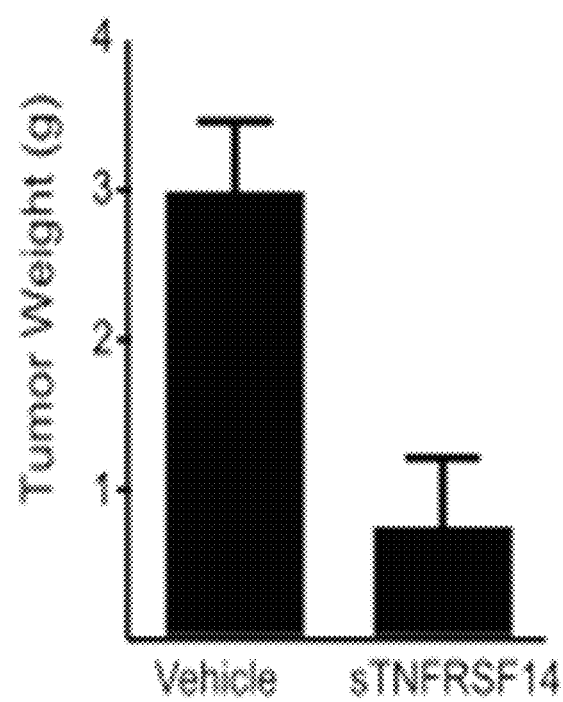
FIG. 22. Exogenous administration of sTNFRSF14 suppresses mouse lymphoma xenografts. Animals were sacrificed on day day 11 and the xenografted tumors were excised from the flanks of the mice. The tumors from each flank—treated (sTNFRSF14) and untreated (vehicle) were weighed. Bars represent the average of n=4 mice.
Figure 23:
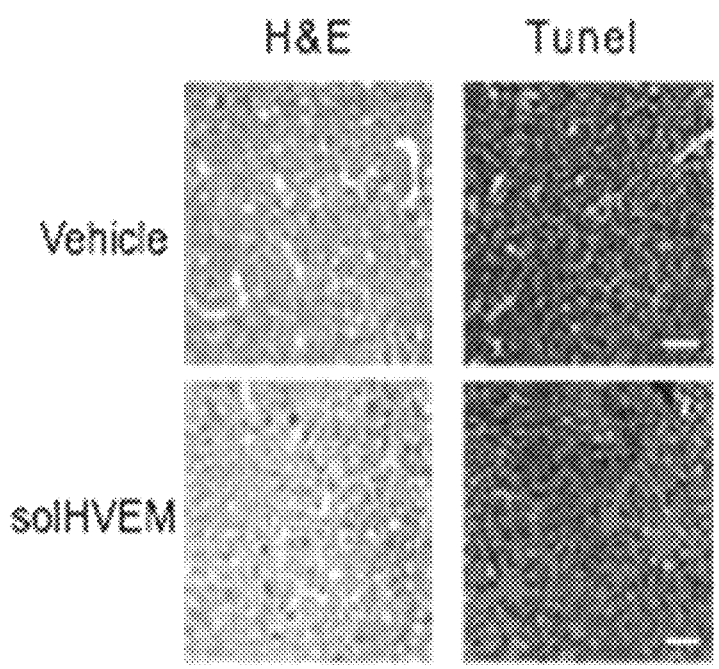
FIG. 23. Molecular characterization of in vivo tumors after treatment with sTNFRSF14.
Figure 24:
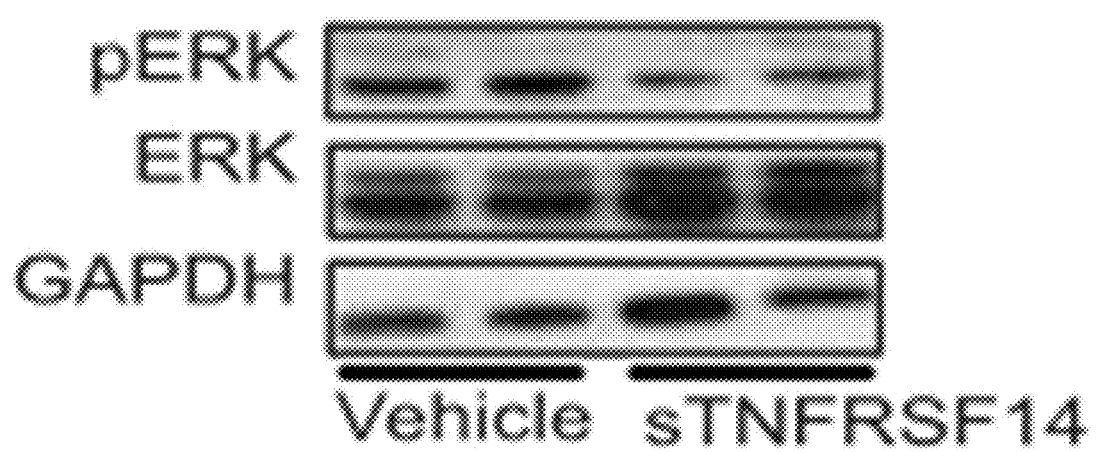
FIG. 24. Immunohistochemical analysis of xenograft tumors. Pathological analysis of sTNFRSF14 treated and vehicle treated mouse lymphomas. Tumors were excised from the flanks of the animals and fixed in 4% paraformaldehyde overnight. The tumors were sectioned and stained via IHC for particular tumor markers. Representative staining for HE, TUNEL, and Ki67 is shown.

To study the effects of the sTNFRSF14 polypeptide in vivo, five (5) million myc-bcl2 cells were injected into both the right and left flanks of nude mice. Upon formation of palpable tumors treatment was commenced. The treatment comprise injecting mice intra-tumorally with either 20 ug of sTNFRSF14 on the right flank or vehicle on the left flank. Striking single agent effects were observed with near complete growth delay in sTNFRSF14-injected tumors (FIG. 20). Vehicle treated tumors grew significantly faster and to a larger size when compared to sTNFRSF14-treated tumors (FIG. 21). sTNFRSF14 treated tumors averaged a weight of only 0.75 grams while vehicle treated tumors weighed on average 3 grams 11 days after treatment initiation (FIG. 22). Tumors treated with sTNFRSF14 exhibited reduced levels of phosphorylated ERK as compared to vehicle-treated tumors (FIG. 23). sTNFRSF14-treated tumors also exhibited higher levels of TUNEL staining and a decrease in the proliferation marker Ki67 (FIG. 24). Taken together these results further confirm the utility of HVEM as a therapeutic target and the utility of soluble HVEM polypeptides as therapeutic agents, for example in Bcl2-positive follicular lymphomas.

Example 3

Targeted Delivery of Soluble HVEM Polypeptides to Tumors Using CAR T-Cells

It has recently emerged that CD19+B cell malignancies are sensitive to immune modulatory therapies including re-introduction of engineered chimeric antigen receptor (CAR) T cells (Brentjens, Riviere et al. 2011, Kalos, Levine et al. 2011, Kochenderfer, Dudley et al. 2012, Brentjens, Davila et al. 2013). These T cells express a CAR that allows for the generation of tumor targeted T cells that are capable of non-major histocompatibility tumor recognition and eradication. In addition, these T cells can be engineered to secrete additional factors, such as IL12, that increase the survival of mice with CD19+ tumors (Pegram, Purdon et al. 2015). As described herein, this scheme has now been modified to enable the treatment of CD19+B cell malignancies, such as FL, using soluble TNFRSF14/HVEM polypeptides. A schematic illustration of this approach is provided in FIG. 25.

Figures 26A, 26B:
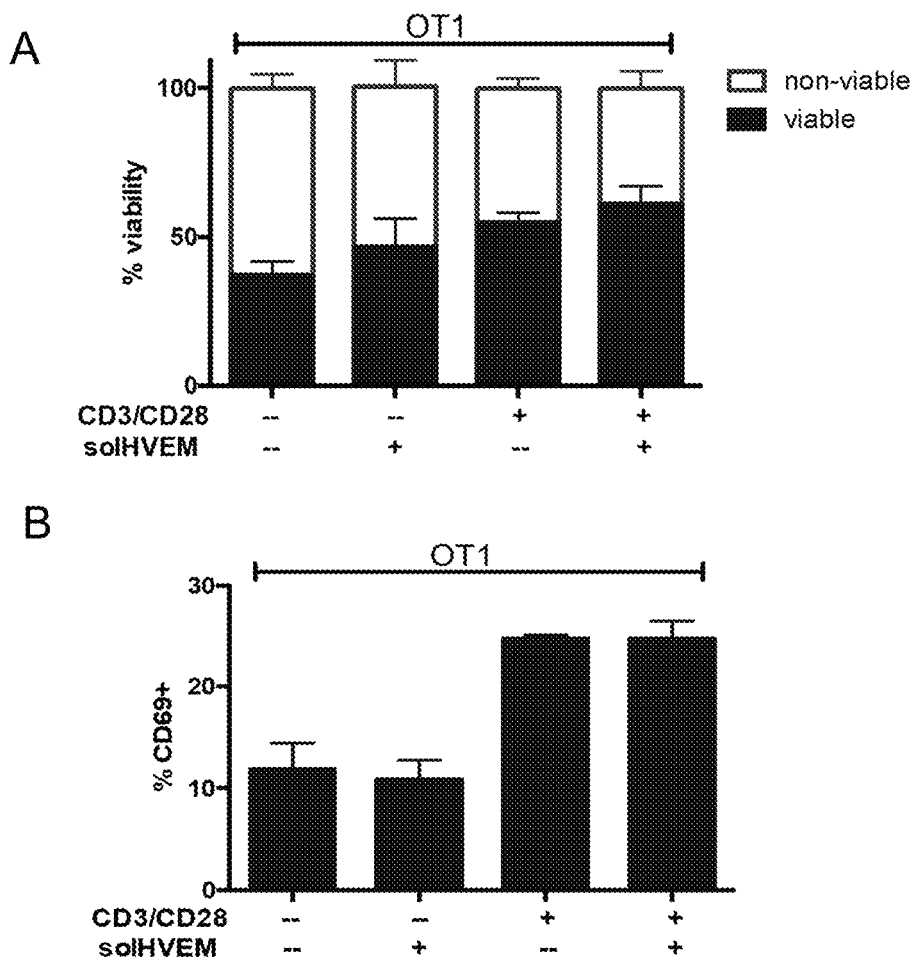
FIG. 26A-B. solHVEM does not have an effect on T cell viability or activation.

Experiments were first performed to determine if the soluble HVEM polypeptides have any effect on T-cell viability. FIG. 26A shows the viability of purified murine OT1 cells (n=2) cultured for 24 hours with or without stimulation by anti-CD3/anti-CD28 in the presence or absence of the soluble HVEM polypeptide (solHVEM: 10 m/m1); FIG. 26B shows the percentage of activated murine OT1 cells identified by FACS. These results demonstrated that soluble HVEM polypeptide expression did not have an effect on T cell viability or activation.

Figure 25B:
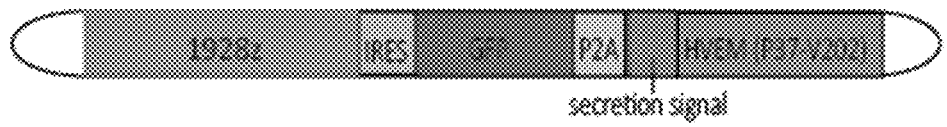

Next, a modified chimeric antigen receptor (CAR) construct was generated to allow for expression of both a CAR molecule and a soluble HVEM ectodomain polypeptide (as well as GFP) from the same construct/vector. The SFG-1928z vector was modified to include a nucleotide sequence encoding a human soluble HVEM polypeptide (HVEM P37-V202) downstream of a P2A proteolytic cleavage site and an IgG Kappa secretion signal, as illustrated in FIG. 25B. A nucleotide sequence encoding green fluorescent protein (GFP) was also included in the construct—downstream of the 1928z sequence—with an internal ribosomal entry site (IRES) between the GFP and 1928z sequences, as shown in FIG. 25B. A schematic representation of the resulting 1928-GFP-HVEM construct is shown in FIG. 25B. The nucleotide sequence of the resulting 1928-GFP-HVEM construct is provided in as SEQ ID NO. 9.

Next, human T cells were isolated from human PBMCs by density centrifugation, and activated and expanded by culturing with CD3/CD28 Dynobeads (Invitrogen) in the presence of IL2 (Peprotech) and phytohemagglutinin (Sigma). Transduction of T cells with the 1928-GFP-HVEM construct (or control constructs) was performed on rectronectin (Takara) covered plates. Upon T cell transduction, GFP+ cells were sorted and further expanded using CD3/Cd28 beads.

Figures 27A, 27B:
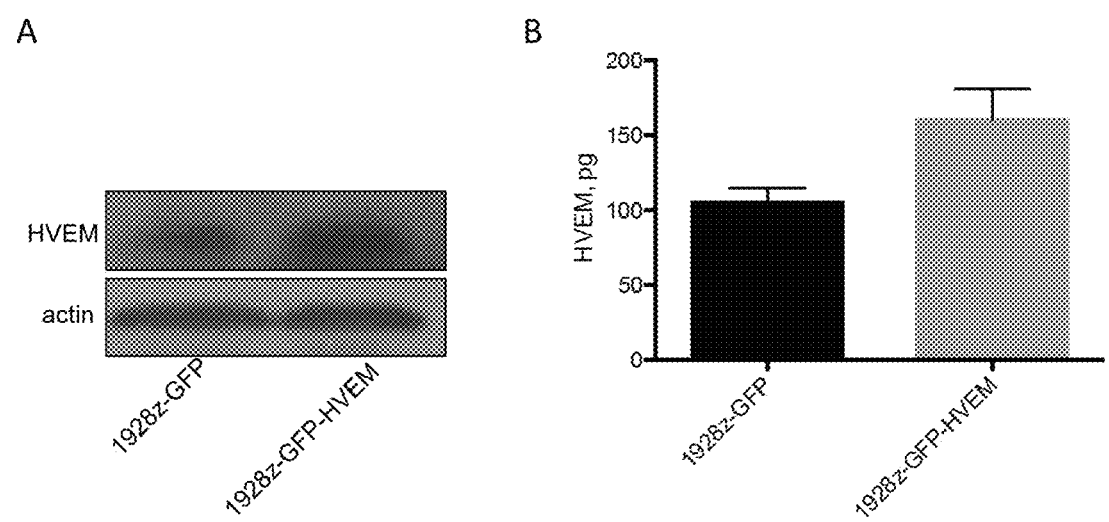
FIG. 27A-B. 19-28-HVEM-modified T cells, compared to 19-28 T cells, show increase in HVEM production and secretion (FIG. 27A) WB on FACS sorted CAR-T, and probed for HVEM (FIG. 27B) ELISA assay on HVEM shows increase in HVEM levels (p<0.1).

HVEM expression was assessed via western blot analysis of T cells containing either a 1928-GFP control construct (no HVEM) the 1928-GFP-HVEM construct (see FIG. 27A). HVEM secretion was confirmed by ELISA assay of cell culture supernatant using the Origene Human HVEM ELISA kit (see FIG. 27B). As shown in FIG. 27, the 1928-GFP-HVEM-modified T cells exhibited increased HVEM production and secretion as compared to control 1928 T cells.

Figures 28A, 28B:
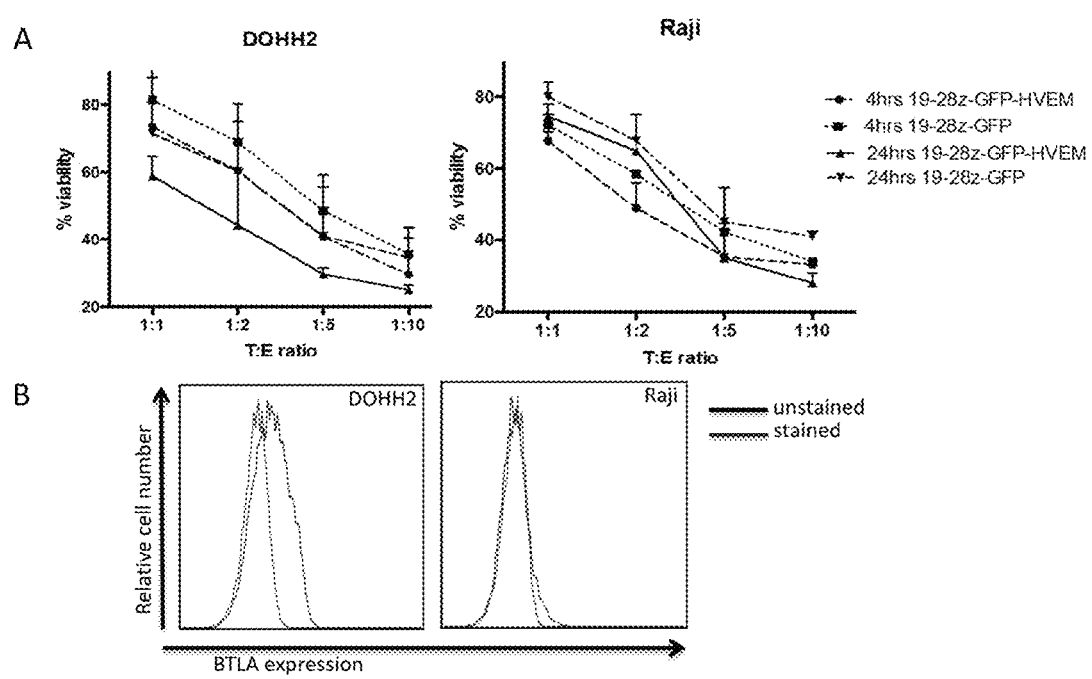
FIG. 28A-D.

The cytolytic capacity of the transduced T cells was determined by co-culturing target and effector cells at particular cell ratios. The target cells included DOHH2 and Raji cell lines, with high and low BTLA expression, respectively. After 4 or 24 hours of co-culture, cells were harvested and stained for DAPI and Annexin V and assayed by flow cytometry to detect residual GFP-negative viable cells. The results are provided in FIG. 28A-B.

Figure 28C:
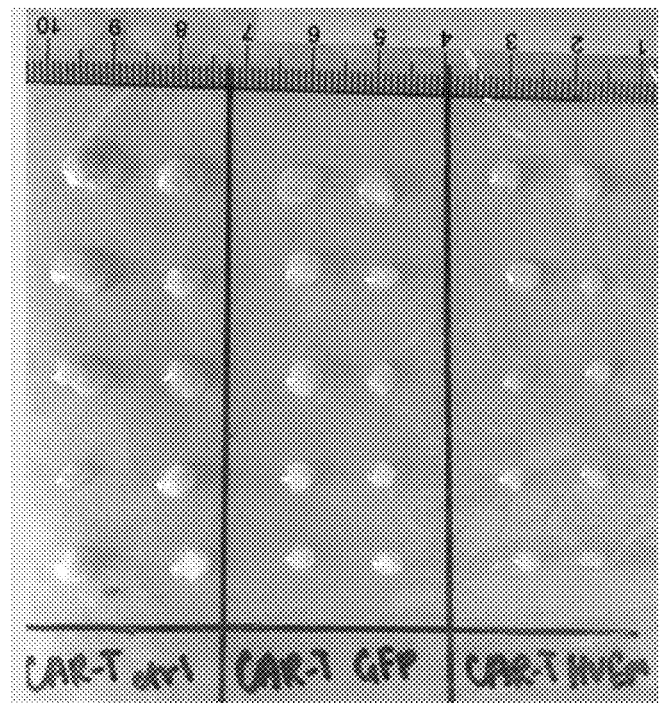
Figure 28D:
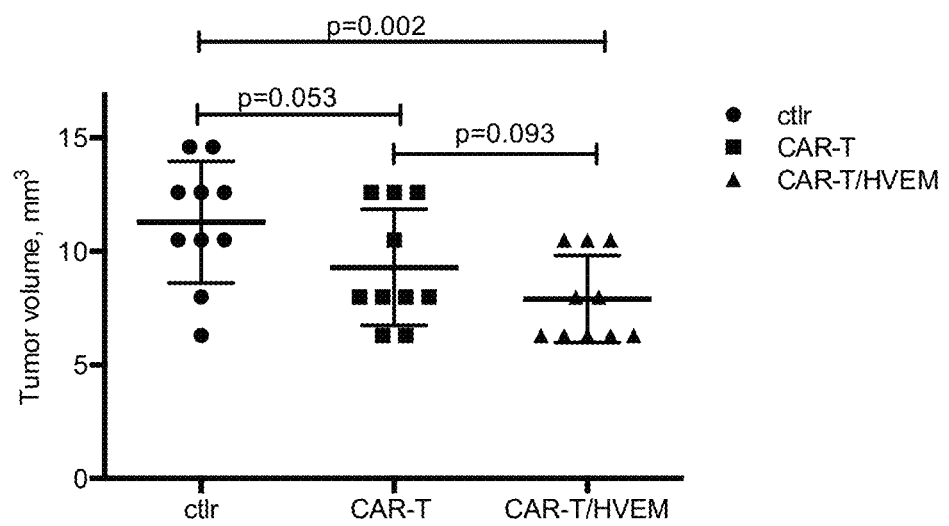

Xenografts were generated by subcutaneous injection (s.c.) of 5 Mio DoHH2 human lymphoma cells mixed with Matrigel (BD) into the flanks of NOD/SCID (NOD.CB17-Prkdc$^{scid}$/J) mice. Upon visible tumor formation (approximate volume 20 mm$^3$), mice were given a single dose of 1 Mio anti-CD19 CAR T cells with or without the HVEM secretion modification. T cells containing prostate-specific membrane antigen (PSMA) scFv were used as control CAR T cells. Tumor volumes were measured twice weekly. As demonstrated in FIG. 28C and FIG. 28D, the HVEM secreting CD19 CAR T-cells inhibited in vivo tumor growth to a greater degree than was observed with non-HVEM secreting CD19 CAR T-cells or with the control PSMA CAR T cells.

Example 4

Targeted Delivery of a Soluble HVEM Ectodomain Polypeptide Using an Anti-CD20 Antibody Soluble HVEM ectodomain polypeptides can be linked to any suitable tumor-targeting agent, such those agents that target B-cell lymphomas specifically. For example, in the present example soluble HVEM ectodomain polypeptides are covalently linked to the anti-CD20 antibody rituximab and then administered to subjects having a B-cell lymphoma. A similar targeting approach has already been shown to work with another extracellular tumor suppressor in FL (Oricchio, Nanjangud et al. 2011, Oricchio and Wendel 2012). Notably, this type of approach has benefits over current therapies including the reduction of off-target effects and the potential for use of soluble soluble HVEM ectodomain polypeptides at very low doses.

While the foregoing invention has been described in some detail for purposes of clarity and understanding, it will be clear to one skilled in the art from a reading of this disclosure that various changes in form and detail can be made without departing from the true spirit and scope of the invention. The invention may also be further defined in terms of the following claims.

REFERENCES

Aguzzi et al. (2014). Follicular dendritic cells: origin, phenotype, and function in health and disease. Trends Immunol 35, 105-113.

Ame-Thomas et al. (2015). CD10 delineates a subset of human IL-4 producing follicular helper T cells involved in the survival of follicular lymphoma B cells. Blood 125, 2381-2385.

Ame-Thomas et al. (2012). Characterization of intratumoral follicular helper T cells in follicular lymphoma: role in the survival of malignant B cells. Leukemia 26, 1053-1063.

Ame-Thomas et al. (2007). Human mesenchymal stem cells isolated from bone marrow and lymphoid organs support tumor B-cell growth: role of stromal cells in follicular lymphoma pathogenesis. Blood 109, 693-702.

Ame-Thomas et al. (2014). The yin and the yang of follicular lymphoma cell niches: role of microenvironment heterogeneity and plasticity. Semin Cancer Biol 24, 23-32.

Amin et al. (2015). DC-SIGN-expressing macrophages trigger activation of mannosylated IgM B-cell receptor in follicular lymphoma. Blood 126, 1911-1920.

Bagchi et al. (2008). "The quest for the 1p36 tumor suppressor." Cancer Res 68(8): 2551-2556.

Beroukhim et al. (2010). The landscape of somatic copy-number alteration across human cancers. Nature 463, 899-905.

Bjordahl et al. (2013). Lymphotoxin network pathways shape the tumor microenvironment. Current opinion in immunology 25, 222-229.

Bouska et al. (2014). Genome-wide copy-number analyses reveal genomic abnormalities involved in transformation of follicular lymphoma. Blood 123, 1681-1690.

Brentjens et al. (2013). "CD19-targeted T cells rapidly induce molecular remissions in adults with chemotherapy-refractory acute lymphoblastic leukemia." Sci Transl Med 5(177): 177ra138.

Brentjens et al. (2011). "Safety and persistence of adoptively transferred autologous CD19-targeted T cells in patients with relapsed or chemotherapy refractory B-cell leukemias." Blood 118(18): 4817-4828.

Brentj ens et al. (2007). "Genetically targeted T cells eradicate systemic acute lymphoblastic leukemia xenografts." Clin Cancer Res 13(18 Pt 1): 5426-5435.

Cai et al. (2009). The CD160, BTLA, LIGHT/HVEM pathway: a bidirectional switch regulating T-cell activation. Immunological reviews 229, 244-258.

Challa-Malladi et al. (2011). Combined Genetic Inactivation of 02-Microglobulin and CD58 Reveals Frequent Escape from Immune Recognition in Diffuse Large B Cell Lymphoma. Cancer Cell 20, 728-740.

Chang et al. (2015). Stromal infrastructure of the lymph node and coordination of immunity. Trends Immunol 36, 30-39.

Cheung et al. (2010). Acquired TNFRSF14 mutations in follicular lymphoma are associated with worse prognosis. Cancer Res 70, 9166-9174.

Cheung et al. (2005). Evolutionarily divergent herpesviruses modulate T cell activation by targeting the herpesvirus entry mediator cosignaling pathway. Proc Natl Acad Sci USA 102, 13218-13223.

Cheung et al. (2009). T cell intrinsic heterodimeric complexes between HVEM and BTLA determine receptivity to the surrounding microenvironment. J Immunol 183, 7286-7296.

Crotty, S. (2014). T follicular helper cell differentiation, function, and roles in disease. Immunity 41, 529-542.

De Silva et al. (2015). Dynamics of B cells in germinal centres. Nature reviews Immunology 15, 137-148.

del Rio et al. (2010). HVEM/LIGHT/BTLA/CD160 cosignaling pathways as targets for immune regulation. J Leukoc Biol 87, 223-235.

Egle et al. (2004). VavP-Bcl2 transgenic mice develop follicular lymphoma preceded by germinal center hyperplasia. Blood 103, 2276-2283.

Festing, M. F. (2002). The design and statistical analysis of animal experiments. ILAR J 43, 191-193.

Fitzgibbon et al. (2007). Genome-wide detection of recurring sites of uniparental disomy in follicular and transformed follicular lymphoma. Leukemia 21, 1514-1520.

Fletcher et al. (2015). Lymph node fibroblastic reticular cells in health and disease. Nature reviews Immunology 15, 350-361.

Fridy et al. (2014). A robust pipeline for rapid production of versatile nanobody repertoires. Nature Methods 11(12): 1253-60.

Gavrieli et al. (2003). Characterization of phosphotyrosine binding motifs in the cytoplasmic domain of B and T lymphocyte attenuator required for association with protein tyrosine phosphatases SHP-1 and SHP-2. Biochemical and biophysical research communications 312, 1236-1243.

Guilloton et al. (2012). Mesenchymal stromal cells orchestrate follicular lymphoma cell niche through the CCL2-dependent recruitment and polarization of monocytes. Blood 119, 2556-2567.

Jackson et al. (2016). "Driving CAR T-cells forward." Nat Rev Clin Oncol.

Kalos et al. (2011). "T cells with chimeric antigen receptors have potent antitumor effects and can establish memory in patients with advanced leukemia." Sci Transl Med 3(95): 95ra73.

Kochenderfer et al. (2012). "B-cell depletion and remissions of malignancy along with cytokine-associated toxicity in a clinical trial of anti-CD19 chimeric-antigen-receptor-transduced T cells." Blood 119(12): 2709-2720.

Launay et al. (2012). High rate of TNFRSF14 gene alterations related to 1p36 region in de novo follicular lymphoma and impact on prognosis. Leukemia 26, 559-562.

Li et al. (2014). Mutations in linker histone genes HIST1H1 B, C, D, and E; OCT2 (POU2F2); IRF8; and ARID1A underlying the pathogenesis of follicular lymphoma. Blood 123, 1487-1498.

Lohr et al. (2012). Discovery and prioritization of somatic mutations in diffuse large B-cell lymphoma (DLBCL) by whole-exome sequencing. Proc Natl Acad Sci USA 109, 3879-3884.

M'Hidi et al. (2009). High expression of the inhibitory receptor BTLA in T-follicular helper cells and in B-cell small lymphocytic lymphoma/chronic lymphocytic leukemia. American journal of clinical pathology 132, 589-596.

Mavrakis et al. (2008). Tumorigenic activity and therapeutic inhibition of Rheb GTPase. Genes Dev 22, 2178-2188.

Montgomery et al. (1996). "Herpes simplex virus-1 entry into cells mediated by a novel member of the TNF/NGF receptor family." Cell 87(3): 427-436.

Morin et al. (2011). Frequent mutation of histone-modifying genes in non-Hodgkin lymphoma. Nature 476, 298-303.

Mourcin et al. (2012). Stromal cell contribution to human follicular lymphoma pathogenesis. Frontiers in immunology 3, 280.

Mueller et al. (2009). Stromal cell contributions to the homeostasis and functionality of the immune system. Nature reviews Immunology 9, 618-629.

Murphy et al. (2006). Balancing co-stimulation and inhibition with BTLA and HVEM. Nature reviews Immunology 6, 671-681.

Murphy et al. (2010). "Slow down and survive: Enigmatic immunoregulation by BTLA and HVEM." Annu Rev Immunol 28: 389-411.

Okosun et al. (2014). Integrated genomic analysis identifies recurrent mutations and evolution patterns driving the initiation and progression of follicular lymphoma. Nat Genet 46, 176-181.

Olshen et al. (2004). Circular binary segmentation for the analysis of array-based DNA copy number data. Biostatistics 5, 557-572.

Oricchio et al. (2011). The Eph-receptor A7 is a soluble tumor suppressor for follicular lymphoma. Cell 147, 554-564.

Oricchio & Wendel (2012). "Mining the cancer genome uncovers therapeutic activity of EphA7 against lymphoma." Cell Cycle 11(6): 1076-1080.

Ortega-Molina et al. (2015). The histone lysine methyltransferase KMT2D sustains a gene expression program that represses B cell lymphoma development. Nat Med 21, 1199-1208.

Pangault et al. (2010). Follicular lymphoma cell niche: identification of a preeminent IL-4-dependent T(FH)-B cell axis. Leukemia 24, 2080-2089.

Park et al. (2012). Expression of anti-HVEM single-chain antibody on tumor cells induces tumor-specific immunity with long-term memory. Cancer Immunol. Immunother. 61(2), 203-14.

Pasero et al. (2012). The HVEM network: new directions in targeting novel costimulatory/co-inhibitory molecules for cancer therapy. Current opinion in pharmacology 12, 478-485.

Pasqualucci et al. (2014). Genetics of follicular lymphoma transformation. Cell reports 6, 130-140.

Pegram et al. (2015). "IL-12-secreting CD19-targeted cord blood-derived T cells for the immunotherapy of B-cell acute lymphoblastic leukemia." Leukemia 29(2): 415-422.

Ramos et al. (2016). "CAR-T Cell Therapy for Lymphoma." Annu Rev Med 67: 165-183.

Rehm et al. (2011). Cooperative function of CCR7 and lymphotoxin in the formation of a lymphoma-permissive niche within murine secondary lymphoid organs. Blood 118, 1020-1033.

Roozendaal & Mebius (2011). Stromal cell-immune cell interactions. Annual review of immunology 29, 23-43.

Ross et al. (2007). Comprehensive analysis of copy number and allele status identifies multiple chromosome defects underlying follicular lymphoma pathogenesis. Clin Cancer Res 13, 4777-4785.

Sadelain (2015). "CAR therapy: the CD19 paradigm." J Clin Invest 125(9): 3392-3400.

Steinberg et al. (2011). The signaling networks of the herpesvirus entry mediator (TNFRSF14) in immune regulation. Immunological reviews 244, 169-187.

Vendel et al. (2009). B and T lymphocyte attenuator regulates B cell receptor signaling by targeting Syk and BLNK. J Immunol 182, 1509-1517.

Watanabe et al. (2003). BTLA is a lymphocyte inhibitory receptor with similarities to CTLA-4 and PD-1. Nature immunology 4, 670-679.

Wendel et al. (2004). Survival signalling by Akt and eIF4E in oncogenesis and cancer therapy. Nature 428, 332-337.

Yildiz et al. (2015). Activating STAT6 mutations in follicular lymphoma. Blood 125, 668-6

The invention claimed is:

1. A vector for expression of both a chimeric antigen receptor (CAR) and a soluble HVEM ectodomain polypeptide in a T cell, the vector comprising:
   (a) a nucleotide sequence encoding a CAR that binds to CD19, and
   (b) a nucleotide sequence encoding a soluble HVEM ectodomain polypeptide and a secretion signal upstream of the HVEM ectodomain polypeptide,
   wherein the CAR comprises the complementarity determining regions of the anti-CD19 CAR encoded by SEQ ID NO. 9, and
   wherein the soluble HVEM ectodomain polypeptide comprises a HVEM CRD1 domain, a HVEM CRD2 domain, and a HVEM CRD3 domain.

2. The vector of claim 1, wherein the nucleotide sequence encoding the soluble HVEM ectodomain polypeptide comprises SEQ ID NO. 3, 5, or 7.

3. The vector of claim 1, wherein the nucleotide sequence encoding the soluble HVEM ectodomain polypeptide encodes amino acids 42-162 of SEQ ID NO. 2.

4. The vector of claim 1, wherein the CAR is the anti-CD19 CAR encoded by SEQ ID NO. 9.

5. The vector of claim 1 further comprising a GFP coding sequence.

6. The vector of claim 1 further comprising a proteolytic cleavage site.

7. The vector of claim 1 comprising, from 5' to 3', (a) the nucleotide sequence encoding the CAR that binds to CD19, (b) an internal ribosomal entry site (IRES) and (c) the nucleotide sequence encoding the soluble HVEM ectodomain polypeptide.

8. The vector of claim 1 comprising, from 5' to 3', (a) the nucleotide sequence encoding the CAR that binds to CD19, (b) an internal ribosomal entry site (IRES), (c) a GFP coding sequence, (d) a proteolytic cleavage site, (e) a secretion signal, and (f) the nucleotide sequence encoding the soluble HVEM ectodomain polypeptide.

9. The vector according to claim 1 comprising SEQ ID NO. 9.

10. A genetically modified T-cell comprising the vector of claim 1.

11. The genetically modified T-cell of claim 10, wherein the nucleotide sequence encoding the soluble HVEM ectodomain polypeptide comprises SEQ ID NO. 3, 5, or 7.

12. A genetically modified T-cell comprising the vector of claim 8.

13. A genetically modified T-cell comprising the vector of claim 9.

* * * * *